US011628213B2

(12) United States Patent
Curtiss, III et al.

(10) Patent No.: US 11,628,213 B2
(45) Date of Patent: Apr. 18, 2023

(54) ICHTHYOPHTHIRIUS MULTIFILIIS VACCINE SYSTEM

(71) Applicant: University of Florida Research Foundation, Inc., Gainesville, FL (US)

(72) Inventors: Roy Curtiss, III, Gainesville, FL (US); Banikalyan Swain, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/963,761

(22) PCT Filed: Jan. 23, 2019

(86) PCT No.: PCT/US2019/014672
§ 371 (c)(1),
(2) Date: Jul. 21, 2020

(87) PCT Pub. No.: WO2019/147614
PCT Pub. Date: Aug. 1, 2019

(65) Prior Publication Data
US 2021/0093704 A1 Apr. 1, 2021

Related U.S. Application Data

(60) Provisional application No. 62/621,567, filed on Jan. 24, 2018.

(51) Int. Cl.
| | |
|---|---|
| *A61K 39/02* | (2006.01) |
| *A61K 39/395* | (2006.01) |
| *C12N 1/20* | (2006.01) |
| *A61K 39/00* | (2006.01) |

(52) U.S. Cl.
CPC ...... *A61K 39/025* (2013.01); *A61K 39/39533* (2013.01); *C12N 1/20* (2013.01); *A61K 2039/522* (2013.01)

(58) Field of Classification Search
CPC ............ A61K 39/025; A61K 39/39533; A61K 2039/522; C12N 1/20; C12N 1/205
See application file for complete search history.

(56) References Cited

U.S. PATENT DOCUMENTS

| | | | |
|---|---|---|---|
| 6,780,405 B1 | 8/2004 | Curtiss, III et al. | |
| 7,026,156 B1* | 4/2006 | Clark | A61K 39/002 435/252.3 |
| 9,045,742 B2* | 6/2015 | Curtiss, III | A61P 31/04 |
| 2007/0071776 A1 | 3/2007 | Sin et al. | |
| 2016/0199467 A1* | 7/2016 | Curtiss, III | A61K 35/74 424/200.1 |

FOREIGN PATENT DOCUMENTS

WO  2018007632 A1  1/2018

OTHER PUBLICATIONS

Choe et al., 2017 (Edwardsiella piscicida lacking the cyclic AMP receptor protein (crp) is avirulent and immunogenic in fish; Fish Shellfish Immunology 68:243-250). (Year: 2017).*
Bujan et al. 2018 (Genetic studies to re-affiliate Edwardsiella tarda fish isolates to Edwardsiella piscicida and Edwardsiella anguillarum species; Systematic and Applied Microbiology; 41:30-37). (Year: 2018).*
Notification of International Search Report and Written opinion of International Application No. PCT/US2019/014672 dated Apr. 15, 2019.
Liu et al. "Transcriptomic dissection of the horizontally acquired response regulator EsrB reveals its global regulatory roles in the physiological adaptation and activation of T3SS and the cognate effector repertoire in Edwardsiella piscicida during infection toward turbot," Virulence, Jun. 5, 2017 (Jun. 5, 2017), vol. 8, Iss. 7, pp. 1355-1377.
(Hou et al. "Identification and functional characterization of EseH, a new effector of the type III secretion system of Edwardsiella piscicida," Cellular Microbiology, Jul. 26, 2016 (Jul. 26, 2016), vol. 19, No. 1, e12638, pp. 1-11.
Complete Genome Sequence of an Edwardsiella piscicida-Like Species, Recovered from Tilapia in the United States. Reichley SR, Waldbieser GC, Lawrence ML, Griffin MJ. Genome Announc. Sep. 3, 2015;3(5):e01004-15. doi: 10.1128/genomeA.01004-15. PMID: 26337892 Free PMC article. 134.
Complete Genome Sequence of an Edwardsiella piscicida-Like Species Isolated from Diseased Grouper in Israel. Reichley SR, Waldbieser GC, Ucko M, Colomi A, Dubytska L, Thune RL, Lawrence ML, Griffin MJ. Genome Announc. Jul. 23, 2015;3(4):e00829-15. doi: 10.1128/genomeA.00829-15. PMID: 26205870 Free PMC article.
Real-time polymerase chain reaction assays for the detection and quantification of Edwardsiella tarda, Edwardsiella piscicida, and Edwardsiella piscicida-like species in catfish tissues and pond water. Reichley SR, Ware C, Greenway TE, Wise DJ, Griffin MJ. J Vet Diagn Invest. Mar. 2015;27(2):130-9. doi: 10.1177/1040638714566672. Epub Jan. 22, 2015. PMID: 25613040 137.

(Continued)

*Primary Examiner* — Mary Maille Lyons
(74) *Attorney, Agent, or Firm* — Thomas | Horstemeyer, LLP

(57) ABSTRACT

Disclosed herein are nucleic acids, vector systems, and vaccines for vaccinating fresh water and marine fish using *Ichthyophthirius multifiliis* (Ich) i-antigens. In particular, a recombinant attenuated *Edwardsiella* vaccine (RAEV) vector system is disclosed with regulated delayed attenuation and regulated delayed lysis in vivo attributes that synthesizes Ich protective antigens to enable vaccination of fresh water and marine fish species susceptible to white spot disease. This vaccine construct is designed to exhibit the invasive properties of virulent *Edwardsiella* at the time of bath immunization and then is programmed to gradually lose virulence attributes and to synthesize protective antigens as a consequence of in vivo cell division as the RAEV colonizes internal effector lymphoid tissues. The ultimate lysis in vivo delivers a bolus of protective antigen along with immunostimulatory molecules to exhibit complete biological containment with no potential for survival in vivo or ex vivo.

23 Claims, 25 Drawing Sheets

Specification includes a Sequence Listing.

(56) References Cited

OTHER PUBLICATIONS

Draft Genome Sequences of Two Genetic Variant Strains of Edwardsiella piscicida, JF1305 and RSB1309, Isolated from Olive Flounder (*Paralichythys olivaceus*) and Red Sea Bream (*Pagrus major*) Cultured in Japan, Respectively. Oguro K, Tamura K, Yamane J, Shimizu M, Yamamoto T, Ikawa T, Ohnishi K, Oshima S, Imajoh M. Genome Announc. Jun. 12, 2014;2(3):e00546-14. doi: 10.1128/genomeA.00546-14. PMID: 24926054 Free PMC article.

*Edwardsiella piscicida* sp. nov., a novel species pathogenic to fish. Abayneh T, Colquhoun DJ, Sørum H. J Appl Microbiol. Mar. 2013;114(3):644-54. doi: 10.1111/jam.12080. Epub Jan. 7, 2013. PMID: 23167785 Free article.

Edwardsiella tarda: A Classic Presentation of a Rare Fatal Infection, with Possible New Background Risk Factors. Healey KD, Rifai SM, Rifai AO, Edmond M, Baker DS, Rifai K. Am J Case Rep. Dec. 7, 2021;22:e934347. doi: 10.12659/AJCR.934347. PMID: 34873141 Free PMC article.

Edwardsiella tarda, a rare human pathogen isolated from a perihepatic abscess: Implications of transient versus long term colonization of the gastrointestinal tract. Pham K, Wu Y, Turett G, Prasad N, Yung L, Rodriguez GD, Segal-Maurer S, Urban C, Yoon J. IDCases. Sep. 6, 2021;26:e01283. doi: 10.1016/j.idcr.2021.e01283. eCollection 2021. PMID: 34527514 Free PMC article.

Fulminant septic shock due to Edwardsiella tarda infection associated with multiple liver abscesses: a case report and review of the literature. Bakirova GH, Alharthy A, Corcione S, Aletreby WT, Mady AF, De Rosa FG, Karakitsos D. J Med Case Rep. Sep. 9, 2020;14(1):144. doi: 10.1186/s13256-020-02469-8. PMID: 32900379 Free PMC article. Review.

Early-onset Edwardsiella tarda septicemia in an extremely preterm infant. Egashira M, Higuchi N, Shichijo A, Egashira T, Takayanagi T. Pediatr Int. Jul. 2020;62(7):860-861. doi: 10.1111/ped.14189. Epub Jun. 10, 2020. PMID: 32519417 No abstract available.

Edwardsiella tarda Bacteremia, Okayama, Japan, 2005-2016. Kamiyama S, Kuriyama A, Hashimoto T. Emerg Infect Dis. Oct. 2019;25(10):1817-23. doi: 10.3201/eid2510.180518. PMID: 31539320 Free PMC article.

Neonatal sepsis following maternal amnionitis by Edwardsiella tarda: A case report and a review of the literature. Article in European Journal of Pediatrics • Jan. 2011, DOI: 10.1007/s00431-010-1285-5 • Source: PubMed.

* cited by examiner

Genotype:

X16001: Δ*fur*

X16012:
ΔP$_{fur170}$::TT *araC* P$_{BAD}$ *fur*

ICHTHYOPHTHIRIUS MULTIFILIIS VACCINE SYSTEM

CROSS-REFERENCE TO RELATED APPLICATION

This application is the 35 U.S.C. 0 371 national stage application of PCT Application No. PCT/US2019/014672, entitled "ICHTYOPHTHIRIUS MULTIFILIIS VACCINE SYSTEM," filed Jan. 23, 2019, which claims priority to, and the benefit of, U.S. Provisional Application entitled "ICHTYOPHTHIRIUS MULTIFILIIS VACCINE SYSTEM," having Ser. No. 62/621,567, filed on Jan. 24, 2018, both of which are entirely incorporated herein by reference as if fully set forth herein.

STATEMENT REGARDING FEDERALLY SPONSORED RESEARCH OR DEVELOPMENT

This invention was made with government support under 2018-67015-28286 awarded by United States Department of Agriculture, NIFA. The government has certain rights in the invention.

SEQUENCE LISTING

The Sequence Listing for this application is labeled "222110_2640_sequence listing_ST25.txt" which was created on Jan. 23, 2019 and is 45 KB. The entire content of the sequence listing is incorporated herein by reference in its entirety.

BACKGROUND

The worldwide decline of ocean fisheries stocks has provided impetus for rapid growth of aquaculture, i.e., fish, crustacean, and shellfish farming. Currently the aquaculture industry is one of the most important sources of human food and it has the fastest growth-rate of all animal-producing food sectors. In the U.S., aquaculture is the fastest growing animal food-producing segment of agriculture generating an annual revenue of approximately $1.3 billion in the U.S. The contribution of aquaculture to the global fish supply by weight has increased from 3.9 percent in 1970 to 50 percent in 2008, with a value of $98.3 billion. In 2008, it was predicted that the annual global consumption of seafood by 2010 would be 110-120 million metric tons. In fact, the latest statistics show that fisheries production for direct human consumption increased to more than 136 million tons in 2012. The need for increased aquaculture output over the next 20 years is essential to deal with human population growth projections, anticipated economic development, and concern over the future sustainability of capture fisheries. Today the global aquaculture industry is challenged to increase sustainable production, reduce environmental contamination and diversify production. Economic losses due to infectious diseases in the global aquaculture industry are estimated to be $3 billion annually. In all kinds of intensive animal production, where single or multiple species are reared in high density, infectious disease agents are easily transmitted between individuals. In these systems, vaccination is a most important enhancer of production yields. Currently, the most-used method for vaccination in the global aquaculture industry is intra-coelomic (i.c., also referred to as intracoelemic or intracolemic) injection. This type of immunization is expensive due to labor and added costs for anesthesia, gas, needles and electricity. Furthermore, i.c. vaccination is cost prohibitive for booster immunizations. However, in all kinds of intensive aquaculture where infectious disease agents are easily transmitted, vaccination would be the most effective method to prevent infectious diseases and their associated economic losses.

*Ichthyophthirius multifiliis* (Ich), which causes white spot disease in fresh water fish, is a protozoan parasite that causes significant disease problems for the U.S. channel catfish aquaculture industry. Ich completes its life cycle every 7-10 days at 22° C. While infections are often lethal, fish that survive epizootics (or controlled laboratory infections) develop acquired protective immunity against subsequent challenge. Five different strains (serotypes) have been identified and fish that are immune from exposure to one serotype are less susceptible to infection by heterologous serotypes. In response to infection, fish produce antibodies that are directed primarily against a class of abundant GPI-anchored surface membrane proteins of Ich that are analogous to the immobilization antigens (i-antigens) of free-living ciliates. High titer sera that strongly immobilize Ich are produced in response to infection.

Live recombinant immersion vaccines, which protect against several diseases by expressing multiple protective antigens at low cost, have not yet been developed for the aquaculture industry. Efforts are therefore needed to provide safe efficacious vaccines that would be cost-effective to manufacture and administer. In this regard, a vaccine vector system that would enable synthesis and delivery of antigens encoded by genes form multiple fish pathogens that would induce protective immunity to these pathogens causing infections in fish would be desirable.

An additional benefit of vaccine vector systems as described herein is that protection against disease caused by *Edwardsiella* vector, in addition to that of Ich, is also a benefit a two for one vaccine.

SUMMARY

I-antigens are immunodominant, and their role in protective immunity against Ich infections has been clearly established. There are no commercial vaccines for Ich, but defined protective antigens (immobilization antigens [i-antigens]) elicit immunity against infection. Disclosed herein are nucleic acids, vector systems, and vaccines for vaccinating fish using Ich i-antigens.

Described herein are genetically modified (i.e. recombinant) *Edwardsiella piscicida* bacterium displaying a regulated delayed manifestation of attenuation in vivo, able to synthesize and deliver protective antigens encoded by genes from heterologous pathogens and capable of infecting fresh water and marine fish to deliver such synthesized protective antigens.

Bacterium as described herein can further comprise a chromosomally integrated regulatable promoter operably linked to a nucleic acid sequence encoding an attenuation protein such that transcription of the nucleic acid sequence encoding the attenuation protein occurs in a permissive environment, but ceases in a non-permissive in vivo environment.

In certain aspects, bacterium as described herein can elicit an immune response against a fish pathogen other than *Edwardsiella piscicida* in a host. The fish pathogen can be a bacterial, viral, fungal or parasitic pathogen of fish.

Bacterium as described herein can be capable of regulated cell lysis.

Bacterium as described herein can synthesize components of the peptidoglycan cell wall layer under permissive conditions and unable to do so under non-permissive in vivo conditions.

The bacterium can be capable of the regulated expression of at least one heterologous nucleic acid encoding an antigen, wherein the bacterium comprises at least one chromosomally integrated nucleic acid sequence encoding a repressor.

In embodiments of the present disclosure, protective antigens are encoded by genetic sequences from the parasite *Ichthyophthirius muitifiliis*. In embodiments of the present disclosure, protective antigens are encoded by genetic sequences from the parasite *Ichthyophthirius multifiliis* that have been codon modified for optimal synthesis of protein antigens with the same amino acid sequences as the protein antigens synthesized by *Ichthyophthirius multifiliis*. The *Ichthyophthirius multifiliis* protective antigen can be *Ichthyophthirius multifiliis* immobilization antigen precursor (IAG48), *Ichthyophthirius multifiliis* immobilization antigen isoform (IAG52A or IAG52B), or a combination thereof.

Bacterium as described herein can comprise at least one chromosomally integrated nucleic acid sequence encoding a repressor operably linked to a regulatable promoter, and a vector comprising at least one nucleic acid sequence encoding a protective antigen operably linked to a promoter regulated by the repressor, such that the expression of the nucleic acid sequence encoding the antigen is repressed during in vitro growth of the bacterium, but the bacterium is capable of high level expression in vivo.

Bacterium as described herein can comprise at least one mutation selected from the group consisting of: ΔasdA, Δfur, Δpmi, Δcrp, ΔznuA, Δwaal, Δcrp, ΔznuA, $\Delta P_{rfaH}$::TT araC $P_{araBAD}$ rfaH, $\Delta P_{rfaH}$::TT araC $P_{araBAD}$rfaH, $\Delta P_{crp}$::TT araC $P_{araBAD}$ crp, $\Delta P_{crp}$::TT araC $P_{araBAD}$ crp, $\Delta P_{fur}$::TT araC $P_{araBAD}$ fur, ΔpstS, $\Delta P_{pstS}$::TT araC $P_{araBAD}$ pstS, ΔasdA; $\Delta P_{fur}$::TT araC $P_{araBAD}$ fur, $\Delta P_{murA}$::TT araC $P_{araBAD}$ murA, ΔΔasdA; $\Delta P_{murA}$::TT araC $P_{BAD}$ murA, ΔasdA; $\Delta P_{fur}$::TT araC $P_{araBAD}$ fur, $\Delta P_{murA}$:TT araC $P_{araBAD}$ murA, ΔaroA, ΔphoP, ΔasdA; $\Delta P_{fur}$::TT araC $P_{araBAD}$ fur; ΔaroA, ΔasdA; $\Delta P_{fur}$:TT araC $P_{araBAD}$ fur; $\Delta P_{crp}$::TT araC $P_{araBAD}$ crp, $\Delta P_{rfaD}$::TT araC $P_{araBAD}$ rfaD, $\Delta P_{lacI}$::TT araC $P_{araBAD}$ lacI, ΔasdA; $\Delta P_{fur}$::TT araC $P_{araBAD}$ fur; $\Delta P_{murA}$::TT araC $P_{araBAD}$ murA; $\Delta P_{lacI}$::TT araC $P_{araBAD}$ lacI, ΔasdA10; $\Delta P_{fur}$::TT araC $P_{araBAD}$ fur; □$P_{crp}$:TT araC $P_{araBAD}$ crp; $\Delta P_{lacI}$::TT araC $P_{araBAD}$ lacI, ΔasdA; and $\Delta P_{fur}$::TT araC $P_{araBAD}$ fur, $\Delta P_{murA}$::TT araC $P_{araBAD}$ murA. Bacterium as described herein can comprise any combination of one or more of the mutations listed above.

Bacterium as described herein can be non-auxotrophoc.

Described herein are vaccine compositions comprising a recombinant bacterium as described herein.

Also described herein are methods of eliciting an immune response in a fish, the method comprising administering a bacterium as described herein or a vaccine to a fish. The immune response can be a protective immune response. Methods as described herein can further comprise delivering a bolus of antigen to the fish, wherein delivering a bolus of antigen comprises lysing the *Edwardsiella* bacterium. Administering can be one or more of administering by bath immersion, oral administration, or intracoelomic administration. The fish can be a teleost fish; the fish can be a farmed teleost fish; the fish can be a catfish; the fish can be a channel catfish; the fish can be a zebrafish, Also described herein are kits. Kits as described herein can comprise a bacterium as described herein. The bacterium of the kit can be lyophilized.

The details of one or more embodiments of the present disclosure are set forth in the accompanying drawings and the description below. Other features, objects, and advantages of the invention will be apparent from the description and drawings, and from the claims.

DESCRIPTION OF DRAWINGS

FIGS. 1A-1B. FIG. 1A is an illustration of an antibiotic-sensitive *Edwardsiella* ΔasdA mutant suicide vector technology. FIG. 1B is a gel verifying the mutant.

FIG. 2 is a graph showing growth curve analysis of wild-type and ΔasdA mutant *Edwardsiella piscicida* with and without diaminopimelic acid (DAP).

FIG. 3 is a graph showing complementation of ΔasdA mutant strain (χ16000) with *E. piscicida* asdA gene.

FIG. 4 is an illustration of a pG8R8018 $Asd^+$ vector possessing only the SD-asdA gene from *E. piscicida* with a modified start codon from ATG to GIG.

FIG. 5 is an illustration of a pG8R8018 $Asd^+$ vector modified to express green florescent protein (GFP).

FIGS. 6A-6C: Determination of arabinose absence in catfish tissues. FIG. 6A is an illustration of arabinose-regulatable expression of GFP in *E. piscicida*. FIG. 6B. The plasmid pYA3700 encoding araC $P_{araBAD}$ gfp was electroporated into *E. piscicida* J118 and grown in media with 10% macerated catfish tissues without or with 0.2% arabinose. Arabinose-dependent expression of GFP by *E. piscicida* was examined by fluorescence microscopy. FIG. 6C. The arabinose-dependent conditionally lethal *E. piscicida* strain χ16016 ($\Delta P_{murA180}$::TT araC $P_{araBAD}$ murA) was used to detect presence of arabinose in catfish that would support growth and prevent lysis. The growth of χ16016 in Unpurple broth, supplemented with 10% catfish tissue without or with 0.2% arabinose was inoculated with a 1:2000 dilution of an overnight culture grown in Unpurple broth with 0.1% arabinose.

FIGS. 7A-7B. FIG. 7A is an illustration for genotype verification of $\Delta P_{fur170}$:TT araC $P_{BAD}$ fur deletion-insertion mutation. FIG. 7B is a gel verifying the mutation by polymerase chain reaction (FOR).

FIGS. 8A-8B. FIG. 8A illustrates an in-frame deletion of fur gene in *E. piscicida*, which is verified by PCR as shown in the gel of FIG. 8B.

FIG. 9 is an illustration of a fur complementation plasmid.

FIGS. 10A-10B. FIG. 10A shows analysis of Fur protein synthesis and complementation using χ16001 vector (Δfur, with or without pG8R8021) and χ16012 vector ($\Delta P_{fur170}$:TT araC $P_{BAD}$ fur, with or without arabinose) via immunoblot. FIG. 10B shows growth curves of native strains J118, χ16001 vector (Δfur, with or without pG8R8021), and χ16012 with and without arabinose.

FIG. 11 shows wild type, χ16010, and χ16011 vectors streaked on MacConkey maltose agar without and with 0.2% arabinose.

FIGS. 12A-12D. Evaluation of IAG52B and IAG48 synthesis in *E. coli* and RAEV. FIG. 12A is an illustration of an embodiment of a plasmid map of balanced-lethal vector pG8R8022 with type II secretion signal (bla SS), used for the synthesis of i-antigens. FIG. 12B is a western blot analysis of IAG52B synthesized in *E. coli* χ6212, lane 1: induced with 1 mM IPTG and lane 2: uninduced. FIG. 12C is a western blot analysis of IAG48 synthesized in χ6212, lane 1: induced with 1 mM IPTG and lane 2: uninduced, FIG. 12D is a western blot analysis of IAG52 synthesized in *E. piscicida* χ16015(pG6R6023).

FIG. 13 is an illustration of a vector construct encoding an embodiment of the IAG52B *Ichthyophthirius multifiliis* (Ich) antigen.

Figure 16A:
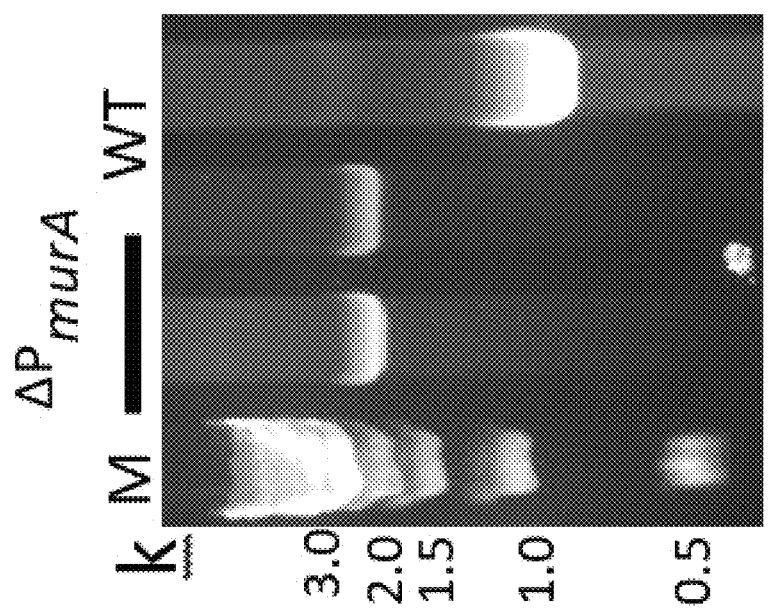
Figure 16B:
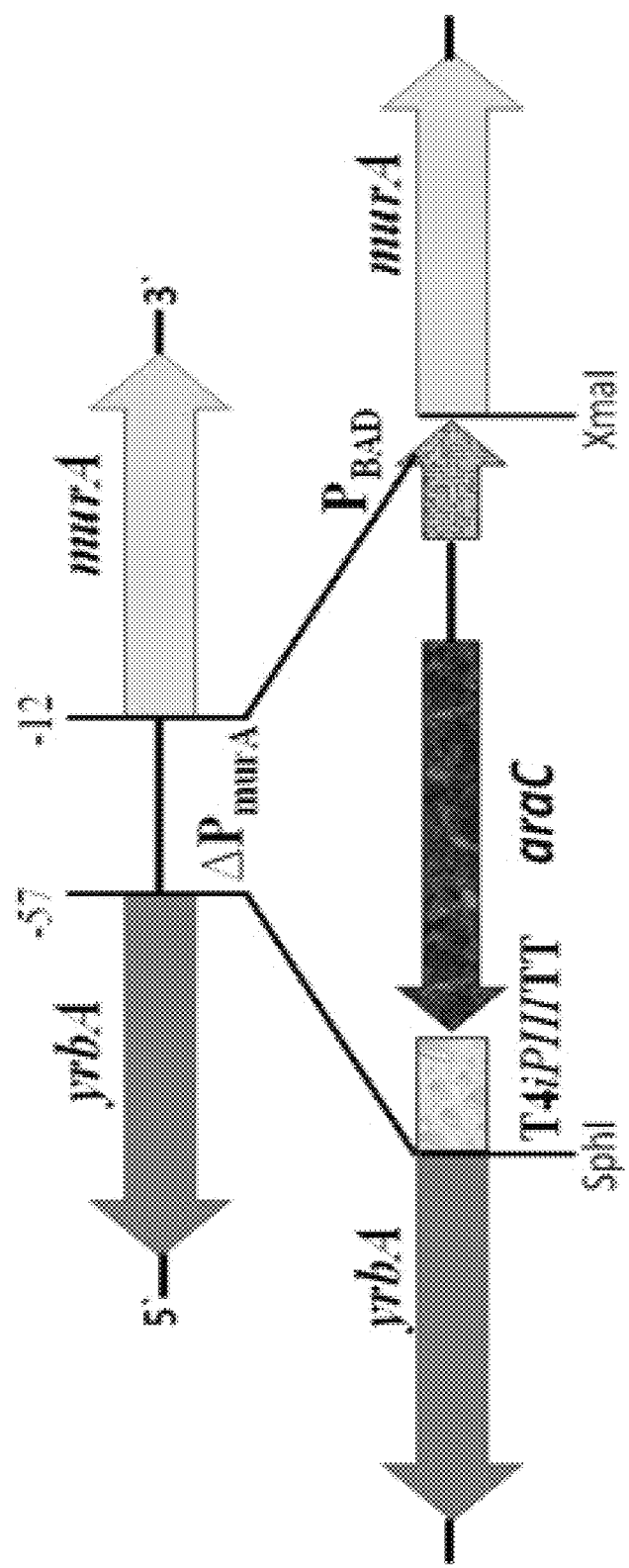

FIGS. 16A-16B: a map showing deletion-insertion mutations resulting in arabinose-regulated murA expression and PCR verification thereof.

Figure 17:
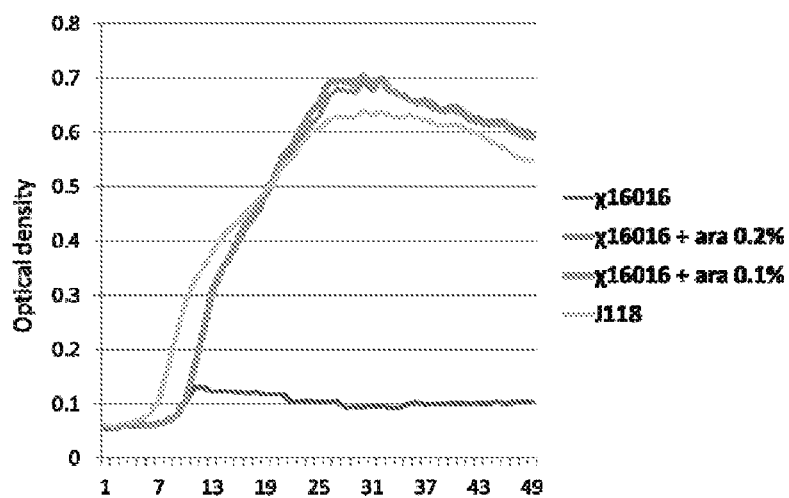

FIG. 17: The growth curves of strain χ16016 with arabinose regulated murA expression in LB broth with or without the addition of 0.2% or 0.1% arabinose.

Figure 18:
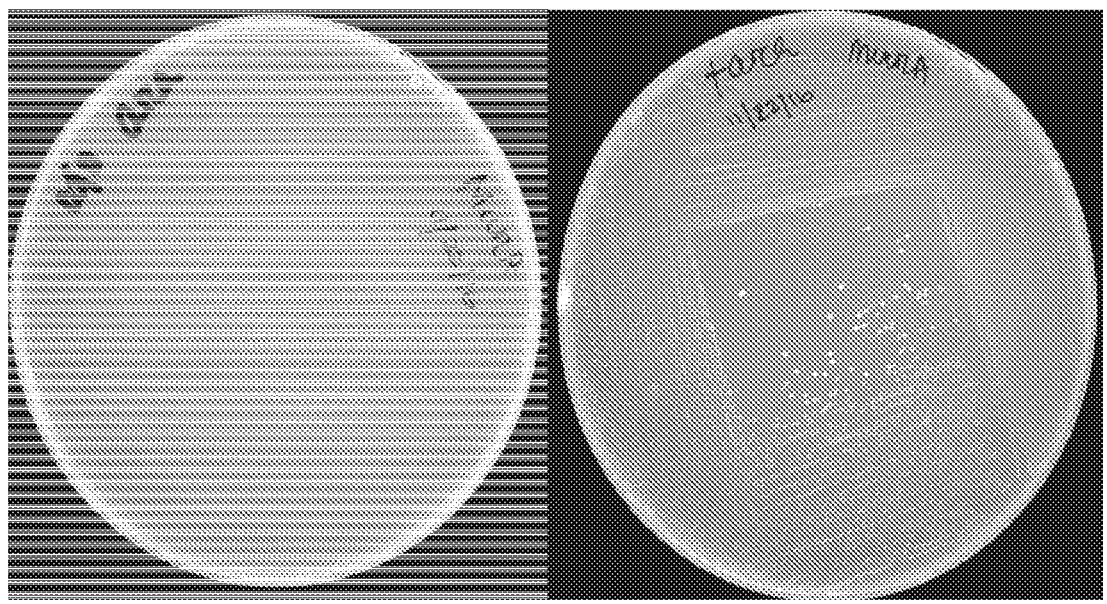

FIG. 18: LB agar plates showing growth of χ$_{16016}$ with or without the addition of arabinose.

Figure 19:
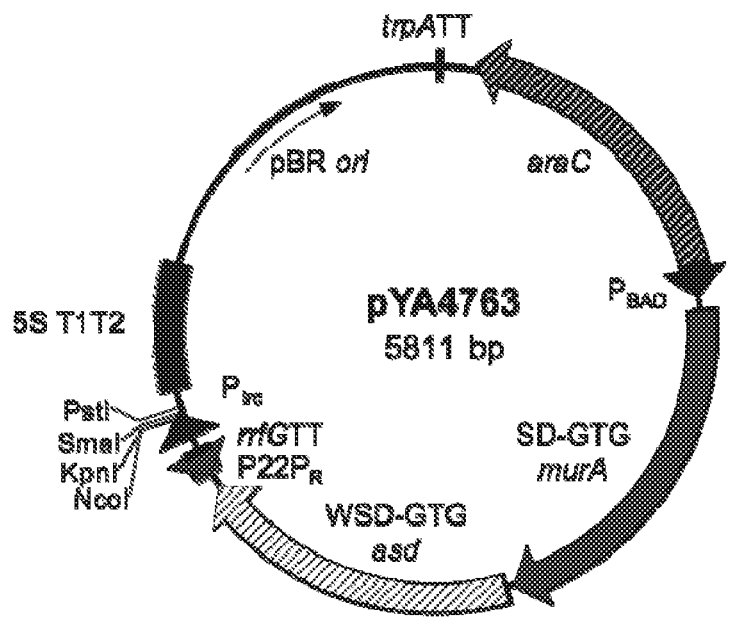

FIG. 19: Map of Lysis vector pYA4763, pBR ori. Plasmid sequences include the araC P$_{araBAD}$ regulated asdA and murA genes.

Figure 20:
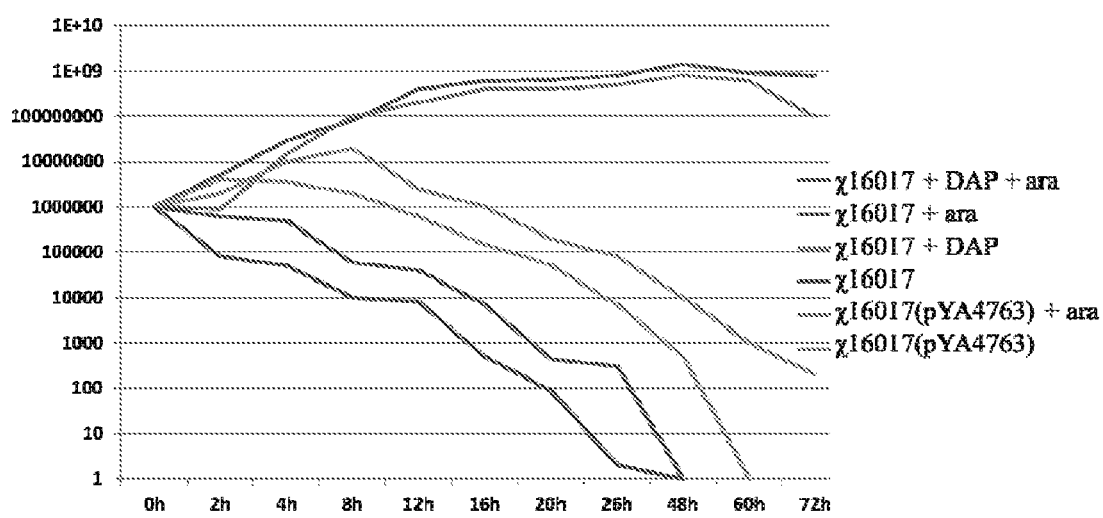

FIG. 20: The growth curves of χ16017 and χ16017 (pYA4763) without or with DAP/arabinose.

Figure 21:
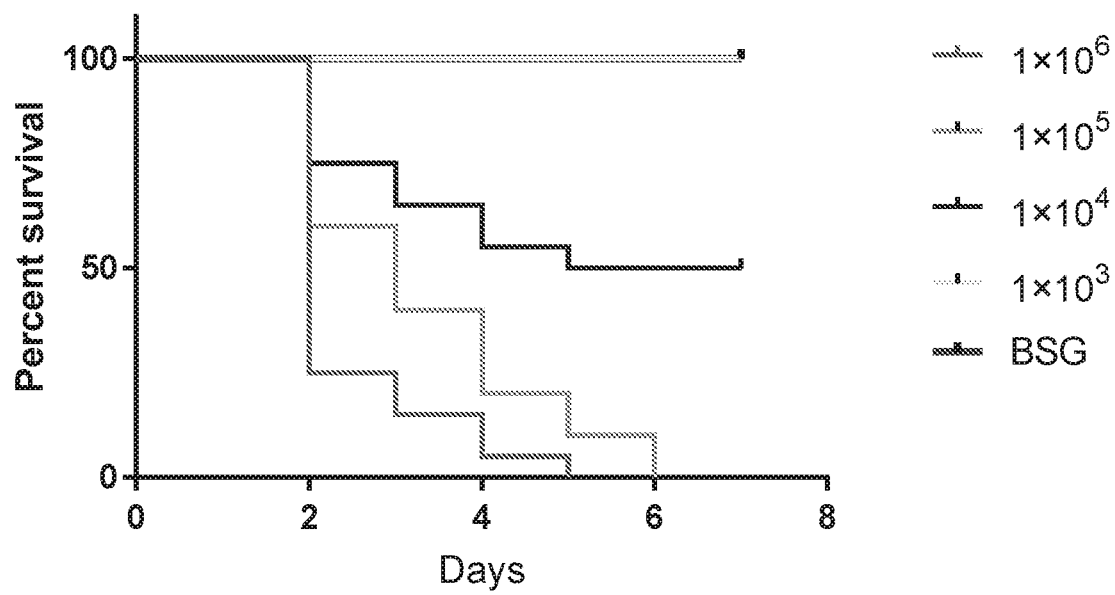

FIG. 21: LD$_{50}$ study of wild-type *Edwardsiella piscicida* (J118) strains by intracelomic (i.c.) injection.

Figure 22:
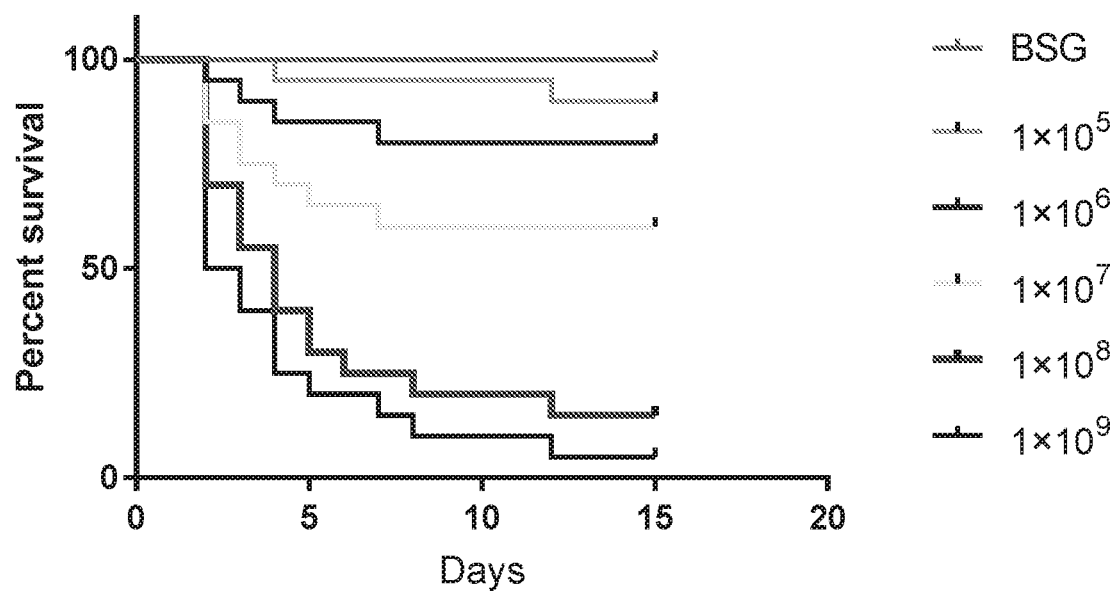

FIG. 22: Determination of LD$_{50}$ of wild-type *Edwardsiella piscicida* (J118) strain by bath immersion.

Figure 23:
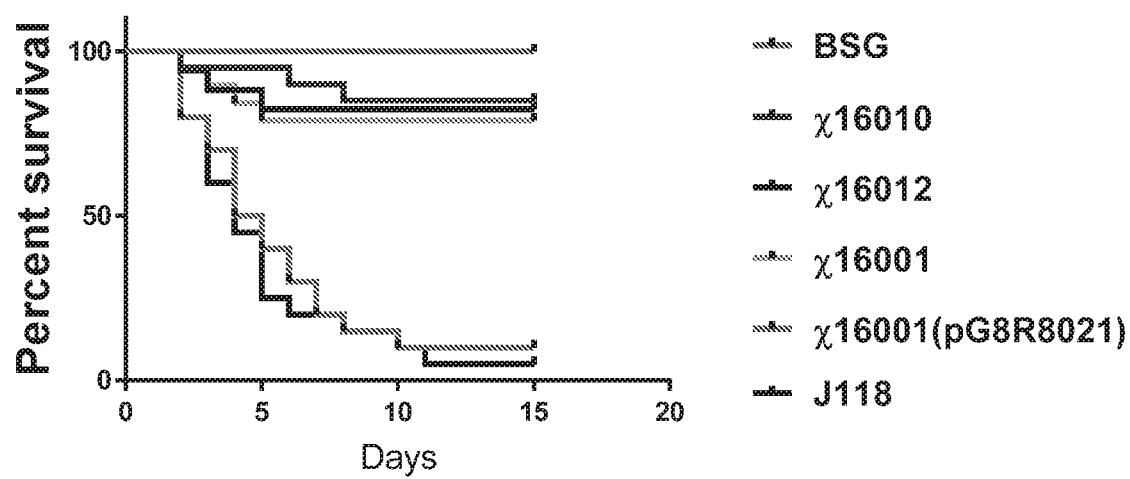

FIG. 23: Virulence of *E. piscicida* Δfur (χ16001), χ16001 (pG8R8021), ΔP$_{fur170}$::TT araC P$_{araBAD}$ fur (χ16001) and ΔP$_{crp68}$::TT araC P$_{araBAD}$ crp (χ16010) in zebrafish host.

DETAILED DESCRIPTION

Disclosed herein is a recombinant attenuated *Edwardsiella* vaccine (RAEV) vector system with regulated delayed attenuation and regulated delayed lysis in vivo attributes that synthesizes two *Ichthyophthirius multifiliis* (Ich) protective antigens to enable vaccination of fresh water fish susceptible to white spot disease. Since *E. piscicida* infects fish living in both fresh water and in marine environments and has a broad host-range, this vaccine vector system has utility in serving as a protective antigen delivery system to prevent a diversity of infectious diseases of multiple fresh water and marine inhabiting species of fish. This vaccine construct, as fully described below, is designed to exhibit the invasive properties of virulent *Edwardsiella* at the time of bath immunization and then is programmed to gradually lose virulence attributes and to synthesize protective antigens as a consequence of in vivo cell division as the RAEV colonizes internal effector lymphoid tissues. The ultimate lysis in vivo delivers a bolus of protective antigen along with immunostimulatory molecules to exhibit complete biological containment with no potential for survival in vivo or ex vivo. These RAEV vector systems thus have the same well-documented safety and efficacy attributes of systems using *Salmonella* vectors. In this regard, these genetically reprogrammed vaccine constructs have solved the problem inherent in the Pasteur approach of generating live bacterial and viral vaccines in which introducing attenuating alterations leads to a concomitant reduction in immunogenicity compared to infection with the wild-type parental pathogen. Thus, the disclosed RAEV constructs with the regulated delayed lysis in vivo attribute induce maximal mucosal, systemic and cellular immune responses against pathogens whose protective antigens are delivered by the vaccine construct.

Ich-Protective Antigens

Disclosed herein are expression plasmid vectors with different copy numbers (one or more) that can be used depending on type of immune response needed. In certain aspects, pBR on vectors can be employed to induce high mucosal and systemic antibody responses.

The disclosed constructs and vaccines can deliver Ich-protective antigens to fish susceptible to this disease. It has been found that constitutive synthesis of protective antigens places a metabolic load on vaccine strains and reduces invasion and immunogenicity. To overcome this issue, constructs and vaccines as disclosed herein exhibit delayed antigen synthesis, in particular regulated delayed antigen synthesis in vivo. Further information and examples relating to delayed antigen synthesis is described in the publication Wang, S., Y. Li, G. Scarpellini, W. Kong, H. Shi, C. Baek, B. Gunn, S. Y. Wanda, K, L. Roland, X. Zhang, P. Senechal-Willis, and R. Curtiss III. 2010. *Salmonella* vaccine vectors displaying delayed antigen synthesis in vivo to enhance immunogenicity. Infect. Immun. 78:3969-3980, which is incorporated by reference in its entirety as fully set forth herein.

The antigens can be i-antigens as i-antigens of Ich parasites are known to induce protective immunity to Ich infections. However, other Ich protective antigens can be employed as would be apparent to one skilled in the art.

These antigens can be encoded by natural or modified genes, such as codon-optimized sequences. Without intending to be limiting, nucleotide sequences that encode antigens can also comprise modifications that alter promoter, SD, spacing, start codons, A-rich codons, and the like. Sequences can be codon optimized to enhance the stability of mRNA to increase levels of antigen synthesis.

In embodiments according to the present disclosure, the antigen is an Ich surface protein, For example, in an embodiment, the antigen can be *Ichthyophthirius multifiliis* immobilization antigen precursor (IAG48). In some embodiments, the antigen can be *Ichthyophthirius multifiliis* immobilization antigen isoform (IAG52A or IAG52B).

Antigen sequences as described herein can also be conservatively modified. For example, antigen sequences can be modified to enhance secretion. Without intending to be limiting, an example of such is by including a β-lactamase signal sequence to facilitate and utilize the type 2 secretion system. Additional examples of modifications can include using T2SSs from secreted proteins such as Lpp, OmpA, and the like. T3SSs can also be employed with several chaperone leaders. Such modifications would be known to the skilled artisan. Examples of embodiments of nucleic acid and amino acid sequences for these antigens are provided below.

IclAG48 (GenBank: AF1402731):

(SEQ ID NO: 1)
ATGAAATATAATATTTTATTAATTTTAATTATTTCTTTATTTATTAATGAATTAAGAG

CTGTTCCATGTCCTGATGGTACTTAGACTCAAGCTGGATTGACTGATGTAGGTGCTG

CTGATCTTGGTACTTGTGTTAATTGCAGACCTAATTTTTACTATAATGGTGGTGCTGCT

-continued

```
TAAGGAGAAGCTAATGGTAATTAACCTTTCGCAGCAAATAATGCTGCTAGAGGTATAT
GTGTACCATGCCAAATAAACAGAGTAGGCTCTGTTACCAATGCAGGTGACTTAGCTA
CTTTAGCCACATAATGCAGTACTTAATGTCCTACTGGCACTGCACTTGATGATGGAGT
GACAGATGTTTTTGATAGATCAGCCGCATAATGTGTTAAATGCAAACCTAACTTTTACT
ATAATGGTGGTTCTCCTTAAGGTGAAGCTCCTGGCGTTTAAGTTTTTGCTGCTGGTG
CTGCCGCTGCAGGTGTTGCTGCCGTTACTAGTTAATGTGTACCTTGCCAACTAAACA
AAAACGATTCTCCTGCCACTGCAGGTGCCTAAGCTAATTTAGCCACATAATGTAGCAA
TTAATGTCCTACTGGCACTGTACTTGATGATGGAGTGACACTTGTTTTTAATACATCAG
CCACATTATGTGTTAAATGCAGACCTAACTTTTACTATAATGGTGGTTCTCCTTAAGGT
GAAGCTCCTGGCGTTTAAGTTTTTGCTGCTGGTGCTGCCGCTGCAGGTGTTGCTGC
CGTTACTAGTTAATGTGTACCTTGCCAAATAAACAAAAACGATTCTCCTGCCACTGCA
GGTGCCTAAGCTAATTTAGCCACATAATGCAGTACTTAATGTCCAACTGGCACTGCAA
TTCAAGACGGAGTGACACTTGTTTTTAGTAATTCATCCACATAATGTTCTTAATGCATT
GCTAATTACTTTTTTAATGGTAATTTCGAAGCAGGTAAAAGTTAATGTTTAAAGTGTCC
AGTAAGTAAAACTACTCCAGCACATGCTCCAGGTAATACTGCTACTTAAGCCACATAA
TGTTTGACCACATGTCCTGCTGGTACAGTACTTGATGATGGAACATCAACTAATTTTG
TAGCTTCCGCAACTGAATGTACTAAATGTTCTGCTGGCTTTTTTGCATCAAAAACAAC
TGGTTTTACAGCAGGTACTGATACATGTACTGAATGTACTAAAAAATTAACTTCTGGTG
CCACAGCTAAAGTATATGCTGAAGCTACTCAAAAAGTATAATGCGCCTCCACTACTTT
CGCTAAATTTTTATCGATTTCCTTATTATTTATTTCTTTCTATTTATTGTGA.
                                                   (SEQ ID NO: 2)
MKYNILLILIISLFINELRAVPCPDGTQTQAGLTDVGAADLGTCVNCRPNFYYNGG
AAQGEANGNQPFAANNAARGICVPCQINRVGSVTNAGDLATLATQCSTQCPTGTALDD
GVTDVFDRSAAQCVKCKPNFYYNGGSPQGEAPGVQVFAAGAAAAGVAAVTSQCVPC
QLNKNDSPATAGAQANLATQCSNQCPTGTVLDDGVTLVFNTSATLCVKCRPNFYYNGG
SPQGEAPGVQVFAAGAAAAGVAAVTSQCVPCQINKDSPATAGAQANLATQCSTQCPT
GTAIQDGVTLVFSNSSTQCSQCIANYFFNGNFEAGKSQCLKCPVSKTTPAHAPGNTATQ
ATQCLTTCPAGTVLDDGTSTNFVASATECTKCSAGFFASKTTGFTAGTDTCTECTKKLTS
GATAKVYAEATQKVQCASTTFAKFLSISLLFISFYLL.
IAG48 (TAA and TAG codons changed to CAG (* to Q)):
                                                   (SEQ ID NO: 3)
ATGAAATATAATATTTTATTAATTTTAATTATTTCTTTATTTATTAATGAATTAAGAG
CTGTTCCATGTCCTGATGGTACTCAGACTCAAGCTGGATTGACTGATGTAGGTGCTG
CTGATCTTGGTACTTGTGTTAATTGCAGACCTAATTTTTACTATAATGGTGGTGCTGCT
CAGGGAGAAGCTAATGGTAATCAGCCTTTCGCAGCAAATAATGCTGCTAGAGGTATAT
GTGTACCATGCCAAATAAACAGAGTAGGCTCTGTTACCAATGCAGGTGACTTAGCTA
CTTTAGCCACACAGTGCAGTACTCAGTGTCCTACTGGCACTGCACTTGATGATGGAG
TGACAGATGTTTTTGATAGATCAGCCGCACAGTGTGTTAAATGCAAACCTAACTTTTA
CTATAATGGTGGTTCTCCTCAGGGTGAAGCTCCTGGCGTTCAGGTTTTTGCTGCTGG
TGCTGCCGCTGCAGGTGTTGCTGCCGTTACTAGTCAGTGTACCTTGCCAACTAAA
CAAAAACGATTCTCCTGCCACTGCAGGTGCCCAGGCTAATTTAGCCACACAGTGTAG
CAATCAGTGTCCTACTGGCACTGTACTTGATGATGGAGTGACACTTGTTTTTAATACA
```

-continued

```
TCAGCCACATTATGTGTTAAATGCAGACCTAACTTTTACTATAATGGTGGTTCTCCTCA

GGGTGAAGCTCCTGGCGTTCAGGTTTTTGCTGCTGGTGCTGCCGCTGCAGGTGTT

GCTGCCGTTACTAGTCAGTGTGTACCTTGCCAAATAAACAAAAACGATTCTCCTGCC

ACTGCAGGTGCCCAGGCTAATTTAGCCACACAGTGCAGTACTCAGTGTCCAACTGG

CACTGCAATTCAAGACGGAGTGACACTTGTTTTTAGTAATTCATCCACACAGTGTTCT

CAGTGCATTGCTAATTACTTTTTTAATGGTAATTTCGAAGCAGGTAAAAGTCAGTGTTT

AAAGTGTCCAGTAAGTAAAACTACTCCAGCACATGCTCCAGGTAATACTGCTACTCA

GGCCACACAGTGTTTGACCACATGTCCTGCTGGTACAGTACTTGATGATGGAACATC

AACTAATTTTGTAGCTTCCGCAACTGAATGTACTAAATGTTCTGCTGGCTTTTTTGCAT

CAAAAACAACTGGTTTTACAGCAGGTACTGATACATGTACTGAATGTACTAAAAAATTA

ACTTCTGGTGCCACAGCTAAAGTATATGCTGAAGCTACTCAAAAAGTACAGTGCGCC

TCCACTACTTTCGCTAAATTTTTATCGATTTCCTTATTATTTATTTCTTTCTATTTATTGTG

A.
```

(SEQ ID NO: 4)
```
MKYNILLILIISLFINELRAVPCPDGTQTQAGLTDVGAADLGTCVNCRPNFYYNG

GAAQGEANGNQPFAANNAARGICVPCQINRVGSVTNAGDLATLATQCSTQCPTGTAL

DDGVTDVFDRSAAQCVKCKPNFYYNGGSPQGEAPGVQVFAAGAAAAGVAAVTSQCV

PCQLNKNDSPATAGAQANLATQCSNQCPTGTVLDDGVTLVFNTSATLCVKCRPNFYY

NGGSPQGEAPGVQVFAAGAAAAGVAAVTSQCVPCQINKNDSPATAGAQANLATQCST

QCPTGTAIQDGVTLVFSNSSTQCSQCIANYFFNGNFEAGKSQCLKCPVSKTTPAHAPG

NTATQATQCLTTCPAGTVLDDGTSTNFVASATECTKCSAGFFASKTTGFTAGTDTCTE

CTKKLTSGATAKVYAEATQKVQCASTTFAKFLSISLLFISFYLL.
```

IAG48 (Codon optimized sequence):

(SEQ ID NO: 5)
```
ATGAAGTACAACATACTGTTAATACTTATCATTTCGCTTTTCATAAATGAGCTTA

GAGCAGTGCCCTGCCCCGATGGAACACAAACACAGGCCGGATTGACAGACGTTGG

GGCAGCCGATCTGGGGACTTGTGTCAACTGTCGGCCGAATTTTTATTATAACGGAGG

CGCAGCGCAGGGTGAGGCGAACGGCAATCAGCCCTTTGCGGCGAACAATGCAGC

GAGAGGCATCTGTGTTCCTTGTCAAATCAACCGTGTAGGCAGCGTAACAAACGCCG

GGGATCTTGCCACCCTGGCCACACAGTGTAGCACACAATGCCCTACGGGGACCGC

ATTGGATGATGGGGTTACCGACGTTTTTGATAGATCTGCAGCTCAGTGCGTAAAGTG

TAAACCGAACTTCTATTATAACGGTGGTTCTCCACAGGGCGAGGCCCCCGGGGTAC

AAGTGTTTGCGGCTGGTGCAGCCGCTGCTGGAGTCGCCGCCGTAACATCCCAATG

TGTGCCCTGCCAACTGAACAAGAACGACAGTCCTGCTACGGCCGGAGCCCAGGCA

AACCTGGCTACGCAATGTTCCAATCAATGCCCTACTGGGACCGTGTTGGACGATGG

GGTAACATTGGTTTTCAATACGTCAGCAACTCTGTGCGTTAAATGTCGTCCCAATTTC

TACTATAACGGAGGTAGCCCTCAGGGAGAAGCCCCGGGGGTCCAGGTCTTCGCTG

CAGGTGCCGCAGCTGCGGGGTGGCCGCAGTTACATCGCAATGCGTACCGTGCCA

GATCAACAAAAATGATAGCCCGGCGACAGCAGGGGCTCAAGCGAATCTTGCAACCC

AATGCTCTACTCAATGCCCGACCGGTACAGCTATCCAAGACGGAGTGACCCTGGTTT

TTTCTAATTCCTCGACACAGTGTTCACAGTGCATCGCTAATTACTTTTTAACGGGAAT

TTTGAGGCAGGGAAGTCGCAATGTTTAAAATGTCCTGTGAGTAAAACGACTCCCGCA
```

-continued

```
CATGCCCCTGGGAACACAGCTACGCAGGCAACCCAATGCCTGACGACGTGTCCGG

CAGGTACCGTCCTGGACGATGGGACTTCTACAAATTTTGTAGCCTCCGCGACTGAAT

GTACAAAGTGCAGCGCGGGTTTTTTCGCTAGCAAAACGACGGGGTTCACGGCAGG

AACAGATACTTGCACGGAATGTACGAAAAAATTAACGAGTGGCGCGACGGCGAAGG

TTTACGCAGAGGCGACTCAGAAAGTACAATGTGCATCTACAACATTCGCAAAGTTCC

TTTCCATCTCCTTGCTGTTTATTTCGTTCTACCTGCTGTGA.
```

(SEQ ID NO: 6)
```
MKYNILLILIISLFINELRAVPCPDGTTQAGLTDVGAADLGTCVNCRPNFYYNGGA

AGEANGNPFAANNAARGICVPCQINRVGSVTNAGDLATLATCSTCPTGTALDDGVTDVF

DRSAACVKCKPNFYYNGGSPGEAPGVVFAAGAAAAGVAAVTSCVPCQLNKNDSPATA

GAANLATCSNCPTGTVLDDGVTLVFNTSATLCVKCRPNFYYNGGSPGEAPGVVFAAGA

AAAGVAAVTSCVPCQINKNDSPATAGAANLATCSTCPTGTAIQDGVTLVFSNSSTCSCIA

NYFFNGNFEAGKSCLKCPVSKTTPAHAPGNTATATCLTTCPAGTVLDDGTSTNFVASAT

ECTKCSAGFFASKTTGFTAGTDTCTECTKKLTSGATAKVYAEATQKVCASTTFAKFLSIS

LLFISFYLL.
```

IAG52A (GenBank:AF324424.1)

(SEQ ID NO: 7)
```
ATGAAAAATAATATTTTAGTAATATTGATTATTTCATTATTTATCAATTAAATTAAAT

CTGCTAATTGTCCTGTTGGAACTGAAACTAACACAGCCGGATAAGTTGATGATCTAG

GAACTCCTGCAAATTGTGTTAATTGTTAGAAAAACTTTTATTATAATAATGCTGCTGCTT

TCGTTCCTGGTGCTAGTACGTGTACACCTTGTCCATAAAAAAAAGATGCTGGTGCTTA

ACCAAATCCACCTGCTACTGCTAATTTAGTCACATAATGTAACGTTAAATGCCCTGCT

GGTACCGCAATTGCAGGTGGAGCAACAGATTATGCAGCAATAATCACAGAATGTGTT

AATTGTAGAATTAATTTTTATAATGAAAATGCTCCAAATTTTAATGCAGGTGCTAGTACA

TGCACAGCTTGTCCGGTAAACAGAGTTGGTGGTGCATTGACTGCTGGTAATGCCGC

TACCATAGTCGCATAATGTAACGTCGCATGTCCTACTGGTACTGCACTTGATGATGGA

GTAACTACTGATTATGTTAGATCATTCACAGAATGTGTTAAATGTAGACTTAACTTTTAC

TATAATGGTAATAATGGTAATACTCCTTTCAATCCAGGTAAAAGTTAATGCACACCTTG

TCCGGCAATTAAACCTGCTAATGTTGCTTAAGCTACTTTAGGTAATGATGCTACAATAA

CCGCATAATGTAACGTTGCATGCCCTGATGGTACTATAAGTGCTGCTGGAGTAAATAA

TTGGGTAGCACAAAACACTGAATGTACTAATTGTGCTCCTAACTTTTACAATAATAATG

CTCCTAATTTCAATCCAGGTAATAGTACATGCCTACCTTGCCCAGCAAATAAAGATTAT

GGTGCTGAAGCCACTGCAGGTGGTGCCGCTACTTTAGCCAAATAATGTAATATTGCA

TGCCCTGATGGTACTGCAATTGCTAGTGGAGCAACTAATTATGTAATATTATAAACAGA

ATGTCTAAATTGTGCTGCTAACTTTTATTTTGATGGTAATAATTTCTAGGCAGGAAGTA

GTAGATGCAAAGCATGTCCAGCAAATAAAGTTTAAGGCGCTGTAGCAACTGCAGGTG

GTACTGCTACTTTAATTGCATAATGTGCCCTTGAATGCCCTGCTGGTACTGTACTCAC

CGATGGAACAACATCTACTTATAAATAAGCAGCATCTGAATGTGTTAAATGTGCTGCC

AACTTTTATACTACAAAATAAACTGATTGGGTAGCAGGTATTGATACATGTACTAGTTGT

AATAAAAAATTAACTTCTGGCGCTGAAGCTAATTTACCTGAATCTGCTAAAAAAATAT

ATAATGTGATTTCGCTAATTTTTTATCAATTTCCTTATTATTGATTTCTTATTATTTATTATG

A.
```

-continued (SEQ ID NO: 8)
MKNNILVILIISLFINQIKSANCPVGTETNTAGQVDDLGTPANCVNCQKNFYYNNA

AAFVPGASTCTPCPQKKDAGAQPNPPATANLVTQCNVKCPAGTAIAGGATDYAAIITECV

NCRINFYNENAPNFNAGASTCTACPVNRVGGALTAGNAATIVAQCNVACPTGTALDDGV

TTDYVRSFTECVKCRLNFYYNGNNGNTPFNPGKSQCTPCPAIKPANVAQATLGNDATIT

AQCNVACPDGTISAAGVNNWVAQNTECTNCAPNFYNNNAPNFNPGNSTCLPCPANKD

YGAEATAGGAATLAKQCNIACPDGTAIASGATNYVILQTECLNCAANFYFDGNNFQAGS

SRCKACPANKVQGAVATAGGTATLIAQCALECPAGTVLTDGTTSTYKQAASECVKCAAN

FYTTKQTDWVAGIDTCTSCNKKLTSGAEANLPESAKKNIQCDFANFLSISLLLISYYLL.

IAG52A (TAA and TAG codons changed to CAG (* to Q))

(SEQ ID NO: 9)
ATGAAAAATAATATTTTAGTAATATTGATTATTTCATTATTTATCAATCAGATTA

AATCTGCTAATTGTCCTGTTGGAACTGAAACTAACACAGCCGGACAGGTTGATGAT

CTAGGAACTCCTGCAAATTGTGTTAATTGTCAGAAAAACTTTTATTATAATAATGCTG

CTGCTTTCGTTCCTGGTGCTAGTACGTGTACACCTTGTCCACAGAAAAAAGATGCT

GGTGCTCAGCCAAATCCACCTGCTACTGCTAATTTAGTCACACAGTGTAACGTTAAA

TGCCCTGCTGGTACCGCAATTGCAGGTGGAGCAACAGATTATGCAGCAATAATCAC

AGAATGTGTTAATTGTAGAATTAATTTTTATAATGAAAATGCTCCAAATTTTAATGCA

GGTGCTAGTACATGCACAGCTTGTCCGGTAAACAGAGTTGGTGGTGCATTGACTGC

TGGTAATGCCGCTACCATAGTCGCACAGTGTAACGTCGCATGTCCTACTGGTACTG

CACTTGATGATGGAGTAACTACTGATTATGTTAGATCATTCACAGAATGTGTTAAAT

GTAGACTTAACTTTTACTATAATGGTAATAATGGTAATACTCCTTTCAATCCAGGTAA

AAGTCAGTGCACACCTTGTCCGGCAATTAAACCTGCTAATGTTGCTCAGGCTACTTT

AGGTAATGATGCTACAATAACCGCACAGTGTAACGTTGCATGCCCTGATGGTACTA

TAAGTGCTGCTGGAGTAAATAATTGGGTAGCACAAAACACTGAATGTACTAATTGTG

CTCCTAACTTTTACAATAATAATGCTCCTAATTTCAATCCAGGTAATAGTACATGCCT

ACCTTGCCCAGCAAATAAAGATTATGGTGCTGAAGCCACTGCAGGTGGTGCCGCTA

CTTTAGCCAAACAGTGTAATATTGCATGCCCTGATGGTACTGCAATTGCTAGTGGAG

CAACTAATTATGTAATATTACAGACAGAATGTCTAAATTGTGCTGCTAACTTTTATTTT

GATGGTAATAATTTCCAGGCAGGAAGTAGTAGATGCAAAGCATGTCCAGCAAATAA

AGTTCAGGGCGCTGTAGCAACTGCAGGTGGTACTGCTACTTTAATTGCACAGTGTG

CCCTTGAATGCCCTGCTGGTACTGTACTCACCGATGGAACAACATCTACTTATAAAC

AGGCAGCATCTGAATGTGTTAAATGTGCTGCCAACTTTTATACTACAAAACAGACTG

ATTGGGTAGCAGGTATTGATACATGTACTAGTTGTAATAAAAAATTAACTTCTGGCG

CTGAAGCTAATTTACCTGAATCTGCTAAAAAAAATATACAGTGTGATTTCGCTAATTT

TTTATCAATTTCCTTATTATTGATTTCTTATTATTTATTATGA.

(SEQ ID NO: 10)
MKNNILVILIISLFINQIKSANCPVGTETNTAGQVDDLGTPANCVNCQKNFYYNNA

AAFVPGASTCTPCPQKKDAGAQPNPPATANLVTQCNVKCPAGTAIAGGATDYAAIITEC

VNCRINFYNENAPNFNAGASTCTACPVNRVGGALTAGNAATIVAQCNVACPTGTALDD

GVTTDYVRSFTECVKCRLNFYYNGNNGNTPFNPGKSQCTPCPAIKPANVAQATLGNDA

TITAQCNVACPDGTISAAGVNNWVAQNTECTNCAPNFYNNNAPNFNPGNSTCLPCPA

NKDYGAEATAGGAATLAKQCNIACPDGTAIASGATNYVILQTECLNCAANFYFDGNNFQ

-continued

AGSSRCKACPANKVQGAVATAGGTATLIAQCALECPAGTVLTDGTTSTYKQAASECVK

CAANFYTTKQTDWVAGIDTCTSCNKKLTSGAEANLPESAKKNIQCDFANFLSISLLLISY

YLL.

IAG52A (Codon Optimized Sequence):

(SEQ ID NO: 11)
ATGAAGAACAACATATTAGTCATCCTGATAATCTCGTTATTCATTAATCAGAT

CAAAAGTGCGAATTGTCCAGTTGGAACGGAGACGAACACAGCCGGGCAGGTGGAT

GATTTAGGCACGCCCGCAAATTGTGTAAACTGCCAAAAGAATTTCTACTATAACAAC

GCGGCAGCATTCGTTCCAGGGGCGTCAACTTGTACGCCTTGTCCCCAAAAGAAGG

ATGCTGGCGCTCAGCCCAATCCACCCGCCACGGCAAATTTGGTAACCCAATGTAAT

GTAAAATGTCCCGCCGGGACAGCGATAGCGGGAGGAGCAACCGACTACGCAGCC

ATCATAACAGAATGCGTCAACTGCCGCATTAATTTCTATAATGAGAACGCGCCCAAT

TTCAATGCAGGGGCCAGTACCTGTACTGCTTGCCCAGTAAACCGGGTGGGCGGGG

CGCTTACGGCAGGGAACGCCGCCACGATTGTGGCACAGTGTAACGTAGCATGTCC

AACGGGTACTGCCCTTGATGACGGCGTGACAACCGACTATGTGAGATCGTTTACCG

AGTGTGTGAAATGCAGATTGAACTTCTACTACAACGGGAACAATGGAAATACGCCG

TTTAATCCGGGTAAAAGCCAATGCACTCCTTGCCCTGCCATAAAGCCAGCCAATGT

GGCACAAGCGACTCTTGGTAACGACGCCACAATCACAGCTCAGTGCAATGTAGCGT

GCCCCGATGGTACCATCTCAGCTGCAGGTGTTAATAATTGGGTGGCACAAAACACT

GAGTGCACCAACTGTGCGCCGAACTTCTACAATAACAACGCTCCGAATTTTAATCC

GGGAAATTCTACGTGCCTTCCATGTCCTGCTAACAAGGATTATGGCGCCGAGGCTA

CAGCTGGCGGGGCCGCGACGTTGGCCAAACAATGCAATATTGCATGCCCCGATGG

CACGGCAATAGCTAGTGGGCAACGAATTATGTGATTTTACAGACAGAGTGTCTTA

ACTGCGCGGCTAATTTTTATTTCGATGGCAACAACTTCCAGGCTGGTAGCTCGCGC

TGTAAGGCATGTCCAGCTAACAAGGTTCAGGGGGCAGTTGCAACCGCAGGAGGAA

CCGCTACTCTTATTGCCCAATGTGCCTTAGAATGTCCTGCTGGCACAGTATTGACTG

ATGGGACGACATCAACCTATAAGCAGGCGGCGAGTGAATGTGTGAAATGTGCTGC

GAACTTCTACACTACAAAACAAACTGACTGGGTCGCGGGTATTGACACCTGCACCT

CATGTAATAAGAAGTTAACTTCCGGGGCTGAAGCTAACTTACCAGAATCGGCTAAG

AAAAATATTCAATGCGACTTCGCTAACTTCTTAAGTATAAGTCTGCTTTTGATTTCTT

ATTATCTGCTTTGA.

(SEQ ID NO: 12)
MKNNILVILIISLFINIKSANCPVGTETNTAGVDDLGTPANCVNCKNFYYNNAAAF

VPGASTCTPCPKKDAGAPNPRATANLVTCNVKCPAGTAIAGGATDYAAIITECVNCRINF

YNENAPNFNAGASTCTACPVNRVGGALTAGNAATIVACNVACPTGTALDDGVTTDYVR

SFTECVKCRLNFYYNGNNGNTPFNPGKSCTPCPAIKPANVAATLGNDATITACNVACP

DGTISAAGVNNWVAQNTECTNCAPNFYNNNAPNFNPGNSTCLPCPANKDYGAEATAG

GAATLAKCNIACPDGTAIASGATNYVILTECLNCAANFYFDGNNFAGSSRCKACPANKV

GAVATAGGTATLIACALECPAGTVLTDGTTSTYKAASECVKCAANFYTTKTDWVAGIDT

CTSCNKKLTSGAEANLPESAKKNICDFANFLSISLLLISYYLL.

IAG52B (SEQ ID NO: 13)

ATGGTGAATTGCCCGAATGGCGCCGCCATCGCCAATGGCCAGAGCGATAC

CGGCGCCGCCGATATCAATACCTGCACCCATTGCCAGAAACATTTTTATTTTAATGG

CGGCAATCCGGCCGGCCAGGCCCCGGGCGCCGTGCAGTTTAATCCGGGCGTGAG

CCAGTGCATCGCCTGCCAGGTGCATAAAGCCGATAGCCAGCATCGCCAGGGCGGC

GATGCCAATCTGGCCGCCCAGTGCAGCAATCTGTGCCCGGCCGGCACCGCCGTG

GAGGATGGCAGCCCGACCTTTACCCAGAGCCTGACCCAGTGCGTGAATTGCAAAC

CGAATTTTTATTTTAATGGCGGCAATCCGACCGGCCAGGCCCCGGGCGCCGGCCA

GTTTGATCCGACCCAGCTGATCGCCAATCCGGATCTGGCCAATAATCCGGAGGTG

CCGAATGTGAGCAGCCCGAATGGCCAGTGCGTGGCCTGCCAGGTGAATAAAAGCG

ATAGCCAGCTGCGCCCGGGCGCCCAGGCCAATCTGGCCACCCAGTGCAATAATGA

GTGCCCGACCGGCACCGCCATCCAGGATGGCGCCATCTTTATCTATACCCAGAGC

ATCAGCCAGTGCACCTTTTGCAAAGTGGATTTTTATTTTAATGGCGGCAATCCGAGC

GCCCAGAATCCGGGCAATGGCCAGTTTACCCCGGGCCAGCTGATCGCCAATCCGG

ATGCCGCCACCGCCGCCCAGATCCCGATGGTGCCGGGCCCGAATAGCAAATGCGT

GGCCTGCGAGAGCAAAAAAACCAATAGCCAGAGCCGCAGCGGCCTGGAGGCCAAT

CTGGCCGCCCAGTGCGGCACCGAGTGCCCGGCCGGCACCCTGGTGACCGATGGC

GTGACCCCGACCTATACCGTGAGCCTGAGCCAGTGCGTGAATTGCAAAGCCGGCT

TTTATCAGAATAGCAATTTTGAGGCCGGCAAAAGCCAGTGCAATAAATGCGCCGTG

AGCAAAACCGGCAGCGCCAGCGTGCCGGGCAATAGCGCCACCAGCGCCACCCAG

TGCCAGAATGATTGCCCGGCCGGCACCGTGGTGGATGATGGCAGCACCAATTTTG

TGGCCCTGGCCAGCGAGTGCACCAAATGCCAGGCCAATTTTATGCCAGCAAAACC

AGCGGCTTTGCCGCCGGCACCGATACCTGCACCGAGTGCAGCAAAAAACTGACCA

GCGGCGCCACCGCCAAAGTGTATGCCGAGGCCACCCAGAAAGCCCAGTGCGCCA

GCTGA.

(SEQ ID NO: 14)
MVNCPNGAAIANGQSDTGAADINTCTHCQKHFYFNGGNPAGQAPGAVQFNPG

VSQCIACQVHKADSQHRQGGDANLAAQCSNLCPAGTAVEDGSPTFTQSLTQCVNCKP

NFYFNGGNPTGQAPGAGQFDPTQLIANPDLANNPEVPNVSSPNGQCVACQVNKSDSQ

LRPGAQANLATQCNNECPTGTAIQDGAIFIYTQSISQCTFCKVDFYFNGGNPSAQNPGN

GQFTPGQLIANPDAATAAQIPMVPGPNSKCVACESKKTNSQSRSGLEANLAAQCGTEC

PAGTLVTDGVTPTYTVSLSQCVNCKAGFYQNSNFEAGKSQCNKCAVSKTGSASVPGN

SATSATQCQNDCPAGTVVDDGTSTNFVALASECTKCCANFYASKTSGFAAGTDTCTE

CSKKLTSGATAKVYAEATQKAQCAS.

IAG52B (Codon Optimized)

(SEQ ID NO: 15)
GTTAATTGTCCTAATGGTGCTGCAATTGCGAATGGATAATCTGATACAGGAG

CTGCAGATATAAATACTTGTACTCATTGCTAAAAACACTTTTACTTTAATGGTGGTAA

TCCTGCAGGTCAGGCTCCTGGTGCTGTACAATTCAATCCAGGTGTTAGTCAGTGCA

TAGCTTGCCAAGTACACAAAGCCGATTCTCAACACAGATAAGGTGGTGATGCTAATT

TAGCCGCATAATGTAGCAACTTATGTCCTGCTGGCACTGCAGTTGAAGATGGATCA

CCTACTTTTACTTAATCCCTCACATAATGTGTTAATTGTAAACCTAACTTTTACTTTAA

-continued
```
TGGTGGTAATCCTACAGGTCAGGCTCCTGGTGCTGGATAATTCGATCCAACTTAATT

GATTGCAAATCCTGATCTTGCTAATAATCCTGAAGTTCCTAATGTTTCTAGCCCTAAT

GGTTAATGCGTAGCTTGCTAAGTAAACAAGTCTGATTCTCAATTAAGACCAGGTGCT

TAGGCTAATTTAGCCACATAATGTAACAATGAATGTCCTACTGGCACTGCTATTCAA

GACGGAGCAATATTTATTTATACTTAATCAATCTCATAATGTACTTTTTGTAAAGTTG

ACTTTTACTTTAATGGTGGCAATCCTTCAGCTCAGAATCCTGGTAATGGATAATTCA

CTCCAGGTTAATTGATTGCAAATCCTGATGCTGCTACTGCTGCTTAAATTCCTATGG

TTCCTGGCCCTAATAGTAAATGCGTAGCTTGCGAATCAAAAAAGACCAATTCTTAAT

CCAGATCAGGTCTTGAGGCTAATTTAGCCGCATAATGTGGCACTGAATGTCCTGCT

GGCACTCTTGTTACAGACGGAGTAACACCTACTTATACTGTATCACTCTCATAATGT

GTTAATTGTAAAGCTGGCTTTTACTAAAATAGTAATTTCGAAGCAGGTAAAAGTTAAT

GCAATAAGTGTGCAGTAAGTAAAACTGGTTCAGCATCTGTTCCAGGTAATAGTGCTA

CTTCAGCCACATAATGTTAAAACGATTGCCCTGCTGGTACAGTGGTTGATGATGGTA

CATCAACTAATTTTGTAGCTTTAGCAAGTGAATGTACTAAATGTTAGGCTAACTTTTA

TGCATCAAAAACATCTGGTTTTGCAGCAGGTACTGATACATGTACTGAATGTTCTAA

AAAATTAACTTCTGGTGCTACAGCTAAAGTATATGCTGAAGCTACTTAAAAAGCATA

ATGCGCCAGT.

(SEQ ID NO: 16)
VNCPNGAAIANGSDTGAADINTCTHCKHFYFNGGNPAGQAPGAVQFNPGVSQ

CIACQVHKADSQHRGGDANLAACSNLCPAGTAVEDGSPTFTSLTCVNCKPNFYFNGGN

PTGQAPGAGFDPTLIANPDLANNPEVPNVSSPNGCVACVNKSDSQLRPGAANLATCNN

ECPTGTAIQDGAIFIYTSISCTFCKVDFYFNGGNPSAQNPGNGFTPGLIANPDAATAAIPM

VPGPNSKCVACESKKTNSSRSGLEANLAACGTECPAGTLVTDGVTPTYTVSLSCVNCK

AGFYNSNFEAGKSCNKCAVSKTGSASVPGNSATSATCNDCPAGTVVDDGTSTNFVALA

SECTKCANFYASKTSGFAAGTDTCTECSKKLTSGATAKVYAEATKACAS.
```

As used herein, "antigen" refers to a biomolecule capable of eliciting an immune response in a host. In some embodiments, the antigen may be a protein, or fragment of a protein, or a nucleic acid. Therefore, the antigen can be an immunogenic fragment of a protein disclosed herein.

In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from *Ichthyophthirius multifiliis* may induce an immune response that helps to ameliorate symptoms associated with *Ichthyophthirius multifiliis* infection or reduce the morbidity and mortality associated with infection with the pathogen. The use of the term "protective" in this invention does not necessarily require that the host is completely protected from the effects of the pathogen.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

Additionally, the vectors may be designed for various types of antigen delivery systems. The system that is selected will depend, in part, on the immune response desired. For example, if an antibody response is desired, then a Type II secretion system may be used. Examples of Type II secretion systems are well-known in the art. Alternatively, if a cytotoxic T lymphocyte (CTL) response is desired, then a Type III secretion system may be used. Type III secretion systems are known in the art. This type of antigen delivery system delivers the antigen to the cytoplasm of cells in the host to enhance induction of CTL responses. Yet another type of antigen delivery strategy that may be used is regulated delayed lysis of a bacterium in vivo to release protein antigen(s) and/or viral proteins. The viral proteins may include viral core particles with or without epitope fusion. Regulated antigen delivery systems are known in the art. See, for example, U.S. Pat. No. 6,780,405, hereby incorporated by reference in its entirety. In other embodiments, the antigen may be delivered to the cytosol of a host cell by lysis of the recombinant bacterium. Such lysis may be regulated as described herein.

Furthermore, antigen delivery is not limited to expression by plasmid vectors in the bacterium. Protective antigen sequences that encode antigens of the present disclosure can also integrated in chromosomal sites. Generally the chromosomal sites selected cause insertion of protective antigen-encoding sequences to be inserted into a chromosomal gene, often in replacement of an easily identifiable chromosomal gene. Selection of the chromosomal gene site for insertion is important. First of all, the absence of the inactivated chromosomal gene cannot be deleterious to the vaccine strain to decrease its invasiveness and ability to be highly immunogenic. Also it is often useful to insert the antigen encoding sequence into a gene near the origin of chromosome replication since this increases gene copy number during growth of the bacterial vector and thus the amount of antigen synthesized to enhance induced immune levels. In some cases, the gene site for insertion is into a gene already inactivated for some other beneficial attribute of the vaccine vector. In all cases, suicide vector technologies are used for the insertion of antigen-encoding sequences into chromosomal sites.

Recombinant Antibiotic-Sensitive *Edwardsiella* bacteria

Recombinant attenuated *Edwardsiella* bacteria that may be used with the disclosed Ich protective antigens are disclosed in U.S. Pat. No. 9,045,742, which is incorporated by reference in its entirety for the teaching of these recombinant bacteria and their uses as vaccines. The bacterium may be used to induce in a fish an immune response to *Ichthyophthirius multifiliis*. Advantageously, the bacterium may be capable of regulated lysis to facilitate biocontainment. For instance, the bacterium may be derived from *E. ictaluri* or *E. piscicida.*

An aspect of the present disclosure of significance is the fact that *E. piscicida* is able to infect not only catfish but also salmonid fish such as trout and salmon as well as tilapia, whereas *E. ictaluri* only infects catfish and therefore can only be used to develop vaccines for catfish.

In embodiments, the bacterium is antibiotic sensitive. The phrase "antibiotic sensitive," as used herein, means that the bacterium has not been genetically manipulated to enhance antibiotic resistance. Without intending to be limiting, in certain embodiments, the bacterium may be sensitive to ampicillin, kanamycin, and/or rifampicin. It is preferable for live bacterial vaccines to be sensitive to antibiotics to preclude transmission of genes for antibiotic resistance to other bacterial pathogens, which could then compromise antibiotic thereby in a disease outbreak with such antibiotic-resistant pathogens.

In particular embodiments, the bacterium is attenuated, in vitro or in vivo. Attenuation is accomplished preferably with a regulated delayed loss of virulence attributes to result in complete attenuation and inability to induce disease symptoms. This regulated loss of virulence can be programed to require some 6 to 12 cell divisions of the vaccine vector bacterium in vivo after immunization of the fish. Additional information relating to attenuation of bacteria can be found in Curtiss, R. III, S. Y. Wanda, B. M. Gunn, X. Zhang, S. A. Tinge, V. Ananthnarayan, H. Mo, S. Wang, and W. Kong. 2009. *Salmonella enterica* serovar Typhimurium strains with regulated delayed attenuation in vivo. Infect. Immun, 77:1071-1082 and Li, Y., S. Wang, G. Scarpellini, B. Gunn, W. Xin, S. Y. Wanda, K. L. Roland, and R. Curtiss III. 2009. Evaluation of new generation *Salmonella entericaserovar* Typhimurium vaccines with regulated delayed attenuation to induce immune responses against PspA. Proc. Natl. Acad, Sci. USA 106:593-598, the entireties of which are incorporated by references as fully set forth herein.

Additionally, the bacterium may be capable of the regulated expression of a nucleic acid encoding the antigen, regulated attenuation, and/or capable of regulated lysis.

In some embodiments, the disclosed bacterium may comprise one or more mutations selected from the group comprising Δcrp; ΔwibT; Δfur; ΔasdA; Δugd; ΔgalE; Δpmi; $\Delta P_{crp}$::TT araC $P_{araBAD}$ crp; $\Delta P_{fur}$::TT araC $P_{araBAD}$ fur $\Delta P_{insA}$::TT araC $P_{araBAD}$ insA or Δgne; ΔesrB; ΔrelA:araC $P_{araBAD}$ lacI TT; ΔasdA::TT araC $P_{araBAD}$ c2; and $\Delta P_{murA}$::TT araC $P_{araBAD}$ murA. Additional *E. piscicida* mutants can those listed in Table 2 below: ΔasdA10, Δfur-11, Δpmi-21, Δcrp-22, ΔznuA23, ΔgalE24, ΔwaaI25, Δcrp22, ΔznuA23, $\Delta P_{rfaH13}$::TT araC $P_{araBAD}$ rfaH, $\Delta P_{rfaH23}$::TT araC $P_{araBAD}$ rfaH, $\Delta P_{crp68}$::TT araC $P_{araBAD}$ crp, $\Delta P_{crp78}$::TT araC $P_{araBAD}$ crp, $\Delta P_{fur170}$::TT araC $P_{araBAD}$ fur, ΔpstS26, $\Delta P_{pstS27}$::TT araC $P_{araBAD}$ pstS, ΔasdA10; $\Delta P_{fur170}$::TT araC $P_{araBAD}$ fur, $\Delta P_{murA180}$::TT araC $P_{araBAD}$ murA, ΔasdA10; $\Delta P_{murA180}$::TT araC $P_{BAD}$ murA, ΔasdA10; $\Delta P_{fur170}$::TT araC $P_{araBAD}$ fur; $\Delta P_{murA180}$::TT araC $P_{araBAD}$ murA, ΔaroA11, ΔphoP12, ΔasdA10; $\Delta P_{fur170}$::TT araC $P_{araBAD}$ fur; ΔaroA11, ΔasdA10; $\Delta P_{fur170}$:TT araC $P_{araBAD}$ fur; $\Delta P_{crp68}$::TT araC $P_{araBAD}$ crp, $\Delta P_{rfaD}$::TT araC $P_{araBAD}$ rfaD, $\Delta P_{lacI28}$::TT araC $P_{araBAD}$ lacI, ΔasdA10; $\Delta P_{fur170}$::TT araC $P_{araBAD}$ fur $\Delta P_{murA180}$::TT araC $P_{araBAD}$ murA; $\Delta P_{lacI28}$::TT araC $P_{araBAD}$ lacI, ΔasdA10; $\Delta P_{fur170}$:TT araC $P_{araBAD}$ fur; □$P_{crp68}$::TT araC $P_{araBAD}$ crp; $\Delta P_{lacI28}$::TT araC $P_{araBAD}$ lacI, ΔasdA10; $\Delta P_{fur170}$::TT araC $P_{araBAD}$ fur, $\Delta P_{murA180}$::TT araC $P_{araBAD}$ murA. Although specific allele and/or promoter numbers may be referenced in the mutations above, the scope is not intended to be limited to these numbers as would be understood by the skilled artisan.

In some embodiments, the bacterium comprises a ΔasdA, $\Delta P_{fur170}$:TT araC $P_{araBAD}$ fur, and $\Delta P_{crp68}$:TT araC $P_{araBAD}$ crp mutation. In some embodiments, the bacterium comprises a ΔrelA::araC $P_{araBAD}$ lacI TT mutation, such as ΔrelA50::araC $P_{araBAD}$ lacI TT, or a ΔasdA::TT araC $P_{araBAD}$ c2 mutation, such as ΔasdA02::TT araC $P_{araBAD}$ c2, or a combination thereof. In some embodiments, the disclosed bacterium may comprise one or more mutations found in the Examples below.

In some embodiments, the disclosed bacterium comprises, in part, at least one chromosomally integrated nucleic acid sequence encoding a repressor. In embodiments, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the re/A nucleic acid sequence. Alternatively, a nucleic acid sequence encoding a repressor may be integrated into a locus comprising a nucleic acid sequence that was previously removed (e.g. knocked out) from the bacterium's genome.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

In other embodiments, the repressor is encoded on a low copy number plasmid compatible with plasmids encoding protective antigens. Such a plasmid is pYA232 which possesses a pSC101 ori compatible with p15A ori, pBR ori and pUC ori plasmids and which possesses the lacI$^q$ allele encoding synthesis of the LacI repressor blocking transcription of genes regulated by the $P_{trc}$ promoter present in all expression plasmids used for vaccine construction.

In an embodiment, antigen expression is controlled by $P_{trc}$ such that LacI is a repressor since $P_{trc}$ has the lacO sequence. In another embodiment, an araC $P_{araBAD}$ lacI construction is chromosomally integrated so that the Ich antigen is synthesized increasingly due to dilution of LacI by cell division in vivo in the absence of arabinose.

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from E. coli if the recombinant bacterium is from the genus Edwardsiella. Alternatively, the repressor may be from a bacteriophage.

Suitable repressors are known in the art, and may include, for instance, LacI of E. coli, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI.

The chromosomally integrated nucleic acid sequence encoding a repressor can be operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{araBAD}$ system. The araC-$P_{araBAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{araBAD}$. For use as described herein, a cassette with the araC nucleic acid sequence and the araC-araBAD promoter may be used. This cassette is referred to herein as araC-$P_{araBAD}$. The AraC protein is both a positive and negative regulator of $P_{araBAD}$. In the presence of arabinose, the AraC protein is a positive regulatory element that allows expression from $P_{araBAD}$. In the absence of arabinose, the AraC protein represses expression from $P_{araBAD}$. This can lead to a 1,200-fold difference in the level of expression from $P_{araBAD}$.

Other enteric bacteria contain arabinose regulatory systems homologous to the araC-araBAD system from E. coli. For example, there is homology at the amino acid sequence level between the E. coli and the S. Typhimurium AraC proteins, and less homology at the DNA level. However, there is high specificity in the activity of the AraC proteins. For example, the E. coli AraC protein activates only E. coli $P_{araBAD}$ (in the presence of arabinose) and not S. Typhimurium $P_{araBAD}$ Thus, an arabinose-regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In some embodiments, a regulatable promoter may be sensitive to rhamnose or xylose. For instance, a rhamnose or xylose regulatory system from *E. coli* may be used. In both cases the regulatable promoter allows transcription in the presence of the sugar and ceases transcription in the absence of the sugar.

The nucleic acid sequences of the promoters detailed herein are known in the art, and methods of operably-linking them to a chromosomally integrated nucleic acid sequence encoding a repressor are known in the art and detailed in the examples.

A nucleic acid sequence encoding a repressor and regulatable promoter detailed above may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of Lad synthesis. In one embodiment, the start codon of the LacI repressor may be altered from GTG to ATG, In another embodiment, the SD sequence may be altered from AGGG to ALGA. In yet another embodiment, the codons of lac, may be optimized according to the codon usage for *Edwardsiella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

The disclosed recombinant bacterium can comprise a vector comprising a nucleic acid sequence encoding at least one antigen of interest operably linked to a promoter. The promoter can be regulated by the chromosomally encoded repressor, such that the expression of the nucleic acid sequence encoding the antigen is repressed during in vitro growth of the bacterium, but the bacterium is capable of high level synthesis of the antigen in an animal (e.g. fish). The vector may be a part of a balanced-lethal or balanced-attenuation host vector system As used herein, "vector" refers to an autonomously replicating nucleic acid unit. The present invention can be practiced with any known type of vector, including viral, cosmid, phasmid, and plasmid vectors.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

In some cases, vectors used herein do not comprise antibiotic resistance markers to select for maintenance of the vector.

The vector can comprise a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $PT7_{lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as $\lambda$ promoters $P_L$ and $P_R$.

In some embodiments, the promoter regulates expression of a nucleic acid sequence encoding the antigen, such that expression of the nucleic acid sequence encoding the antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high-level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression is generally not absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen, Consequently, the copy number correlating with high level expression can and will vary depending on the antigen and the type of immune response desired. Methods of determining whether an antigen elicits an immune response such as by measuring antibody levels or antigen-dependent T cell populations or antigen-dependent cytokine levels are known in the art, and methods of measuring levels of expression of antigen encoding sequences by measuring levels of mRNA transcribed or by quantitating the level of antigen synthesis are also known in the art.

Although extrachromosomal vectors, such as plasmids, may be designed with unique nucleotide sequences, there is some potential for vector-vector recombination to occur that might lead to deletion of and/or alterations in one or more nucleic acid sequences encoding an antigen of interest. This could potentially expose a host to unintended antigens. Accordingly, in some embodiments, the recombinant bacterium may be deficient in one or more of the enzymes that catalyzes recombination between extrachromosomal vectors. If a bacterium comprises only a single extrachromosomal vector, then such mutations are not necessary. If two or more extrachromosomal vectors are used, however, then the recombinant bacterium may be modified so that one or more recombination enzymes known to catalyze vector-vector recombination are rendered non-functional.

In certain embodiments, the recombination enzymes do not participate in recombinations involving chromosomal nucleic acid sequences, For instance, the recombinant bacterium may comprise a ΔrecF and a ΔrecJ mutation. These mutations do not alter the virulence attributes of the recombinant bacterium, nor its ability to effectively colonize effector lymphoid tissues after immunization of a host. One of skill in the art will appreciate that other recombination enzymes known to catalyze vector-vector recombination but not to participate in recombinations involving chromosomal nucleic acid sequences may be targeted for deletion or mutation in addition to recF and recJ.

Alternatively, the recombinant bacterium may be modified by introducing a ΔrecA mutation that prevents all recombination, whether between vectors or chromosomal nucleic acid sequences. A recombinant bacterium with a ΔrecA mutation may also be attenuated.

The disclosed recombinant bacterium can be attenuated. "Attenuated" refers to the state of the bacterium wherein the bacterium has been weakened from its wild type fitness by some form of recombinant or physical manipulation. This includes altering the genotype of the bacterium to reduce its ability to cause disease, However, the bacterium's ability to colonize the host and induce immune responses is, preferably, not substantially compromised.

Methods for attenuating a bacterium are known in the art. In some embodiments, the attenuation may be regulated attenuation. In these embodiments, the bacterium generally comprises a chromosomally integrated regulatable promoter. The promoter replaces the native promoter of, and is operably linked to, at least one nucleic acid sequence encoding an attenuation protein, such that the absence of the function of the protein renders the bacterium attenuated, In some embodiments, the promoter is modified to optimize the regulated attenuation.

Herein, "attenuation protein" is meant to be used in its broadest sense to encompass any protein the absence of which attenuates a bacterium, For instance, in some embodiments, an attenuation protein may be a protein that helps protect a bacterium from stresses encountered in the gastrointestinal tract or respiratory tract. Non-limiting examples may be the Fur and Crp proteins. In other embodiments, the protein may be a necessary component of the cell wall of the bacterium, such as the protein encoded by murA. In still other embodiments, the protein may be involved in the production of LPS, such as the protein encoded by the insA or gne nucleic acid sequence.

The native promoter of at least one, two, three, four, five, or more than five attenuation proteins may be replaced by a regulatable promoter as described herein. In one embodiment, the promoter of one of the proteins Fur or Crp may be replaced. In another embodiment, the promoter of both Fur and Crp may be replaced.

If the promoter of more than one attenuation protein is replaced, each promoter may be replaced with a regulatable promoter, such that the expression of each attenuation protein encoding sequence is regulated by the same compound or condition, Alternatively, each promoter may be replaced with a different regulatable promoter, such that the expression of each attenuation protein encoding sequence is regulated by a different compound or condition such as by the sugars arabinose, rhamnose or xylose.

The native promoter of a nucleic acid encoding an attenuation protein can be replaced with a regulatable promoter operably linked to the nucleic acid sequence encoding an attenuation protein.

The regulatable promoter used herein generally allows transcription of the nucleic acid sequence encoding the attenuation protein while in a permissive environment (i.e. in vitro growth), but ceases transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of rhamnose, or xylose in the environment. The promoters detailed herein are known in the art, and methods of operably linking them to a nucleic acid sequence encoding an attenuation protein are known in the art.

In certain embodiments, the recombinant bacterium may comprise a $\Delta P_{fur}$::TT araC $P_{araBAD}$ fur mutation, $\Delta P_{crp}$::TT araC $P_{araBAD}$ crp mutation, a $\Delta P_{insA}$::TT araC $P_{araBAD}$ insA mutation, a $\Delta$gne-25 mutation, or a combination thereof. For instance, a bacterium may comprise a $\Delta P_{fur70}$::TT araC $P_{araBAD}$ fur mutation, a $\Delta P_{crp11}$::TT araC $P_{araBAD}$ crp mutation, or a $\Delta P_{insA40}$TT araC $P_{araBAD}$ insA mutation, or a combination thereof. Growth of such strains in the presence of arabinose leads to transcription of the fur and/or crp and/or insA nucleic acid sequences, but nucleic acid sequence expression ceases in a host because there is no free arabinose. Attenuation develops as the products of the fur and/or the crp and/or the insA nucleic acid sequences are diluted at each cell division.

Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta$araBAD or mutations that block the uptake and/or breakdown of rhamnose, or xylose, however, may prevent such acid production and enable use of higher sugar concentrations with no ill effects.

When the regulatable promoter is responsive to arabinose, the onset of attenuation may be delayed by including additional mutations that would prevent use of arabinose or enhance retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments, the SD sequences and/or the start codons for the fur nucleic acid sequences may be altered so that the production levels of these nucleic acid products are optimal for regulated attenuation.

In an exemplary embodiment, a recombinant bacterium may be attenuated as described above and may be capable of the regulated expression of a nucleic acid sequence encoding an antigen. In which case, both regulated attenuation and regulated expression of an antigen encoding sequence may be dependent upon an arabinose regulatable system. Consequently, the concentration of arabinose needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. One of skill in the art will appreciate that other nucleic acid sequences, in addition to fur, may also be altered as described herein in combination with other well-known protocols. In addition, these attenuating nucleic acid sequences may be regulated by other systems using well-established protocols known to one of skill in the art, For example, they may be regulated using promoters dependent on addition of rhamnose, or xylose rather than arabinose.

Other methods of attenuation are known in the art. For instance, attenuation may be accomplished by altering (e.g., deleting) native nucleic acid sequences found in the wild type bacterium. In some embodiments, the bacterium may comprise a mutation in a transcription factor as a means to attenuate the bacterium. By way of non-limiting example, the bacterium may comprise a $\Delta$esrB70 mutation.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes).

In some embodiments, a recombinant bacterium may also comprise a $\Delta P_{crp}$::TT araC $P_{araBAD}$ crp deletion-insertion mutation. Since the araC $P_{araBAD}$ cassette is dependent both on the presence of arabinose and the binding of the catabolite repressor protein Crp, a $\Delta P_{crp}$::TT araC $P_{araBAD}$ crp deletion insertion mutation may be included as an additional means to reduce expression of any nucleic acid sequence under the control of the $P_{araBAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{araBAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{araBAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{araBAD}$ This strategy may also be used in other systems responsive to Crp, such as the systems responsive to rhamnose and xylose described above.

A recombinant bacterium may be capable of regulated lysis. For instance, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP, which is incorporated in its entirety by reference as fully set forth herein. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., Δalr and ΔmurI mutations), which are both unique constituents of the peptidoglycan layer of the bacterial cell wall Similarly, various embodiments may comprise the araC $P_{araBAD}$ c2 cassette inserted into the asd nucleic acid sequence that encodes aspartate semialdehyde dehydrogenase. Such a mutation may comprise ΔasdA02::TT araC $P_{araBAD}$ c2. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above. The vector enables the regulated expression of an antigen encoding sequence through the repressible promoter.

In another example, a recombinant bacterium may comprise a $\Delta P_{murA}$::TT araC $P_{araBAD}$ murA deletion-insertion mutation. This mutation modifies the bacterium such that the synthesis of an essential constituent of the rigid layer of the bacterial cell wall is dependent on a nutrient (e.g., arabinose) that can be supplied during the growth of the microorganism. This type of mutation makes synthesis of muramic acid (a unique essential constituent of the peptidoglycan layer of the bacterial cell wall) dependent on the presence of arabinose that can be supplied during growth of the bacterium in vitro.

When arabinose is absent, however, as it is in an animal or human host, the essential constituent of the peptidoglycan layer of the cell wall is not synthesized. This mutation represents an arabinose dependent lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{araBAD}$ murA deletion-insertion mutation grown in the presence of arabinose exhibit effective colonization of effector lymphoid tissues after mucosal vaccination prior to undergoing lysis due to the inability to synthesize muramic acid.

Vaccine Compositions and Administration

The disclosed recombinant bacterium may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported.

Vaccine compositions disclosed herein may be administered to a host capable of mounting an immune response. Preferably, the host is a fish. In embodiments, the host is a teleost fish, such as a catfish, trout, salmon, or tilapia. In an exemplary embodiment, the host is a fish used in aquaculture. The vaccine can be administered as a prophylactic or for treatment purposes.

In exemplary embodiments, the recombinant bacterium is alive when administered to a host in a vaccine composition of the invention. In another exemplary embodiment, the recombinant bacterium administered to a host in a vaccine composition comprises one or more of the mutations selected from the group comprising $\Delta P_{crp}$::TT araC $P_{araBAD}$ crp, $\Delta P_{fur}$::TT araC $P_{araBAD}$ fur; $\Delta P_{insA}$::TT araC $P_{araBAD}$ insA or Δgne; ΔesrB; ΔrelA::araC $P_{araBAD}$ ladI TT; ΔasdA::TT araC $P_{araBAD}$ c2; and $\Delta P_{murA}$::TT araC $P_{araBAD}$ murA. For instance, the bacterium may comprise one, two, three, four, five, six, or seven mutations from the group comprising $\Delta P_{crp}$::TT araC $P_{araBAD}$ crp, $\Delta P_{fur}$::TT araC $P_{araBAD}$ fur; $\Delta P_{insA}$::TT araC $P_{araBAD}$ insA or Δgne; ΔesrB; ΔrelA::araC $P_{araBAD}$ lacI TT; ΔasdA::TT araC $P_{araBAD}$ c2; and $\Delta P_{murA}$::TT araC $P_{araBAD}$ murA. With the exception of asd mutations that are used in the balanced-lethal vector-host system and the $\Delta P_{murA}$::TT araC $P_{araBAD}$ murA mutation that are both complemented in vaccine bacterium strains, all of the above mutations do not impose any auxotrophic requirements for nutrients. Bacterial strains with these mutations are therefore not auxotrophs.

In certain embodiments, a vaccine disclosed herein may elicit an immune response against *Ichthyophthirius multifiliis* in a host. Suitable vaccine composition formulations and methods of administration are detailed below.

A vaccine composition comprising a recombinant bacterium disclosed herein may optionally comprise one or more possible additives, such as carriers, preservatives, stabilizers, adjuvants, and other substances.

In one embodiment, the vaccine comprises an adjuvant. In exemplary embodiments, the use of a live attenuated recombinant bacterium may act as a natural adjuvant.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). Vaccines for fish to be administered by bath immunization of fish can be encapsulated, incorporated into a protozoan consumed by fish or placed in food pellets. The vaccine prior to use can be lyophilized and thus subject to reconstitution in a fluid.

Care should be taken when using additives so that the live recombinant bacterium is not killed, or have its ability to effectively colonize lymphoid tissues such as the GALT, and NALT, compromised by the use of additives. Stabilizers, such as lactose or monosodium glutamate (MSG), may be added to stabilize the vaccine formulation against a variety of conditions, such as temperature variations or a freeze-drying process.

In exemplary embodiments, a vaccine composition disclosed herein is administered in a bath. For instance, a vaccine composition may be administered to fish fry in a bath. In other exemplary embodiments, a vaccine composition disclosed herein may be administered in a live fish food, such as protozoa. In certain exemplary embodiments, a vaccine composition disclosed herein may be administered via food pellets for oral consumption. By way of non-limiting example, booster administration may be given via food pellets.

The dosages of a vaccine composition of the invention can and will vary depending on the recombinant bacterium and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration or uptake via gills could be about $1 \times 10^7$ to $1 \times 10^{10}$ CFU depending upon the age of the host to be immunized. Administering multiple dosages may also be used as needed to provide the desired level of protective immunity.

Methods of Administration

In order to simplify aquaculture use, bath/oral (mucosal since some vaccine uptake can be in gills) administration is preferred. In some embodiments, these compositions are formulated for administration by injection (e.g., intracolemically, also referred to as intracoelemically, intravenously, subcutaneously, intramuscularly, etc.). Accordingly, these compositions are preferably combined with pharmaceutically acceptable vehicles such as saline, Ringer's solution, dextrose solution, and the like.

Kits

Also disclosed are kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably by a mucosal route as would occur during bath immersion vaccination. In certain embodiments, a kit can comprise one or more bacteria, one or more vectors, and optionally a constituent required for permissive growth and/or expression, for example arabinose.

Methods of Use

A further aspect of the invention encompasses methods of using a recombinant bacterium disclosed herein. For instance, a method is provided for modulating a host's immune system. The method comprises administering to the host an effective amount of a composition comprising a recombinant bacterium disclosed herein. One of skill in the art will appreciate that an effective amount of a composition is an amount that will generate the desired immune response (e.g., mucosal, humoral or cellular). Methods of monitoring a host's immune response are well-known to veterinarians and other skilled practitioners. For instance, assays such as ELISA may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, a method is disclosed for eliciting an immune response against an antigen in a host. The method comprises administering to the host an effective amount of a composition comprising a recombinant bacterium disclosed herein.

In still another embodiment, a recombinant bacterium disclosed herein may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

Definitions

The term "altered," as used herein, refers to any change in the nucleic acid sequence that results in differential expression of the nucleic acid sequence, or results in other changes to aspects of the transcribed sequence, such as altered mRNA stability and the like. In an exemplary embodiment, the alteration results in the nucleic acid sequence not being expressed in a host. In one embodiment, the alteration is a deletion. In another embodiment, the alteration places an essential nucleic acid under the control of a regulatable promoter, such that the nucleic acid is not expressed in a host. In other cases, the result of alteration increases gene expression.

The term "balanced-lethal" or "balanced attenuated" host vector systems refers to a recombinant bacterium comprising at least one chromosomally encoded essential nucleic acid sequence, wherein the essential nucleic acid sequence is altered so that it is not expressed, and at least one extrachromosomal vector. An "essential nucleic acid" is a native nucleic acid whose expression is necessary for cell viability or a metabolic activity essential for virulence. Consequently, a bacterium is non-viable and/or avirulent if an essential nucleic acid sequence is not expressed. Therefore, the bacterium further comprises at least one extrachromosomal vector. The vector comprises a nucleic acid sequence, that when expressed, substantially functions as the essential nucleic acid. Hence, the bacterium is viable and/or virulent when the vector is expressed. This promotes stable maintenance of the vector.

The term "native," as used herein, refers to a biomolecule in a form typically found in the strain a recombinant bacterium is derived from.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same.

The term "virulence," as used here, refers to the ability of the recombinant bacterium to infect a host.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

A number of embodiments of the invention have been described. Nevertheless, it will be understood that various modifications may be made without departing from the spirit and scope of the invention. Accordingly, other embodiments are within the scope of the following claims.

EXAMPLES

*Edwardsiella piscicida* is a Gram-negative pathogen that generally causes edwardsiellosis in marine and freshwater fish. *E. piscicida* is more common in fish disease outbreaks (Loch et al., 2017; Shao et al., 2015; Griffin et al., 2014). The genus *Edwardsiella* consists of five species: *E. hoshinae, E. ictaluri, E. tarda, E. piscicida,* and *E. anguillarum. E. piscicida* resulted from a reclassification of diverse isolates obtained from diseased fish and was previously identified as *E. tarda*, which infects both fish and mammals. *E. piscicida* is fish-specific and presents a worldwide distribution being isolated from a wide range of hosts including catfish, carp, tilapia, mullet, salmon, trout and flounder and ecological niches causing high mortalities in fish.

Abayneh et al. (2012) reclassified the fish-pathogenic Glade of *Edwardsiella tarda*, as *Edwardsiella piscicida*, which is a versatile pathogen causing disease in many species of both cultured and wild fish populations. Griffin et al, (2014) supported the above findings based on comparison of gyrB sequences of many *Edwardsiella* strains. The homology between *E. piscicida* and *E. tarda* was <87% whereas between *E. piscicida* and *E. ictaluri* was 95.9%.

Mucosally-delivered *Edwardsiella* species efficiently attach to and invade mucosal associated lymphoid tissues; gut-associated lymphoid tissue (GALT), skin-associated lymphoid tissue (SALT), the gill-associated lymphoid tissue (GIALT) and the recently discovered nasopharynx-associated lymphoid tissue (NALT) in fish.

Since *E. piscicida* infects both fresh-water and marine fish species, it was chosen to develop a recombinant attenuated *Edwardsiella* vaccine (RAEV) vector system to ultimately enable developing vaccines to prevent infectious diseases in catfish, trout, salmon and tilapia.

Table 1 below lists embodiments of the plasmids according to the present disclosure as constructed and their properties, and Table 2 lists embodiments of *E. piscicida* strains according to the present disclosure constructed with their genotypes and derivations. Table 1 also lists some *E. coli* plasmids used in construction of recombinant plasmids encoding protective antigens. Table 2 also lists several *E. coli* strains used for recombinant plasmid construction and for conjugational transfer of suicide vectors. Based on the research on design and construction of plasmids and *E. piscicida* strains described in the Examples below:

TABLE 1

Plasmids

| Plasmid name | Relevant characteristics |
|---|---|
| pG8R8000 | Suicide vector to generate ΔasdA10, pRE112 Replicon |
| pG8R8001 | Suicide vector to generate Δfur, pRE112 Replicon |
| pG8R8002 | Suicide vector to generate Δpmi, pRE112 Replicon |
| pG8R8003 | Suicide vector to generate Δcrp, pRE112 Replicon |
| pG8R8004 | Suicide vector to generate ΔznuA, pRE112 Replicon |
| pG8R8005 | Suicide vector to generate ΔgalE, pRE112 Replicon |
| pG8R8006 | Suicide vector to generate Δwaal, pRE112 Replicon |
| pG8R8007 | Suicide vector to generate $\Delta P_{rfaH13}$::TT araC $P_{araBAD}$ rfaH, pRE112 Replicon |
| pG8R8008 | Suicide vector to generate $\Delta P_{rfaH23}$::TT araC $P_{araBAD}$ rfaH, pRE112 Replicon |
| pG8R8009 | Suicide vector to generate $\Delta P_{crp68}$::TT araC $P_{araBAD}$ crp, pRE112 Replicon |
| pG8R8010 | Suicide vector to generate $\Delta P_{crp78}$::TT araC $P_{araBAD}$ crp, pRE112 Replicon |
| pG8R8011 | *E. piscicida* $P_{asd,}$ pUC ori (Wild-type $P_{asdA}$ SD ATG start) |
| pG8R8012 | *E. piscicida* $SD_{asd,}$ pUC ori ($\Delta P_{asdA}$ Wild-type SD ATG start) |
| pG8R8013 | *E. piscicida* asd, pUC ori (Only ORF) |
| pG8R8014 | *E. piscicida* $SD_{asd-}$GTG pUC ori (Wild-type SD GTG start) |
| pG8R8015 | *E. piscicida* $P_{asd}$, pBR ori (Wild-type $P_{asdA}$ SD ATG start) |
| pG8R8016 | *E. piscicida* $SD_{asd,}$ pBR ori ($\Delta P_{asdA}$ Wild-type SD ATG start) |
| pG8R8017 | *E. piscicida* asd, pBR ori (Only ORF) |
| pG8R8018 | *E. piscicida* $SD_{asd}$-GTG pBR ori Wild-type SD GTG start) |
| pG8R8019 | IAG52B inserted into pG8R8016 |
| pG8R8020 | IAG52B inserted into pG8R8018 |
| pG8R8021 | $P_{fur}$, pYACYC184 |
| pG8R8022 | 102 bp, Optimized bla SS sequence from pG8R17 was positioned under the control of the $P_{trc}$ promoter of the $Asd^+$ vector pG8R8018 with MCS, pBR ori |
| pG8R8023 | IAG52B gene was cloned into pG8R8022 in EcoRI and BamHI site |
| pG8R8024 | Suicide vector to generate $\Delta P_{fur170}$::TT araC $P_{araBAD}$ fur, pRE112 Replican |
| pG8R8025 | Suicide vector to generate $\Delta P_{murA}$::TT araC $P_{araBAD}$ murA, pRE112 Replican |
| pG8R8026 | Suicide vector to generate ΔaroA, pRE112 Replicon |

TABLE 1-continued

Plasmids

| Plasmid name | Relevant characteristics |
|---|---|
| pG8R8027 | Suicide vector to generate ΔphoP, pRE112 Replicon |
| pG8R8028 | IAG48 was cloned into pYA3493 in EcoRI and BamHI site |
| pG8R8029 | IAG52B was cloned into pYA3493 in EcoRI and BamHI site |
| pG8R8030 | IAG52B was cloned into |
| pG8R8031 | Suicide vector to generate ΔpstS, pRE112 Replicon |
| pG8R8032 | Suicide vector to generate $\Delta P_{psts}$::TT araC $P_{araBAD}$ psts, pRE112 Replicon |
| pG8R8033 | Suicide vector to generate $\Delta P_{rfaD}$::TT araC $P_{araBAD}$ rfaD, pRE112 Replicon |
| pG8R8034 | IAG52A was cloned into pYA3493 in EcoRI and BamHI site |
| pYA232 | The 1.1 kb EcoRI fragment of pACJC178 containing the lacI$^q$ gene inserted into the EcoRI site of pSC101 |
| pYA3493 | Plasmid for periplasmic secretion by β-lactamase signal sequences β-lactamase signal sequences from pBR322 was PCR amplified and cloned in pYA3342 at NcoI and EcoRI sites |
| pYA3341 | High copy Asd$^+$ vector obtained by deleting the lacZ (~161 bp) gene from pYA3339. |
| pYA3342 | *Salmonella* Asd$^+$ vector. Medium copy number derivative of pYA3341 containing SD asdA gene. It still complements Δasd mutants. |
| pRE112 | Allelic exchange suicide vector that provide both selection for chromosomal integration (cmR) and counterselection for loss of vector DNA and the wild type allele. |
| pYA4763 | (WSD-GTG-asd) Lysis vector; MurA-AsdA lysis vector with WSD-GTG-asd. SD-GTG-murA was PCR-amplified from pYA3681 and ligated to pYA4710 after enzyme digestion to generate pYA4765. Sequences were verified and reduced amount of Asd was confirmed by western blot. |
| pG8R110 | araC.Nt-pBAD-murA-asd |
| pG8R111 | Sequence encoding rrfGTT, Ptrc and MCS was cut from pYA3681 (SphI/PstI) and cloned into pYA4763. MCS sequence see pYA3681. Plasmid Derivation: pYA4763 Marker: Asd, arabinose pBR ori |
| pG8R114 | Optimized bla SS sequence was cloned into pYA4763 with MCS. Plasmid derivation: pYA4763 |

TABLE 2

Bacterial Strains

| Strain Name | Relevant characteristics | Parent strain |
|---|---|---|
| *List of E. piscicida strains* | | |
| J118 | Wild-type *E. piscicida* | |
| χ16000 | ΔasdA10 | J118 |
| χ16001 | Δfur-11 | J118 |
| χ16002 | Δpmi-21 | J118 |
| χ16003 | Δcrp-22 | J118 |
| χ16004 | ΔznuA23 | J118 |
| χ16005 | ΔgalE24 | J118 |
| χ16006 | Δwaal25 | J118 |
| χ16007 | Δcrp22 ΔznuA23 | χ16003 |
| χ16008 | $\Delta P_{rfaH13}$::TT araC $P_{araBAD}$ rfaH | J118 |
| χ16009 | $\Delta P_{rfaH23}$::TT araC $P_{araBAD}$ rfaH | J118 |
| χ16010 | $\Delta P_{crp68}$::TT araC $P_{araBAD}$ crp | J118 |
| χ16011 | $\Delta P_{crp78}$::TT araC $P_{araBAD}$ crp | J118 |
| χ16012 | $\Delta P_{fur170}$::TT araC $P_{araBAD}$ fur | J118 |
| χ16013 | ΔpstS26 | J118 |
| χ16014 | $\Delta P_{pstS27}$::TT araC $P_{araBAD}$ pstS | J118 |
| χ16015 | ΔasdA10; $\Delta P_{fur170}$::TT araC $P_{araBAD}$ fur | χ16000 |
| χ16016 | $\Delta P_{murA180}$::TT araC $P_{araBAD}$ murA | J118 |
| χ16017 | ΔasdA10; $\Delta P_{murA180}$::TT araC $P_{BAD}$ murA | χ16000 |
| χ16018 | ΔasdA10; $\Delta P_{fur170}$::TT araC $P_{araBAD}$ fur; $\Delta P_{murA180}$::TT araC $P_{araBAD}$ murA | χ16015 |
| χ16019 | ΔaroA11 | J118 |
| χ16020 | ΔphoP12 | J118 |
| χ16021 | ΔasdA10; $\Delta P_{fur170}$::TT araC $P_{araBAD}$ fur; ΔaroA11 | χ16015 |
| χ16022 | ΔasdA10; ΔPfur170::TT araC $P_{araBAD}$ fur; $\Delta P_{crp68}$::TT araC $P_{araBAD}$ crp | χ16015 |
| χ16023 | $\Delta P_{rfaD}$::TT araC $P_{araBAD}$ rfaD | J118 |
| χ16024 | $\Delta P_{lacI28}$::TT araC $P_{araBAD}$ lacI | J118 |
| χ16025 | ΔasdA10; $\Delta P_{fur170}$::TT araC $P_{araBAD}$ fur; $\Delta P_{murA180}$::TT araC $P_{araBAD}$ murA; $\Delta P_{lacI28}$::TT araC $P_{araBAD}$ lacI | χ16018 |
| χ16026 | ΔasdA10; $\Delta P_{fur170}$::TT araC $P_{araBAD}$ fur; $\Box P_{crp68}$::TT araC $P_{araBAD}$ crp; $\Delta P_{lacI28}$::TT araC $P_{araBAD}$ lacI | χ16022 |
| χ16027 | ΔasdA10; $\Delta P_{fur170}$::TT araC $P_{araBAD}$ fur, $AP_{murA180}$::TT araC $P_{araBAD}$ murA | χ16018 |
| *List of E. coli strains* | | |
| χ6212 | φ80d lacZ ΔM15 deoR Δ(lacZYA-argF)U169 supE44 λ$^-$ gyrA96 recA1 relA1 endA1 ΔasdA4 Δzhf-2::Tn10 hsdR17 (r-m+) | χ6101 (or DH5α) and χ2981 |
| χ7213 | thi-1 thr-1 leuB6 glnV44 fhuA21 lacY1 recA1 RP4-2-Tc::Mu[λpir] ΔasdA4 Δ(zhf-2::Tn10) | MGN-614 |

Example 1

Generation of RAEV Strains with Balanced-Lethal Asd$^+$ Vectors

Figure 1A:
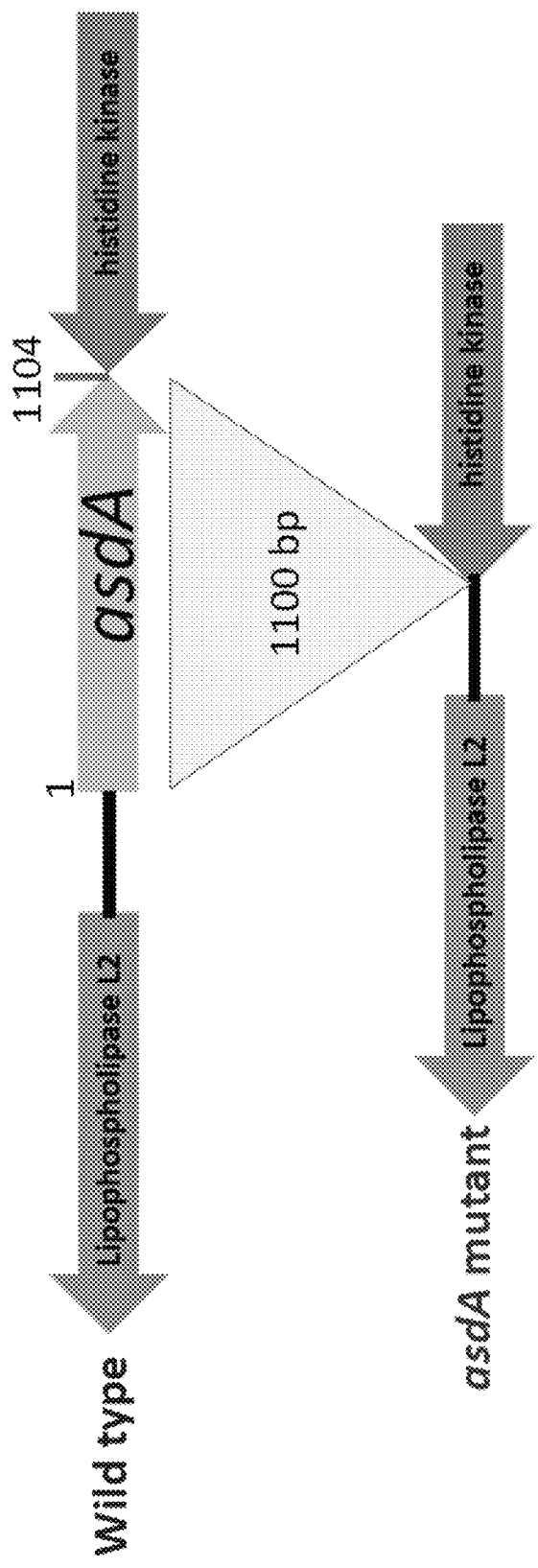
Figure 1B:
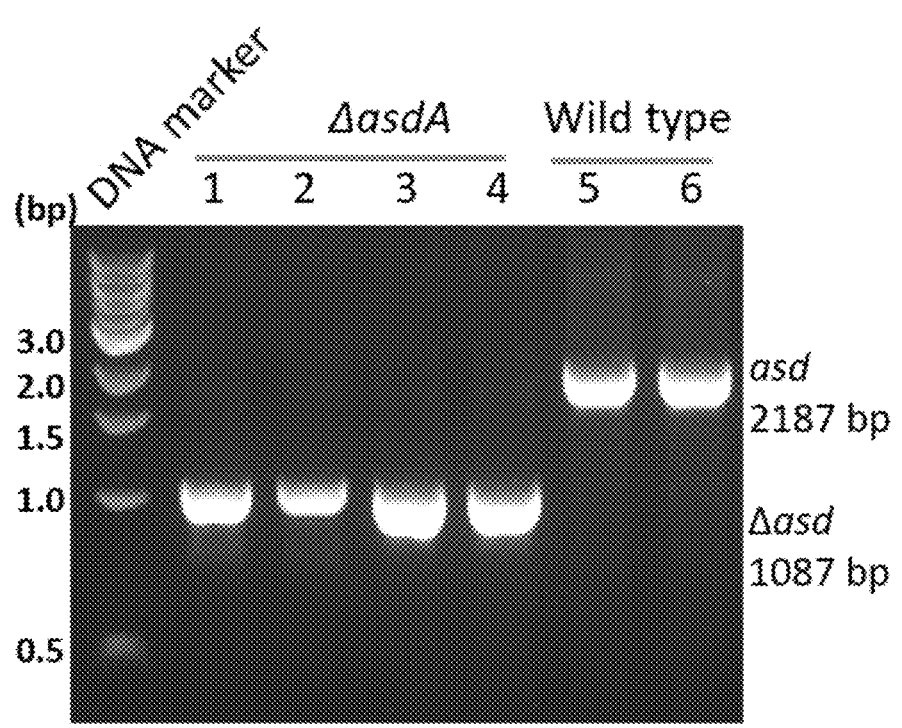

To develop antibiotic-sensitive strains of live attenuated recombinant bacterial vaccines, we use a balanced-lethal host-vector system by deletion of the aspartate β-semialdehyde dehydrogenase (asd) gene. Asd is a highly conserved homodimeric enzyme encoded by the asdA gene and performs a key step in the production of diaminopimelic acid (DAP). asdA mutants of Gram-negative bacteria have an obligate requirement for DAP. In environments deprived of DAP (i.e., animal tissues), they undergo lysis. As a first step to develop an antibiotic-sensitive RAEV strain, the *E. piscicida* asdA gene were characterized and deleted.

Employing suicide vector technology, antibiotic-sensitive asdA mutants were developed. FIG. 1A is an illustration of using suicide vector technology to generate the 1100 bp deletion of the *E. piscicida* asdA gene from the chromosome of J118 to generate χ16000 that is antibiotic-sensitive. More specifically, the recombinant suicide vector pG8R8000 carrying the linked flanking regions (432 bp and 583 bp) to generate an in-frame deletion of the asdA gene was constructed. The ΔasdA10 defined deletion mutation encompasses a 1,100 base pair deletion including the ATG start codon but not including the last four bases "CTAG" of the gene. Primers (primer 1) 5'-CAT TCTAGATCCGGATATTTCATATAGCTTTCAAT-'3 and (primer 2) 5'-CGCGGACTAGATGCACTCCTGCCTTGGATGGTGACGAGTTG-'3 were designed to amplify the upstream asdA flanking region (432 bp). The downstream asdA flanking region (583 bp) was amplified by primers (primer 3) 5'-AGGAGTGCATCTAGTCCGCGCCCTGGTACGGCGCAGGC-'3 and (primer 4) 5'-CAT GGTACCATTTCTTATTTAATGCCCTGAATACC-'3. A XbaI site was included in primer 1 (underlined) and KpnI site was included in primer 4. The flanking regions were amplified from *E. piscicida* J118 genomic DNA. The two PCR products were fused by overlapping PCR with primers 1 and 4 and the products were cloned into the XbaI/KpnI site of the suicide vector pRE112. The resulting plasmid was designated pG8R8000. To construct the *E. piscicida* ΔasdA10 mutant, the suicide plasmid was conjugationally transferred from *Escherichia coli* χ7213 to *E. piscicida* wild-type strain J118. Strains containing single-crossover plasmid insertions were isolated on BHI agar plates containing Col, Cm, and DAP. Loss of the suicide vector after the second recombination between homologous regions (i.e., allelic exchange) was selected by using the sacB-based sucrose sensitivity counter-selection system. The colonies were screened for $Cm^S$, $Col^r$ and for growth only in the presence of DAP. DAP plate colonies were screened by PCR using primer 1 and 4 to generate the data in FIG. 1B.

Figure 2:
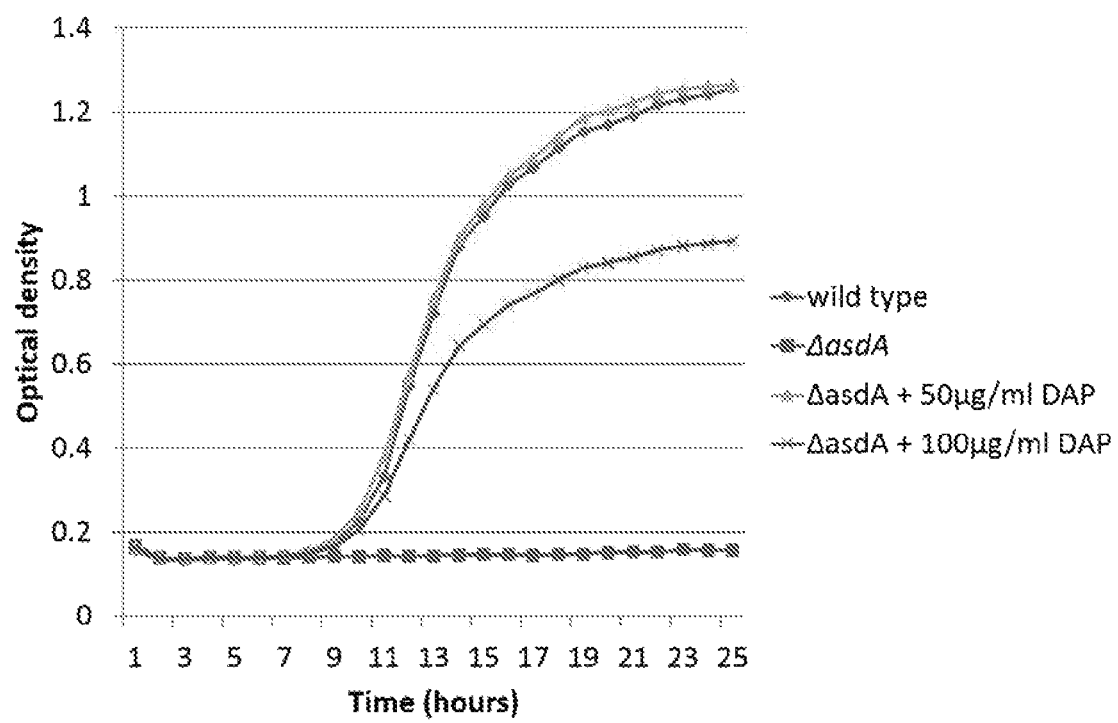

FIG. 2 is a graph showing growth curve analysis of wild-type and the χ16000 ΔasdA mutant *Edwardsiella piscicida* with and without diaminopimelic acid (DAP). In the absence of DAP there is no growth of χ16000. The addition of 50 μg DAP/ml gave optimal growth of χ16000 equal to the growth of the wild-type parental strain J118. Addition of 100 μg DAP/ml led to some toxicity probably due to synthesis of an excess of lysine that gets decarboxylated to a toxic cadaverine.

Figure 4:
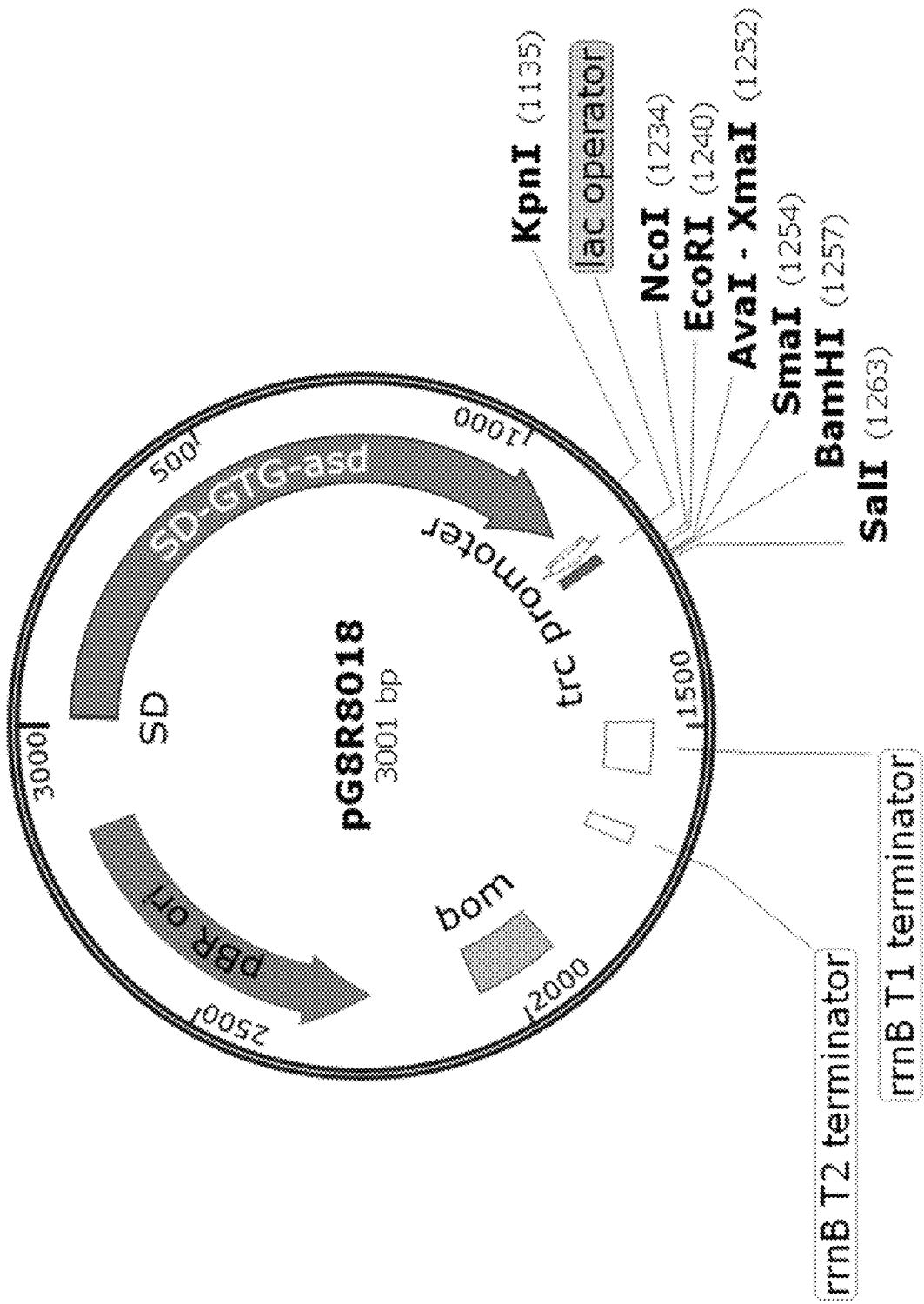

A series of different $Asd^+$ plasmid vectors were constructed with pUC ori and pBR ori containing the *E. piscicida* asdA gene with modifications of the asdA promoter, SD sequence and start codon. The *E. piscicida* asdA gene was amplified with its wild-type promoter and Shine-Dalgarno (SD) sequence or with only the SD asdA sequence and also with modification of the start codon from ATG to GTG or the asdA gene without its SD sequence by using primers listed in Table 3 below. Forward and reverse primers were tagged with restriction enzyme sites for XbaI and KpnI. Fragments of the pYA3341 (pUC ori) and pYA3342 (pBR ori) plasmids minus the *S. Typhimurium* asdA gene were amplified by PCR with the primer pair P42F-KpnI and p42R-XbaI (see Table 3 below). After gel purification, fragments were ligated with T4 DNA ligase and transformed into the *E. piscicida* ΔasdA strain χ16000, and plated on LB agar plates. The recombinant plasmids were confirmed by restriction digestion with XbaI and KpnI and sequencing. The resulting plasmids were named pG8R8011, pG8R8012, pG8R8013, pG8R8014, pG8R8015, pG8R8016, pG8R8017 and pG8R8018 (FIG. 4).

TABLE 3

Primers for $Asd^+$ plasmid vectors construction

| Primer Name | Primer sequence (5'-3') |
|---|---|
| Pasd-F | CATTCTAGAAAATTCACTTGCGCATCGCGGC |
| SDasd-F | CATTCTAGATCACCATCCAAGGCAGGAGTGCATATG |
| Asd-F | CATTCTAGAGTGCATATGAAAAACGTTGGTT |
| SDasd-GTG-F | CATTCTAGATCCAAGGCAGGAGTGCATGTG |
| ASD-RV | CATGGTACCGACTAGAGCAGCAGCCTCAGC |
| p42F-KpnI | CATGGTACCAGACCTTCCATTCTGAAATGA |
| p42R-XbaI | CATTCTAGACTGTCAGACCAAGTT |

Since synthesis of high amounts of the AsdA protein interfere with the efficiency of the biosynthetic pathway for DAP, the asdA promoter was deleted when making high copy number vectors with pUC ori and pBR ori. In addition, the start codon was changed from ATG to GTG to reduce translation efficiency about 10-fold. The $Asd^+$ plasmids listed in FIG. 4 are also listed in Table 1).

χ16000 harboring the pG8R8018 $Asd^+$ vector possessing only the SD-asdA gene from *E. piscicida* with a modified start codon from ATG to GTG (FIG. 3) grew as well in the absence of DAP as the wild-type *E. piscicida* strain J118. The pG8R8018 $Asd^+$ vector possesses only the SD-asdA gene from *E. piscicida* with a modified start codon from ATG to GTG.

Figure 3:
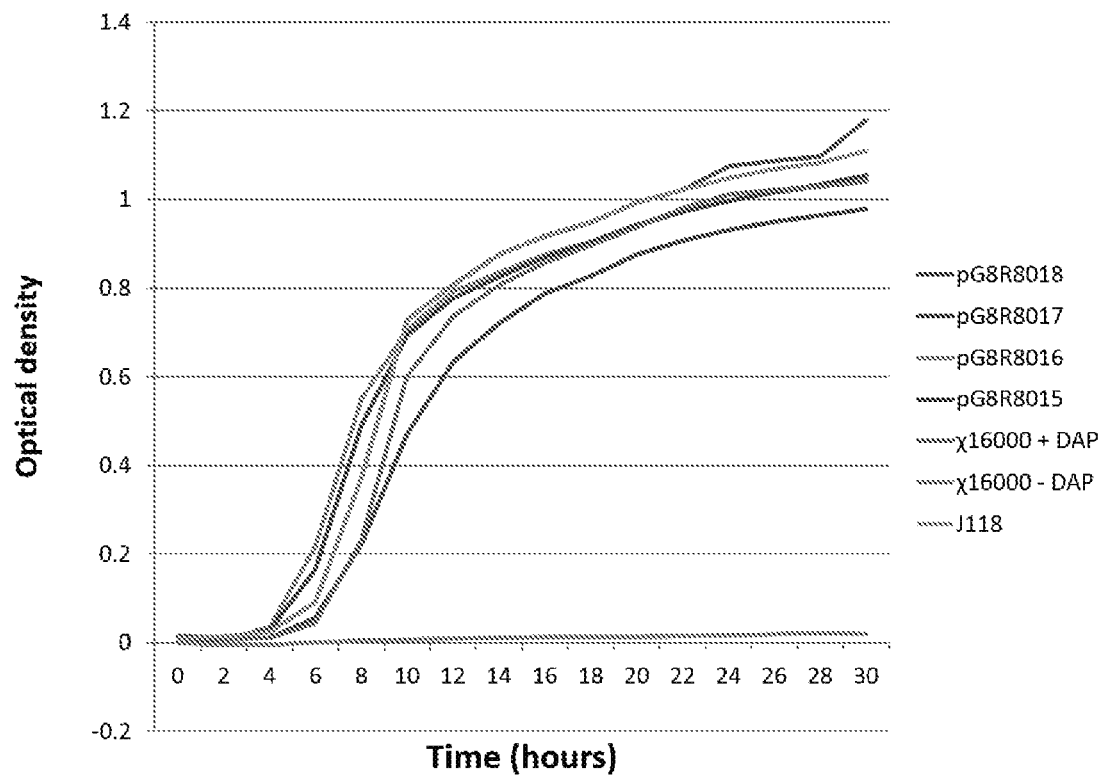
Figure 5:
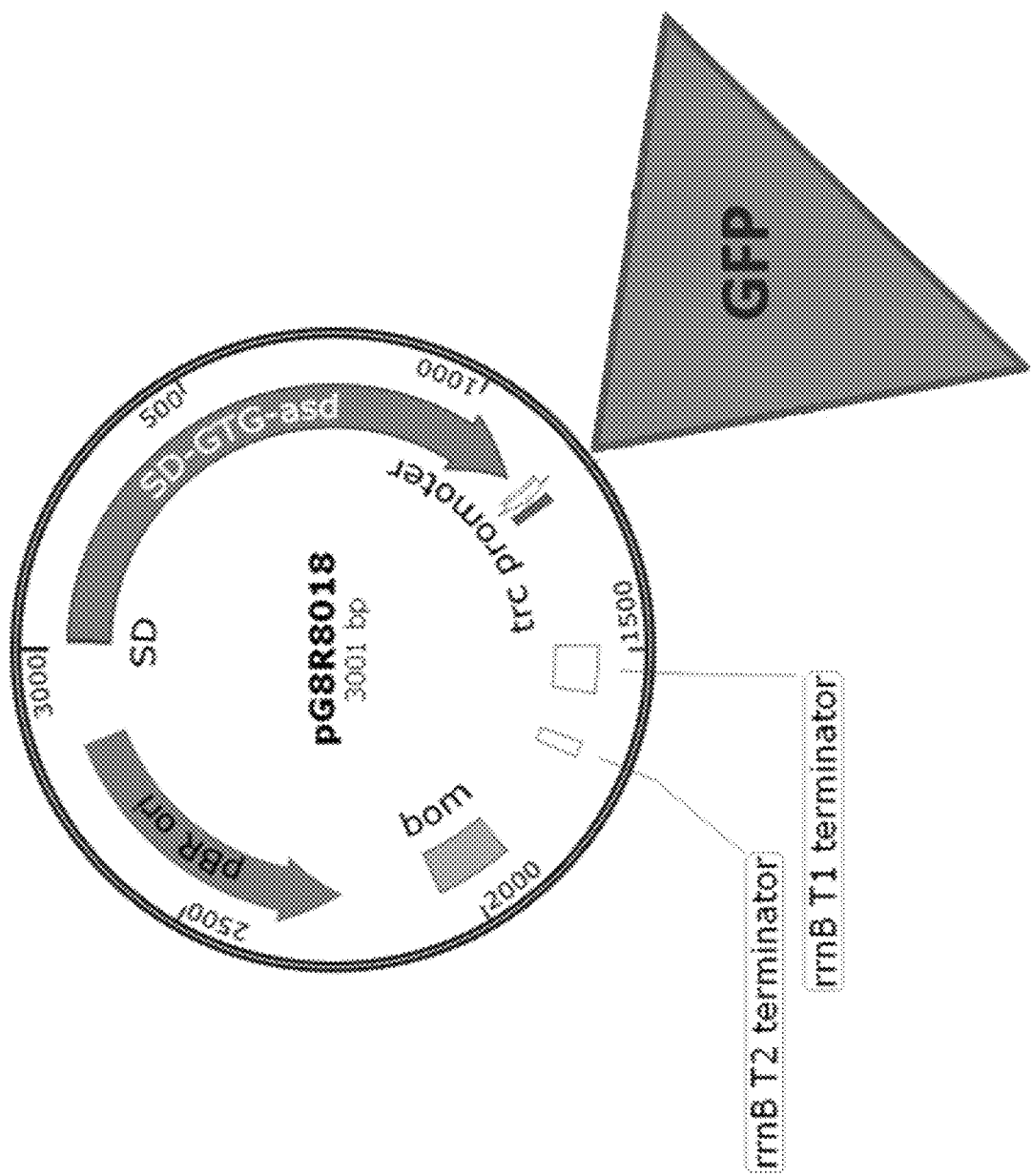
Figure 6A:
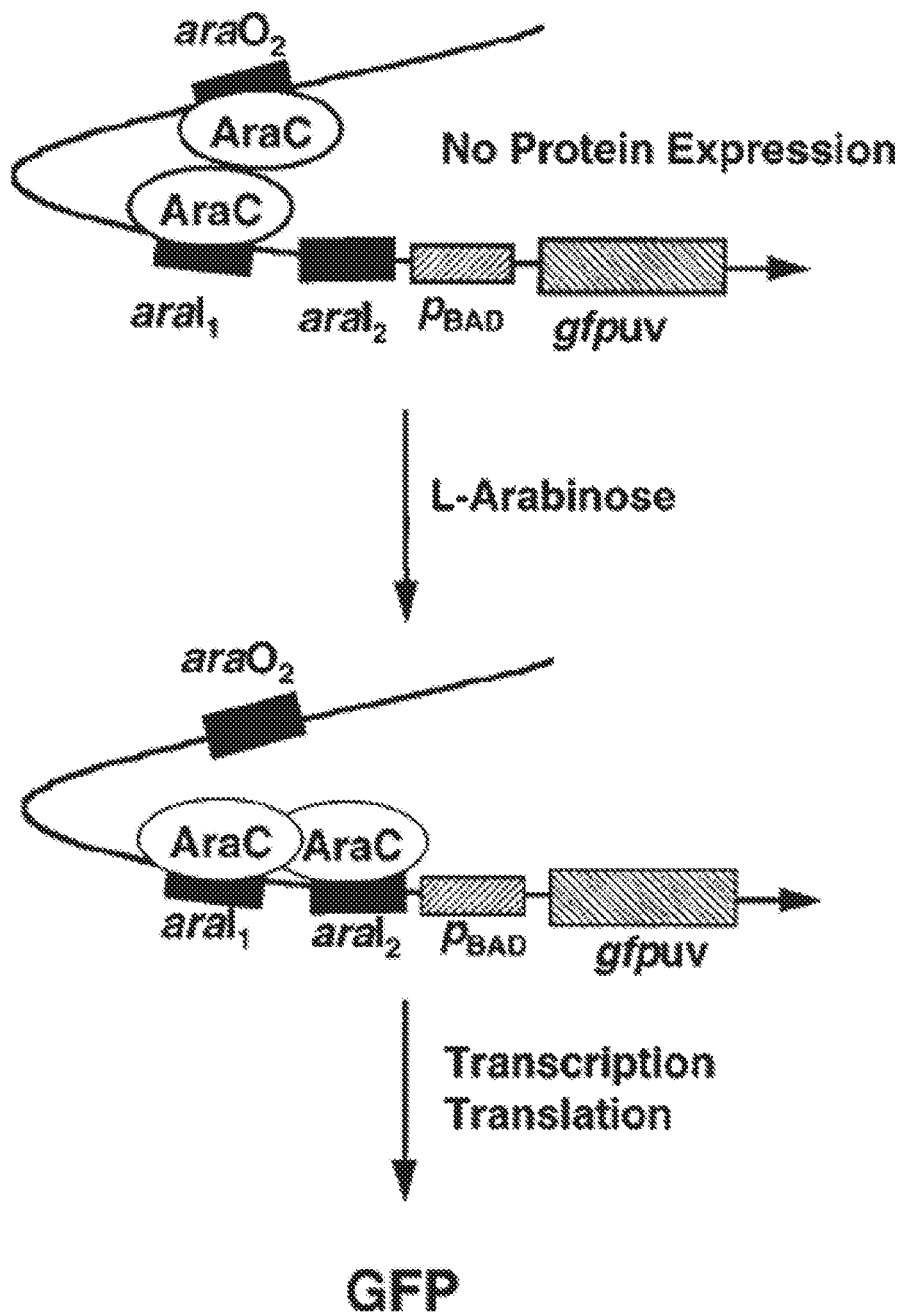
Figure 6B:
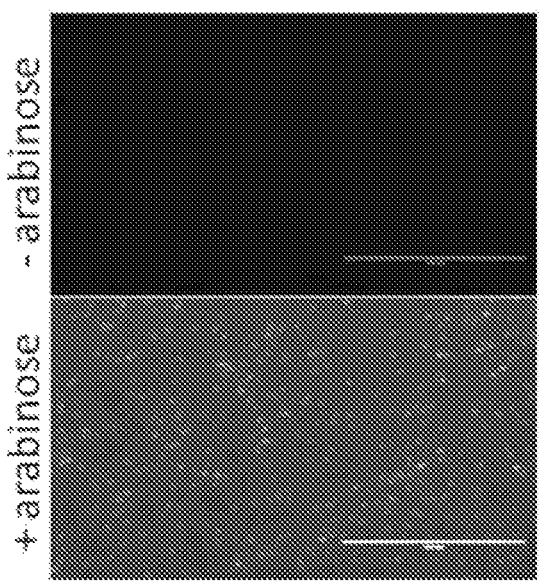
Figure 6C:
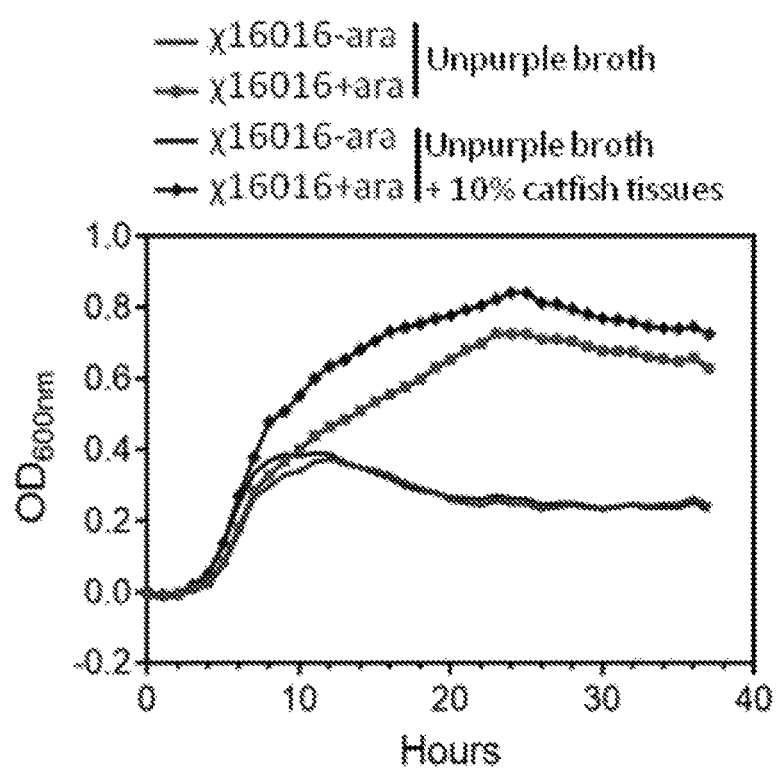

FIG. 3 is a graph showing complementation of the ΔasdA mutation in strain χ16000. FIG. 5 is an illustration of a pG8R8018 $Asd^+$ vector modified to express green florescent protein (GFP).

Example 2

Construction of *E. piscicida* Strains with Regulated Delayed Attenuation Phenotypes Recombinant bacterial vaccines must be fully attenuated for animal hosts to avoid inducing disease symptoms while exhibiting a high degree of immunogenicity.

Figure 7A:
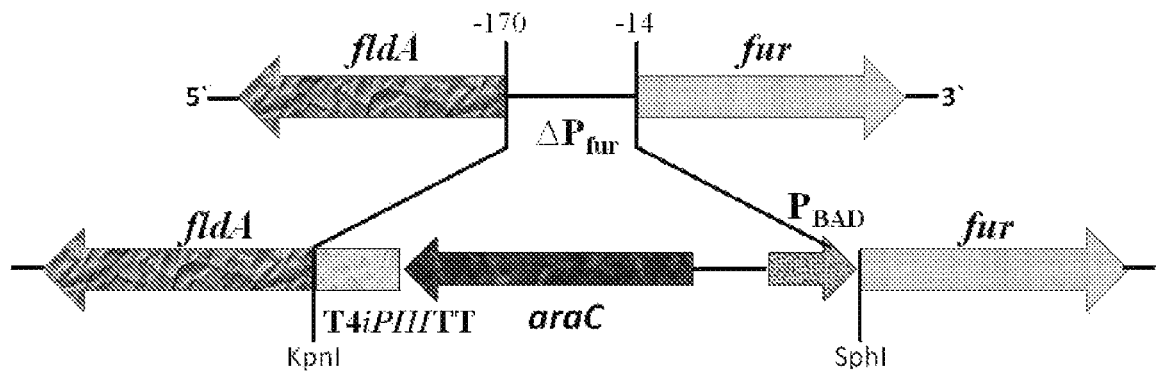
Figure 7B:
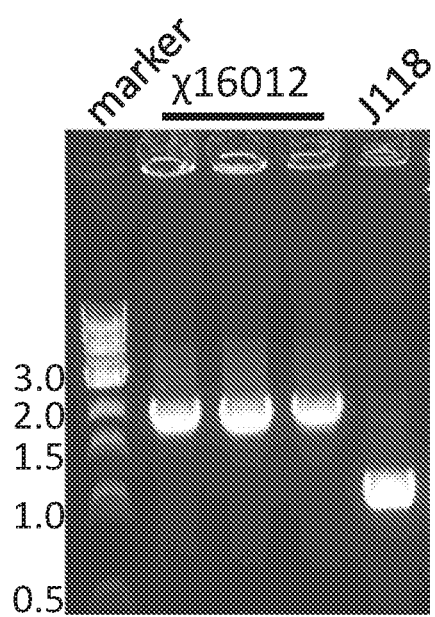

Many well-studied means for attenuating bacterial strains cause them to be more susceptible to host defense stresses than wild-type virulent strains and/or impair their ability to effectively colonize internal lymphoid tissues (see Curtiss, R. III, S. Y. Wanda, B. M. Gunn, X. Zhang, S. A. Tinge, V. Ananthnarayan, H. Mo, S. Wang, and W. Kong. 2009. *Salmonella enterica* serovar *Typhimurium* strains with regulated delayed attenuation in vivo. Infect. Immun. 77:1071-1082., which is incorporated by reference in its entirety as fully set forth here).

To achieve regulated delayed attenuation in vivo, a tightly regulated araC $P_{araBAD}$ cassette was substituted for the promoters of the *E. piscicida* fur and crp genes. To validate using this approach that works well in *E. coli* and *Salmonella*, the absence of arabinose in fish tissues was established (FIGS. 6A-6C). To evaluate the presence of arabinose in catfish tissues, pYA3700 encoding araC $P_{araBAD}$ gfp was electroporated into *E. piscicida* J118, which was then grown in media containing 10% macerated catfish flesh with or without 0.2% arabinose. Arabinose-dependent expression of GFP by *E. piscicida* was examined by fluorescence microscopy. GFP expression was observed in the culture supplemented with arabinose but not in medium without arabinose (FIG. 6B). The absence of arabinose was also confirmed in catfish tissues by using *E. piscicida* χ16016 ($\Delta P_{murA180}$::TT araC $P_{araBAD}$ murA) that depends on arabinose to replicate. It was found that χ16016 did not replicate and underwent muramic acid-less death by lysis in medium with macerated catfish tissues whereas χ16016 grew when this medium was supplemented with 0.2% arabinose (FIG. 6C). This indicates the absence of arabinose in the environment that RAEV will likely encounter. It was also determined that zebrafish tissues also lacked free arabinose.

To construct strains with the $\Delta P_{fur170}$::TT araC $P_{araBAD}$ fur deletion-insertion mutation (FIG. 7A), the primers listed in Table 4 below were used. A 470-bp *E. piscicida* DNA fragment containing the region upstream of the fur promoter was PCR amplified using the *E. piscicida* J118 genomic DNA as a template with primers fur1-KpnI and fur2-PstI. The FOR-amplified fragment was digested with KpnI and PstI and cloned into the KpnI-PstI site of vector pYA3700, which lies just upstream of the araC gene, Primer pYA3700-

FW, which binds to the just upstream region of the HindIII-SphI site in pYA3700 and primer fur2-PstI were used to screen plasmid isolates for inserts in the correct orientation. A PCR fragment of 525 bp, was amplified from the *E. piscicida* J118 genomic DNA, using upstream primer fur3-XhoI which contains the modified Shine-Dalgarno (SD) sequence "AGGAGG" and the downstream primer fur4-SphI. The PCR fragment was digested with XhoI and SphI and inserted into the XhoI and SphI site of intermediate plasmid described above. The resulting construct was confirmed by DNA sequence analysis. Then, a 2330 bp DNA fragment including araC $P_{araBAD}$ and fur 5' and 3' flanking region were amplified from the intermediate plasmid by using primers fur1-KpnI and fur4-SphI. The amplified product was cloned into the KpnI-SphI site of the suicide vector pRE112. The recombinant plasmids were screened by PCR and restriction digestion with KpnI and SphI enzymes and the resultant plasmid was named pG8R8024. To construct the *E. piscicida* $\Delta P_{fur170}$::TT araC $P_{araBAD}$ fur mutant, the suicide plasmid pG8R8024 was conjugationally transferred from *Escherichia coli* χ7213 to *E. piscicida* wild-type strains J118. Strains containing single-crossover plasmid insertions were isolated on BHI agar plates containing Col and Cm. Loss of the suicide vector after the second recombination between homologous regions (i.e., allelic exchange) was selected by using the sacB-based sucrose sensitivity counter-selection system. The colonies were screened for $Cm^S$, $Col^r$ and by PCR using primers fur1-KpnII and fur4-SphI. The resultant *E. piscicida* containing $\Delta P_{fur170}$::TT araC $P_{araBAD}$ fur mutation was named χ16012 and verified as shown in FIG. 7B.

TABLE 4

Primers for construction of construct strains with the $\Delta P_{fur170}$::TT araC $P_{araBAD}$ fur deletion-insertion mutation

| Primer Name | Primer sequence (5'-3) |
| --- | --- |
| Afr1-KpnI | catGGTACCTCTGCTGGGTATCCCCACCTGG |
| Afr2-Pst1r | catCTGCAGTGACGCAGCGAACTGCGCACT |
| Afr3-XhoI | catCTCGAGAGGAGGGAATCCGAATGACTGACAACAAC |
| Afr4-SphI | catGCATGCGCGCGCGGGTAAAAAAAACGG |

To construct strains with the $\Delta P_{crp68}$::TT araC $P_{araBAD}$ crp deletion-insertion mutation, primers listed in Table 5 below were used. A 557-bp DNA fragment containing the region upstream of the crp promoter was PCR amplified using the *E. piscicida* J118 genomic DNA as a template with primers crp1-HindIII and crp2-BglII. The PCR-amplified fragment was digested with HindIII and BglII and cloned into the HindIII-BglII site of vector pYA3700, which lies just upstream of the araC gene. Primer pYA3700-FW, which binds to the just upstream region of the HindIII-SphI site in pYA3700 and primer crp2-BglII were used to screen plasmid isolates for inserts in the correct orientation. A PCR fragment of 592 bp, was amplified from the *E. piscicida* J118 genomic DNA, using upstream primer crp3a-XhoI/crp3b-XhoI which contains the wild type/modified Shine-Dalgarno (SD) sequence "AGGAGG" and the downstream primer crp4-KpnI. The PCR fragment was digested with XhoI and KpnI and inserted into the XhoI and KpnI site of the intermediate plasmid described above. The resulting construct was confirmed by DNA sequence analysis. Then, a DNA fragment including araC $P_{araBAD}$ and crp 5' and 3' flanking region were amplified from the intermediate plasmid by using primers crp5-XmaI and crp4-KpnI primers. The amplified product was cloned into the XmaI-KpnI site of vector pRE112. The recombinant plasmids were screened by PCR and restriction digestion with XmaI and KpnI enzymes and the resultant plasmids was named pG8R8009 and pG8R8010. To construct the *E. piscicida* araC $P_{araBAD}$ crp and $\Delta P_{crp78}$::TT araC $P_{araBAD}$ crp mutant, the suicide plasmid pG8R8009 and pG8R8010 was conjugationally transferred from *Escherichia coli* χ7213 to *E. piscicida* wild-type strain J118. Strains containing single-crossover plasmid insertions were isolated on BHI agar plates containing Col and Cm. Loss of the suicide vector after the second recombination between homologous regions (i.e., allelic exchange) was selected by using the sacB-based sucrose sensitivity counter-selection system. The colonies were screened for $Cm^S$, $Col^r$ and by PCR using primers crp5-XmaI and crp4-KpnI. The resultant *E. piscicida* containing the $\Delta P_{crp68}$::TT araC $P_{araBAD}$ crp mutation was named χ16010 and $\Delta P_{crp78}$::TT araC $P_{araBAD}$ crp mutant named χ16011.

TABLE 5

Primers for construction of strains with the $\Delta P_{crp58}$::TT araC $P_{BAD}$ crp deletion-insertion mutation

| Primer Name | Primer sequence (5'-3') |
| --- | --- |
| Crp3a-XhoI | CGCCTCGAGGGATAAtagcgaATGgttctc |
| Crp3b-XhoI | CGCCTCGAGAGGAGGtagcgaATGgttc |
| Crp4-KpnI | CCCGGTACCtctgatcctccagcatcttc |
| Crp1-HindIII | CGCAAGCTTccgtccaatatcgaatacca |
| Crp2-BglII | CCCAGATCTtctatacccgcttcattcca |
| Crp5-XmaI | CGC-CCCGGGccgtccaatatcgaatacca |

The expression of these genes is dependent on arabinose provided during growth. Thus, following colonization of lymphoid tissues, the Fur and/or Crp proteins cease to be synthesized due to the absence of arabinose such that attenuation is gradually manifest in vivo to preclude induction of diseases symptoms.

Ferric uptake regulator (Fur) and cyclic AMP receptor protein (Crp) are global regulators for expression of genes encoding various virulence factors in Gram-negative bacteria (Choe et al., 2017).

Compared to the wild type a fur crp mutant exhibited retarded growth, decreased survival against oxidative stress and host serum, impaired ability to inhibit host immune responses, and attenuated tissue infectivity and overall virulence. The Δcrp mutant of *S. Typhimurium* was shown to be unable to ferment several sugars such as maltose (Curtiss et al., 2009).

Figure 8A:
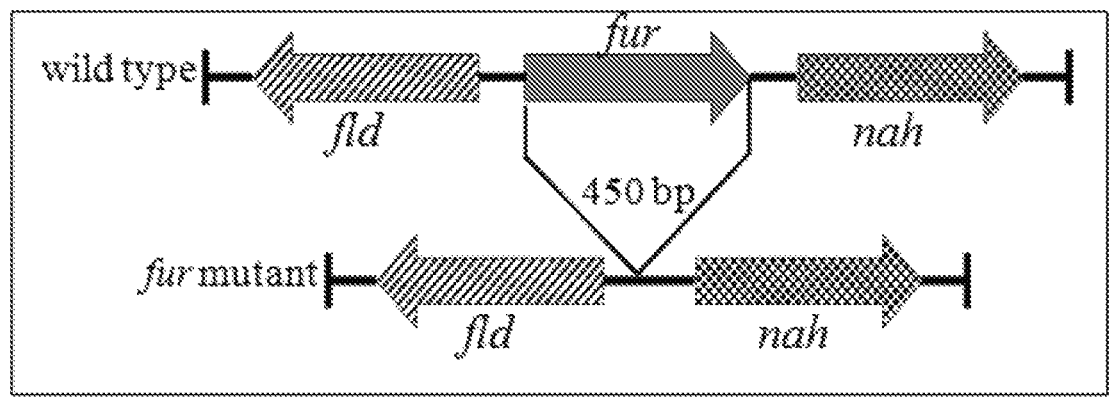
Figure 8B:
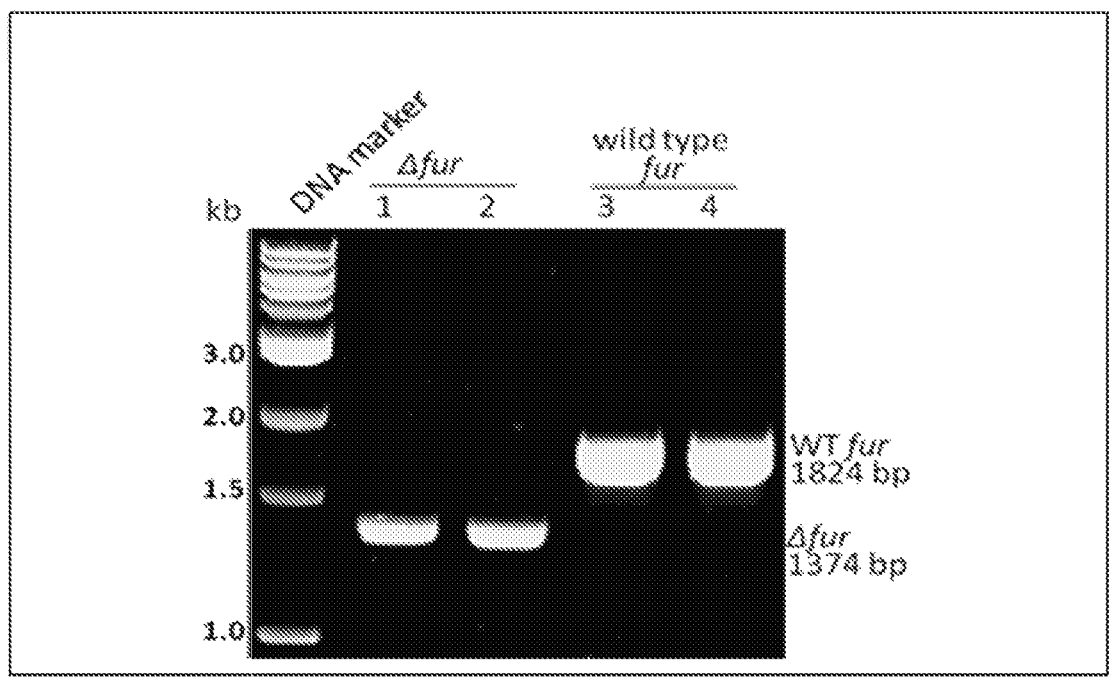
Figure 9:
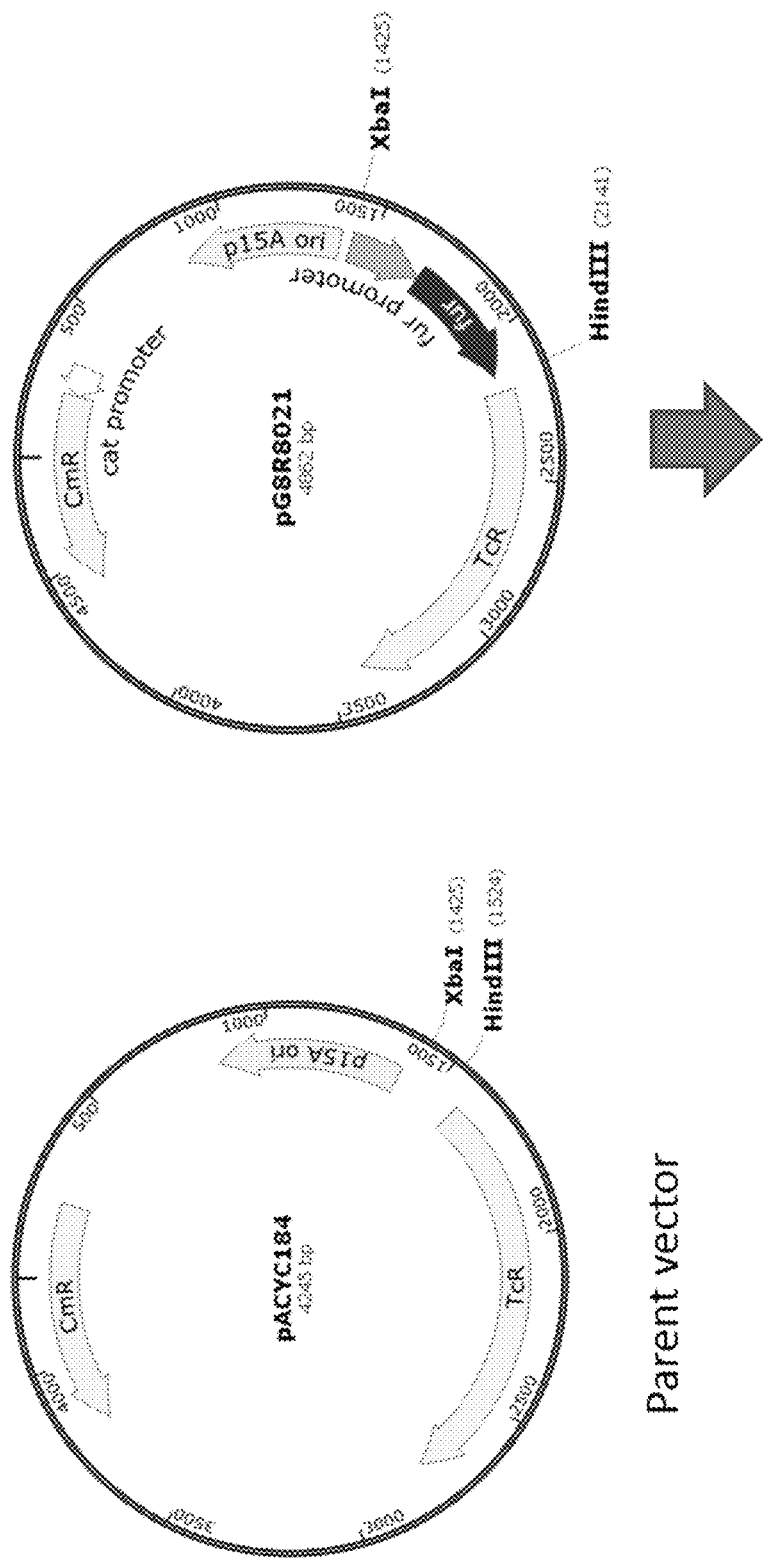

FIGS. 8A-8B are an illustration for genotype verification of $\Delta P_{fur170}$::TT araC $P_{araBAD}$ fur deletion-insertion mutation by PCR. FIGS. 8A-8B illustrate in-frame deletion of the fur gene in *E. piscicida*. FIG. 9 is an illustration of a fur complementation plasmid with the wild-type fur gene.

Figure 10A:
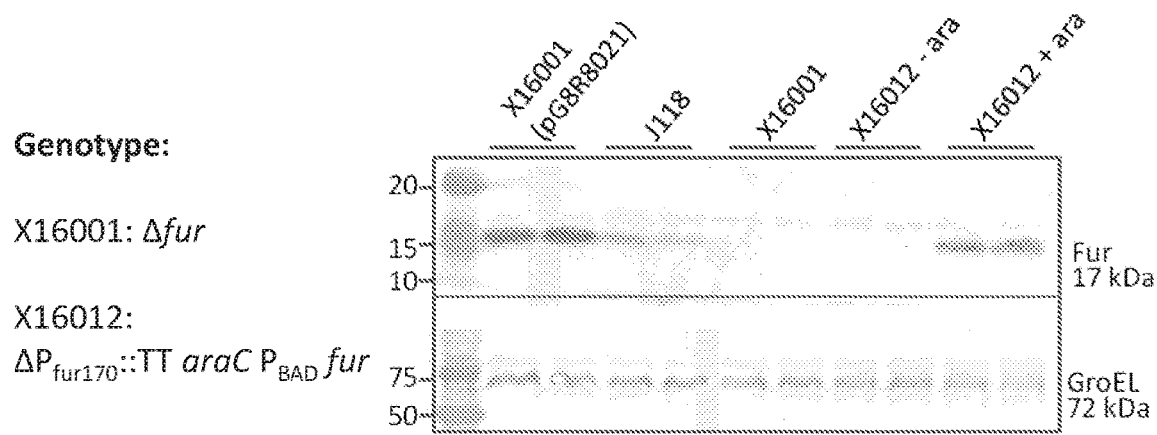
Figure 10B:
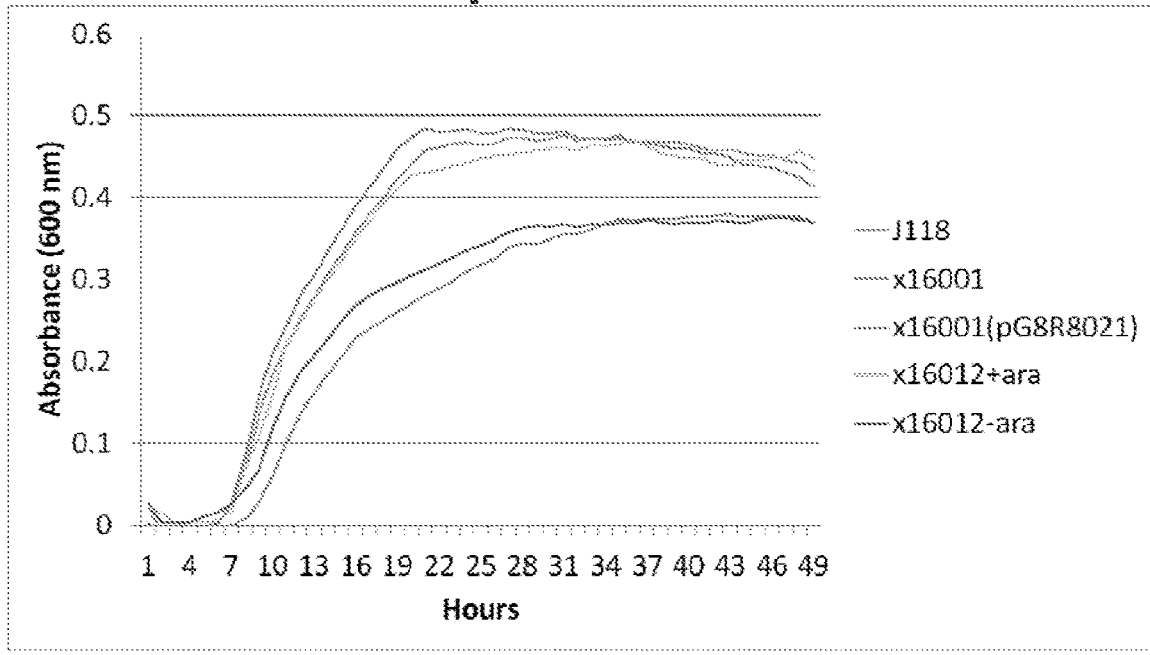

FIGS. 10A-10B show analysis of Fur protein synthesis and complementation using χ16001 vector (Δfur, with or without pG8R8018) and χ16012 vector ($\Delta P_{fur170}$:TT araC $P_{araBAD}$ fur, with or without arabinose). Synthesis of Fur is thus dependent on the presence of the wild-type fur gene or the presence of arabinose when Fur synthesis is dependent on the presence of arabinose.

Figure 11:
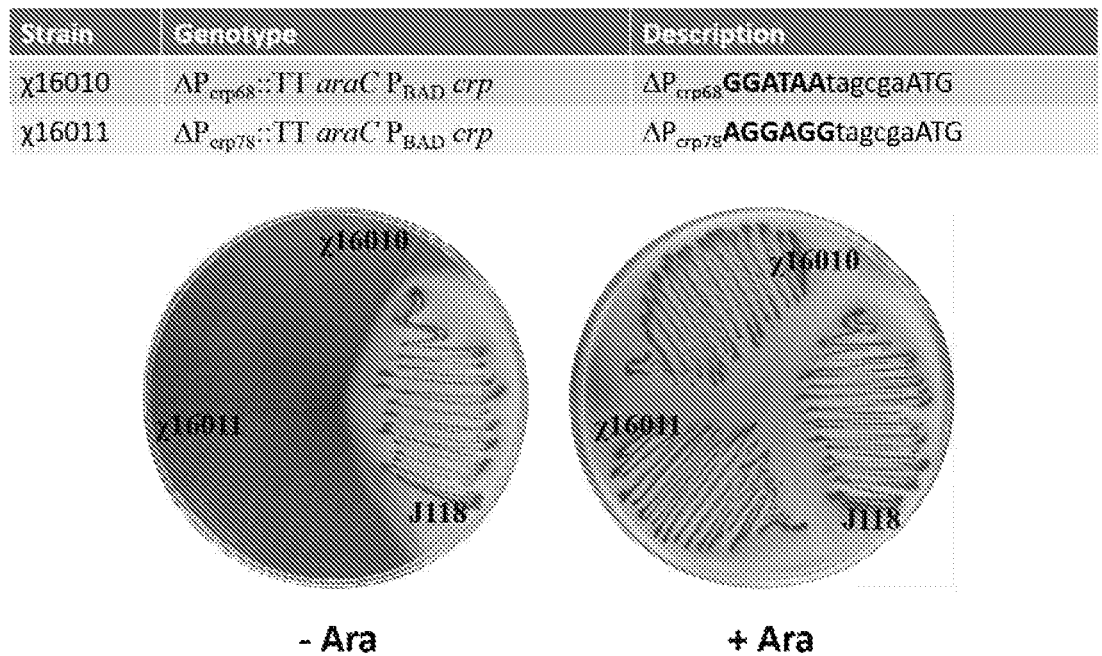

FIG. 11 shows wild-type, χ16001, and χ16012 vectors streaked on MacConkey maltose agar without and with 0.2% arabinose. The inability to ferment maltose in the absence of arabinose is due to the obligate requirement for the Crp protein to promote transcription of the genes encoding enzymes for uptake and metabolism of maltose.

Figure 14:
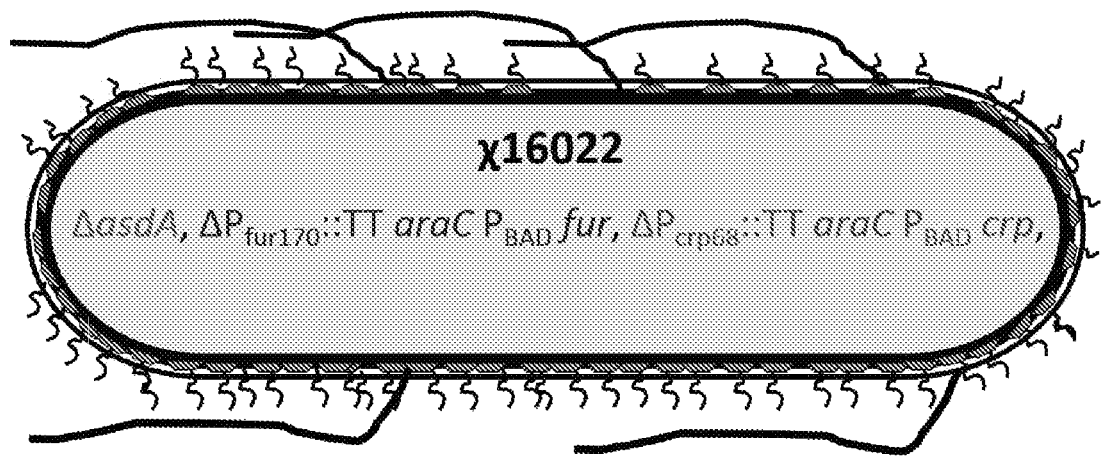
FIG. 14 illustrates a χ16022 construct that is ΔasdA, ΔP$_{fur170}$::TT araC P$_{BAD}$ fur, and ΔP$_{crp68}$::TT araC P$_{BAD}$ crp. This strain displays the regulated delayed attenuation phenotype and can be used to deliver synthesized protective antigens encoded on AsdA$_+$ plasmid vectors.

FIG. 14 illustrates a χ16022 construct that is ΔasdA, $\Delta P_{fur170}$:TT araC $P_{araBAD}$ fur, and $\Delta P_{crp68}$:TT araC $P_{araBAD}$ crp. This strain displays the regulated delayed attenuation phenotype and can be used to deliver synthesized protective antigens encoded on AsdA$^+$ plasmid vectors.

Example 3

Figure 12A:
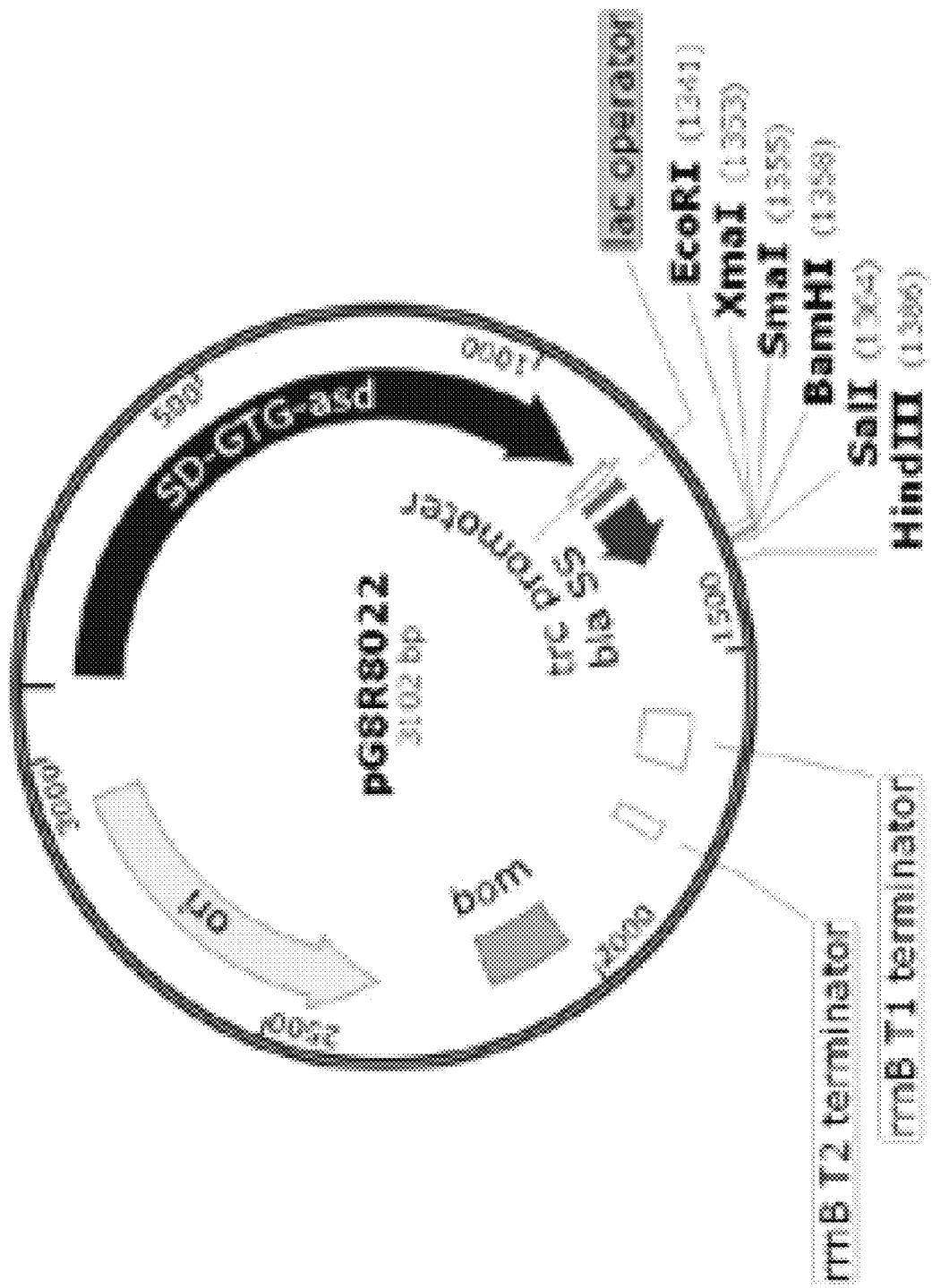
Figure 12B:
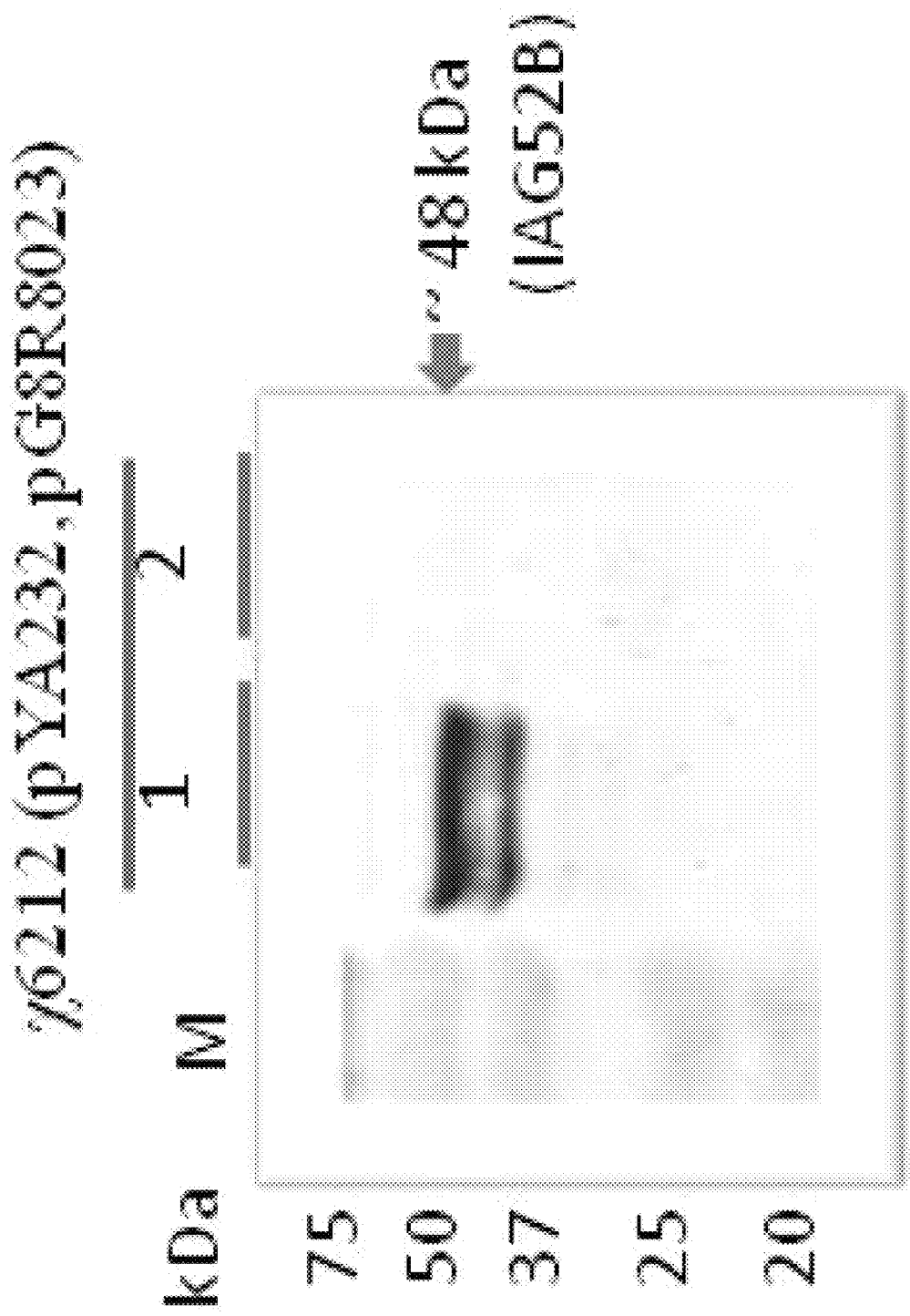
Figure 12C:
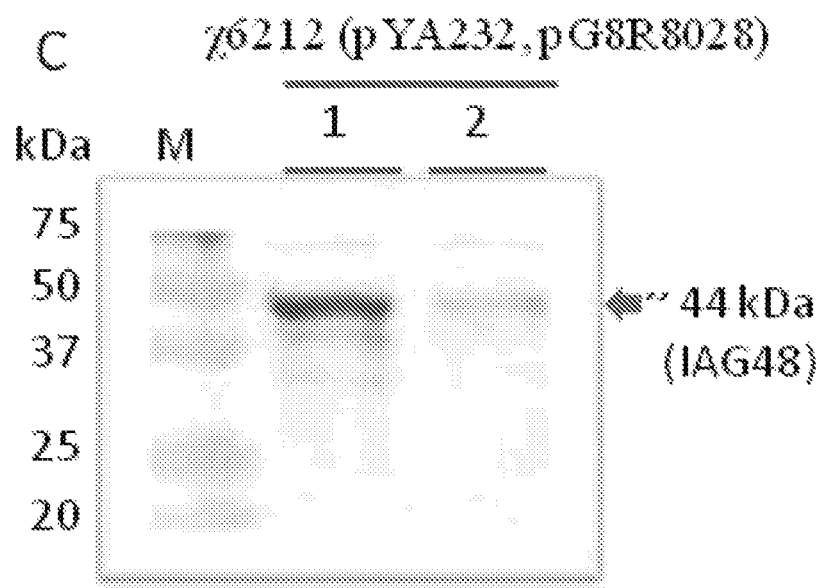
Figure 12D:
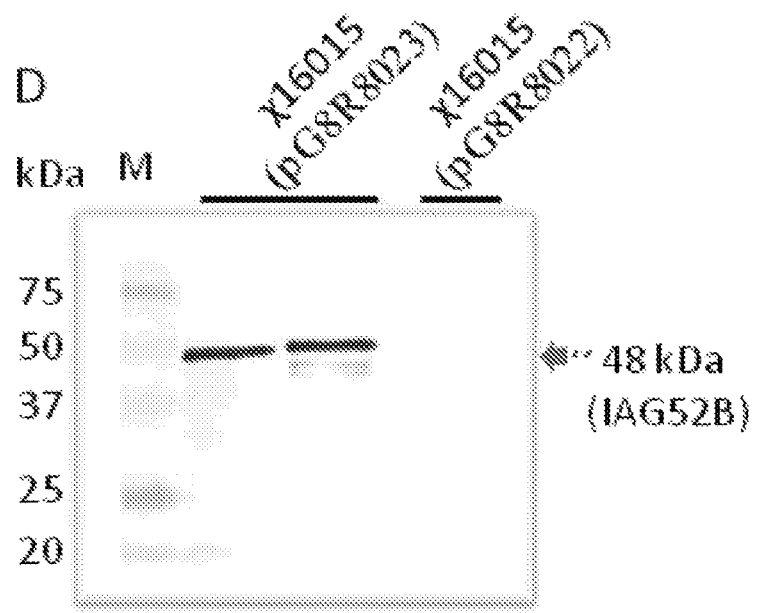
Figure 13:
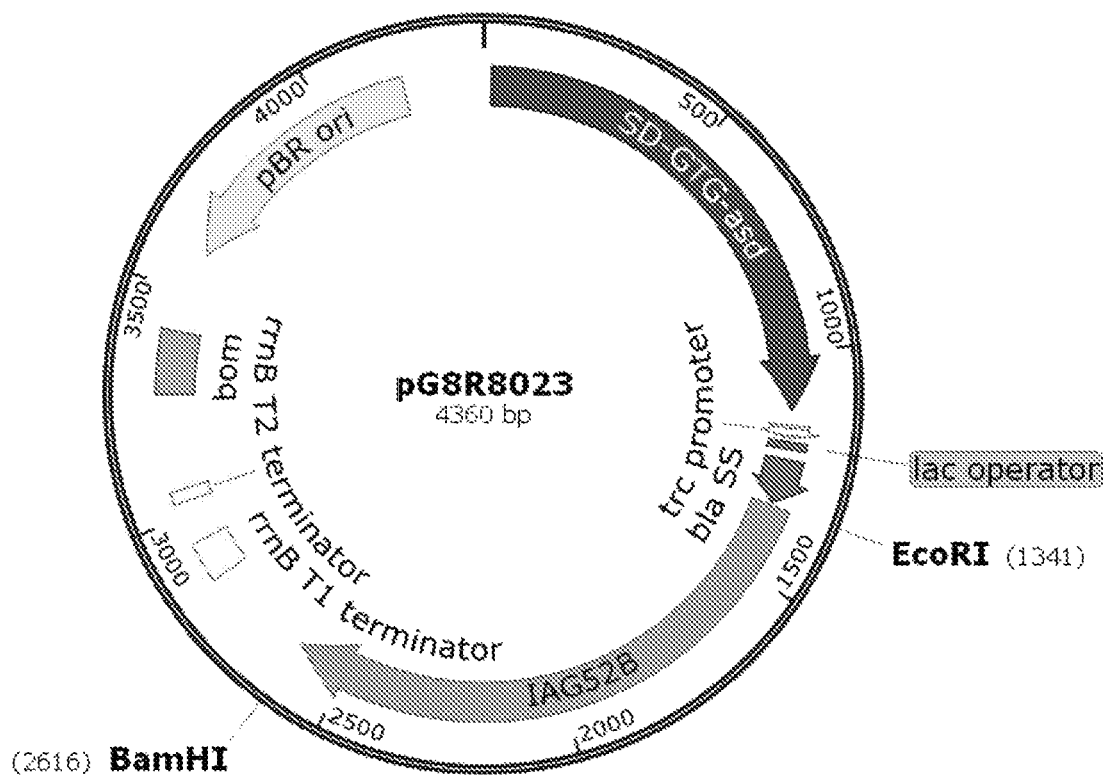

Synthesis of Ich Antigens IAG52B and IAG48 in RAEV Strains with Balanced-Lethal Asd$^+$ Vectors IGA52B i-antigen is most highly synthesized by serotype D Ich strains and IAG48 by serotype A Ich strains. Embodiments of codon-optimized sequences for these two I-antigens were cloned into an embodiment of a suitable parent vector, the *E. piscicida* Asd$^+$ plasmid parent vector pG8R8022 (FIG. 12A) that possesses a N-terminal optimized β-lactamase signal sequence. Embodiments of the resulting plasmids pG8R8023(IAG52B) and pG8R8028 (IAG48) were transformed into χ6212(pYA232). Table 2 below is a table of *E. piscicida* Asd$^+$ plasmids and relevant characteristics. χ6212 is a ΔasdA4 derivative of DH5α used for Asd$^+$ plasmid-construction by selecting for growth in the absence of DAP. pYA232 has a pSC101 replicon compatible with the pBR ori present in both plasmid constructs and also possesses the lacI$^q$ gene so that expression of genes under the control of the Asd$^+$ vector Ptrc promoter is repressed. This requires addition of inducer IPTG to relieve LacI repression and permit transcription of i-antigen encoding genes in both recombinant Asd$^+$ vectors. Growth of χ6212 (pYA232, pG8R8023) or χ6212(pYA232, pG8R8028) in LB broth with or without 1 mM IPTG was analyzed by western blotting with anti-IAG52B or anti-IAG48 polyclonal antibody. Bands of expected sizes were observed with the expected regulation by IPTG (FIG. 12B and FIG. 12C). To check synthesis of recombinant protein in *E. piscicida*, the plasmids pG8R8023, pG8R8028 and pG8R8022 (control vector) were electroporated into *E. piscicida* χ16015 (ΔasdA10 $\Delta P_{fur170}$::TT araC $P_{araBAD}$ fur). The synthesis of IAG52B by *E. piscicida* was confirmed by western blotting (FIG. 12D). Stability of all these Asd$^+$ vectors was analyzed in an *E. piscicida* (Δasd) host for more than 50 generations in presence and absence of DAP, and antigen synthesis was reconfirmed by western blotting after 50 generations. The results indicated that these vectors were stably maintained and enabled i-antigen synthesis in *E. piscicida* after 50 generations. FIG. 13 is an illustration of a vector construct encoding an embodiment of the IAG52B *Ichthyophthirius multifiliis* (Ich) antigen.

Example 4

Synthesis of Ich Antigen IAG52B in RAEV Strains with Balanced-Lethal Asd$^+$ Plasmid Vector

*Ichthyophthirius multifiliis* (Ich), which causes white spot disease in fresh water fish, is a protozoan parasite that causes significant disease problems for the U.S. channel catfish aquaculture industry. RAEVs have been constructed synthesizing Ich antigen (RAEV-Ich) IAG52B encoded by DNA sequences that have been codon optimized for high-level expression in *Edwardsiella*. As listed above, the stop codons that encode glutamine in Ich were exchanged for the CAG codons that specify this amino acid in *Edwardsiella*, FIG. 13 diagrams the pG8R8020 derivative of the Asd$_+$ pG8R8018 encoding the Ich i-antigen IAG52B.

Example 5

Construction of a Regulated Programmed Lysis System

Further information relating to construction of a regulated programmed lysis system can be found in Kong, \N., S. Y. Wanda, X. Zhang, W. Bollen, S. A. Tinge, K. L. Roland, and R. Curtiss III, 2008. Regulated programmed lysis of recombinant *Salmonella* in host tissues to release protective antigens and confer biological containment. Proc. Natl. Acad, Sci. USA 105:9361-9366.; Ameiss, K., S. Ashraf, W. Kong, A. Pekosz, W. H. Wu, D. Milich, J. N. Billaud, and Roy Curtiss III. 2010. Delivery of woodchuck hepatitis virus-like particle presented influenza M2e by recombinant attenuated *Salmonella* displaying a delayed lysis phenotype. Vaccine 28:6704-6713.; Ashraf, S., W. Kong, S. Wang, J. Yang, and R. Curtiss III. 2011. Protective cellular responses elicited by vaccination with influenza nucleoprotein delivered by a live recombinant attenuated *Salmonella* vaccine. Vaccine 29:3990-4002.; and Kong, W., M. Brovold, B. A. Koneneman, J. Clark-Curtiss, and R. Curtiss III. 2012. Turning self-destructing *Salmonella* into a universal DNA vaccine delivery platform. Proc. Natl, Acad. USA 109:19414-19419, the entireties of all of which are incorporated by reference in their entireties as fully set forth herein.

Figure 15:
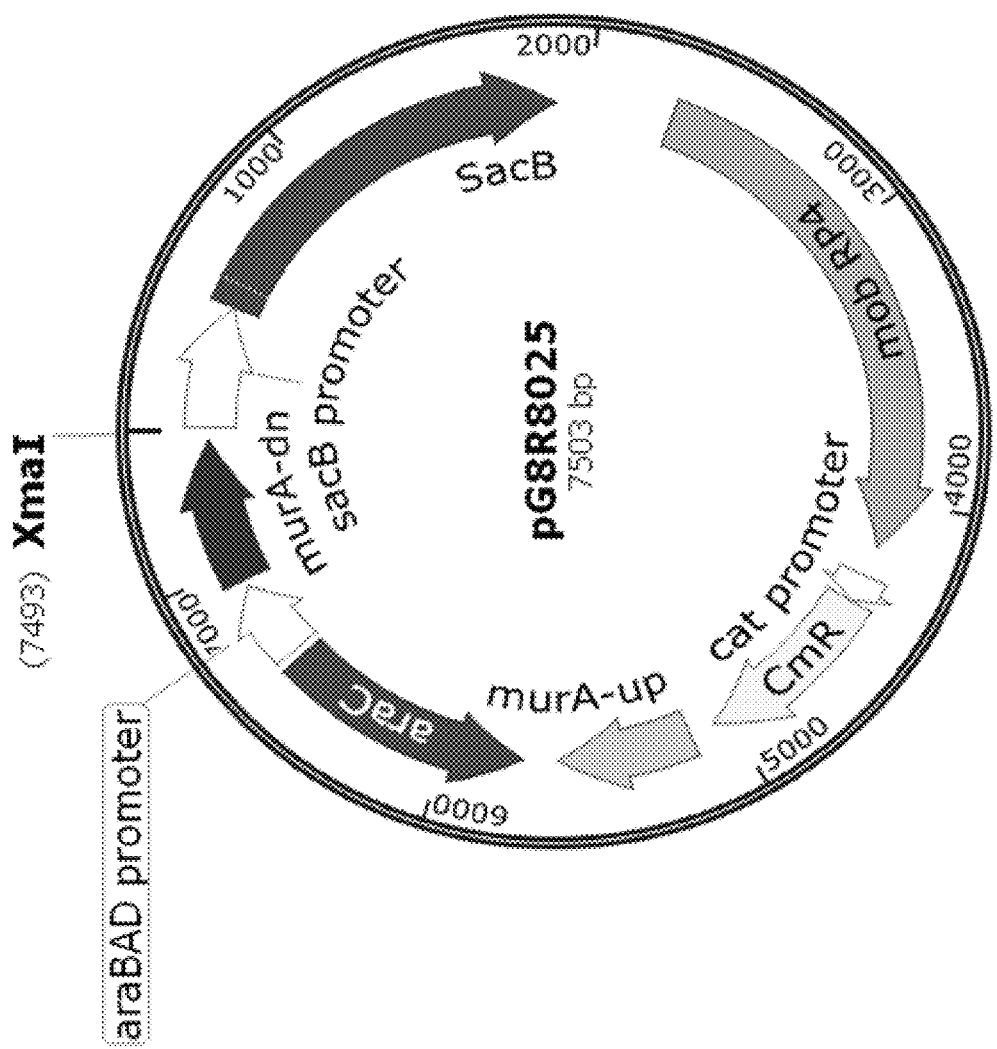
FIG. 15 is a map of suicide vector used for introduction of ΔP$_{murA180}$::TT araC P$_{araBAD}$ murA in *E. piscicida* strains.

Diaminopimelic acid (DAP) and muramic acid are essential components of the peptidoglycan layer of the bacterial cell wall (1). The asdA gene encodes an enzyme essential for DAP synthesis and the murA gene encodes the first enzyme in muramic acid synthesis (2,3). Unlike lethal asdA deletions, which can be overcome by the addition of DAP to the growth medium, murA deletions are lethal since they cannot be propagated by nutritional supplements since they are unable to take up phosphorylated products. Therefore, a conditional-lethal murA mutation was created by replacing the chromosomal murA promoter with the araC $P_{araBAD}$ activator-promoter by using suicide vector pG8R8025 (FIG. 15). The primers used in this work are listed in Table 6 below. A 595-bp DNA fragment containing the region upstream of the murA promoter was PCR amplified using the *E. piscicida* J118 genomic DNA as a template with primers MurA1-Sphl and MurA2-BgIII. The FOR-amplified fragment was digested with Sphl and BgIII and cloned into the Sphl-BgIII site of vector pYA3700, which lies just upstream of the araC gene. Primer pYA3700-FW, which binds to the just upstream region of the HindIII-Sphl site in pYA3700, and primer MurA2-BgIII were used to screen plasmid isolates for inserts with the correct orientation. A PCR fragment of 499 bp, was amplified from the *E. piscicida* J118 genomic DNA, using upstream primer MurA3-Kpnl, which contains the modified Shine-Dalgarno (SD) sequence "AGGAGG" and the downstream primer MurA4-EcoRl. The FOR fragments were digested with Kpnl and EcoRl and inserted into the Kpnl-EcoRl site of the intermediate plasmid described above. The resulting construct was confirmed by DNA sequence analysis. Then, the 2441 bp DNA fragment including araC $P_{araBAD}$ and murA 5' and 3' flanking region were amplified from the intermediate plasmid by using primers MurA1-SphI and MurA5-XmaI. The amplified product was cloned into the SphI-XmaI site of vector pRE112. The recombinant plasmids were screened by FOR and restriction digestion with SphI-XmaI enzymes and the resultant plasmid was named as pG8R8025. To construct the *E. piscicida* $\Delta P_{murA180}$::TT araC $P_{araBAD}$ murA mutant, the suicide plasmid pG8R8025 was conjugationally transferred from *Escherichia coli* χ7213 to *E. piscicida* wild-type strain J118, Strains containing single-crossover plasmid insertions were isolated on BHI agar plates containing Col and Cm. Loss of the suicide vector after the second recombination between homologous regions (i.e., allelic exchange) were selected by using the sacB-based sucrose sensitivity counterselection system. The colonies were screened for $Cm^S$, $Col^r$ and for growth only in the presence of arabinose. Colonies were screened by PCR using primers MurA1-SphI and MurA5-XmaI. The resultant *E. piscicida* containing the $\Delta P_{murA180}$::TT araC $P_{BAD}$ murA mutation was designated χ16016.

TABLE 6

Primers for construction of conditional-lethal murA mutation

| Primer name | Primer sequence (5'-3') |
|---|---|
| MurA1-SphI | CATGCATGCCGGGCATCACGTGTGTGGATATC |
| MurA2-BglII | CATAGATCTTCACAGACCGCTCAGCTTGCG |
| MurA3-KphI | CATGGTACCAGGAGGAATTAAATGGATAAATTTCGT |
| MurA4-EcoRI | CCGGAATTCCGCTGACCTTGTCCATCACGATA |
| MurA5-XmaI | CATCCCGGGCGCTGACCTTGTCCATCACGATA |

FIGS. 16A-16B shows the map of deletion-insertion mutation resulting in arabinose-regulated murA expression. The regulated lysis vaccine strain χ16016 grew well in LB broth supplemented with 0.02% arabinose but fails to grow in LB broth without arabinose (FIGS. 17 and 18). The $\Delta P_{murA180}$::TT araC $P_{araBAD}$ murA mutation was then introduced into the $\Delta asd$ strain χ16000 using suicide vector technology to yield χ16017. As expected, growth of χ16017 was dependent on both DAP and arabinose. The regulated programmed cell lysis is achieved by using χ16017 and complementing the two mutations (asdA and murA) by a plasmid vector pYA4763 that possesses asdA and murA genes under control of the araC $P_{araBAD}$ cassette (FIG. 19). In the presence of arabinose, the plasmid encoded copies of asdA and murA and the chromosomally encoded murA are transcribed from their respective $P_{araBAD}$ promoters, allowing for bacterial growth. In the absence of arabinose, the $P_{araBAD}$ promoters cease to be active, with no further synthesis of AsdA and MurA. These concerted activities lead to cell lysis. As expected, growth of χ16017 was dependent on both DAP and arabinose (FIG. 20).

Example 6

Determination of $LD_{50}$ of Wild-Type *Edwardsiella piscicida* (J118) Strain by Intracoelomic (I.c.) Injection or by Bath Immersion Cultured *E. piscicida* cells were harvested by centrifugation (5,000×g, 10 min) and resuspended in BSG (pH 7.4). Bacterial concentrations were adjusted by using a spectrophotometer. Viable bacterial cells were counted by culture on agar plates after serial dilution. Adult zebrafish (average weight, 0.3 g) were anesthetized by 100 mg/L tricaine methane sulfonate (MS-222, Sigma) and then injected intracoelomically (i.c.) with 10 μl volumes of bacterial suspensions ranging from $10^3$ to $10^6$ colony forming units (CFU) per fish and a control fish group was inoculated with 10 μl of sterile phosphate-buffered saline containing 0.01% gelatin (BSG). The insulin syringes with BD ultra-fine needle were used to inject the fish. During the experiments, the fish were observed daily, and mortalities were monitored for 15 days. The $LD_{50}$ values were calculated by the method of Reed & Muench (1938). The wild-type strain J118 was pathogenic to zebrafish. The $LD_{50}$ value by the i.c. route was $1\times10^4$ CFU per fish (FIG. 21).

Example 7

Determination of $Ld_{50}$ of Wild-Type *Edwardsiella Piscicida* (J118) Strains by Bath Infection Zebrafish were immersed in a solution of J118 containing $10^5$ to $10^9$ CFU/ml for 2 hours. During the experiment, the fish were observed daily. The $LD_{50}$ was calculated by the method of Reed-Muench. The $LD_{50}$ value by bath immersion was $1\times10^7$ CFU/ml (FIG. 22).

Example 8

Attenuation of Mutant Strains in Bath Immersion Immunized Zebrafish

Virulence of the *E. piscicida* Δfur (χ16001), χ16001 (pG8R8021), $\Delta P_{fur170}$:TT araC $P_{araBAD}$ fur (χ16012), $\Delta P_{crp68}$::TT araC $P_{araBAD}$ crp (χ16010) strains were evaluated in zebrafish. Zebrafish were immersed in solutions of the above strains containing $10^9$ CFU/ml for 2 hours (100-fold more than the $LD_{50}$ for J118). During the experiments, the fish were observed daily. The percentage of survival were, BSG (control): 100%; χ16010: 85%; χ16012: 82%; χ16001:79%, χ16001(pG8R8021): 10% and J118: 5%. Our result indicated that, Δfur, $\Delta P_{fur170}$::TT araC $P_{araBAD}$ fur and $\Delta P_{crp68}$:TT araC $P_{araBAD}$ crp mutations attenuate the wild-type *E. piscicida* strain (FIG. 23).

REFERENCES

1. Van Heijenoort J (1994) in Bacterial Cell Wall, eds Ghuysen J M, Hackenbeck R (Elsevier, Amsterdam), pp 39-54,
2. Black S, Wright N G (1955) Aspartic-semialdehyde dehydrogenase and aspartic semialdehyde. J Biol Chem 213:39-50.
3. Brown E D, Vivas E I, Walsh C T, Kolter R (1995) MurA (MurZ), the enzyme that catalyzes the first committed step in peptidoglycan biosynthesis, is essential in *Escherichia coli*. J Bacteriol 177:4194-4197.

Example 9

Use of RAEV Construct to Protect Against Ich Infections

Based on the foregoing Examples, the Asd⁺ plasmids (pG8R8018, pG8R8022, pG8R8023, pYA4763, pG8R110, pG8R111 and pG8R114) encoding the IAG48A, IAG52A and IAG52B protective i-antigens can be introduced into the E. piscicida vaccine vector strain χ16022 with the ΔasdA10 mutation and the regulated delayed attenuation mutations (ΔP$_{fur170}$::TT araC P$_{araBAD}$ fur; □P$_{crp68}$::TT araC P$_{araBAD}$ crp). More specifically, Asd$^+$ recombinants (RAEV-Ich) can be selected by plating on LB agar lacking DAP. After complete characterization and determining normal growth and stability of plasmid maintenance for over 50 generations when grown under permissive conditions in LB broth with DAP, immunization studies can be conducted in zebrafish analogous to those described in Example 7. Bath immunization comparing doses can be used with $10^6$, $10^9$ and $10^{10}$ CFU/ml in the bath immersion medium. After 2 h, fish can be transferred to fresh water and 4 weeks later challenged with Ich parasites. In additional studies, the time after primary immunization can be varied as can the dose of Ich parasites used for challenge. In additional studies, transfer of Ich from Ich-infected zebrafish to RAEV-Ich immunized versus non-immunized zebrafish can be studied when permitted to co-habit in the same tank over a 3 to 6 week period.

In further studies, the sequences encoding the IAG48A, IAG52A and IAG52B antigens can be inserted into the regulated delayed lysis vectors pYA4763, pG8R111 and pG8R114 (Table 2) and the recombinant plasmids fully characterized in the E. coli host χ6212. They can then be transferred to the E. piscicida strain χ16025 which has the regulated delayed attenuation attribute due to the ΔP$_{fur170}$:: TT araC P$_{araBAD}$ fur mutation, displays regulated delayed antigen synthesis due to the ΔP$_{lacI28}$::TT araC P$_{araBAD}$ lacI mutation and has the regulated delayed lysis in vivo phenotype due to the ΔP$_{murA180}$::TT araC P$_{araBAD}$ murA and ΔasdA10 mutations (when complemented with a lysis plasmid that has araC P$_{araBAD}$ regulation of both GTG-murA and GTG-asdA). These constructs after complete characterization can be used in repeat immunization evaluation studies as described above. Based on previously described studies with Salmonella vectored strains, the RAEV-Ich constructs displaying regulated delayed lysis may be more efficacious in inducing protective immunity against Ich infections than the RAEV-Ich constructs that do not undergo regulated lysis.

Subsequent studies can be conducted in catfish in the same manners as we previously evaluated E. ictaluri vaccine strains in catfish.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A genetically modified antibiotic-sensitive recombinant derivative of the piscine-restricted Gram-negative *Edwardsiella piscicida* capable of invasion into, or infecting, marine and fresh-water fish species that displays:
 (i) a regulated delayed manifestation of attenuation in vivo, wherein the bacterium comprises a chromosomally integrated regulatable promoter operably linked to a nucleic acid sequence encoding an attenuation protein such that transcription of the nucleic acid sequence encoding the attenuation protein occurs in a permissive environment but ceases in a non-permissive in vivo environment due to inclusion of one or more of the mutations selected from the group consisting of $\Delta P_{fur}$::TT araC $P_{araBAD}$fur, $\Delta P_{crp}$::TT araC $P_{araBAD}$ crp, ΔP$_{rfaH}$::TT araC P$_{araBAD}$ rfaH, ΔP$_{pstS}$::TT araC P$_{araBAD}$ pstS, ΔP$_{rfaD}$::TT araC P$_{araBAD}$ rfaD, and ΔP$_{murA}$::TT araC P$_{araBAD}$ murA;

(ii) a regulated delayed expression in vivo of at least one heterologous codon-optimized nucleic acid sequence encoding an antigen, wherein the bacterium comprises at least one chromosomally integrated nucleic acid sequence encoding a repressor operably linked to a regulatable promoter and an extra-chromosomal plasmid vector comprising at least one nucleic acid sequence encoding a protective antigen operably linked to a promoter regulated by a repressor, such that the expression of the nucleic acid sequence encoding the antigen is repressed during in vitro growth of the bacterium, but the bacterium is capable of high level expression in vivo; and (iii) a regulated delayed lysis in vivo phenotype that constitutes a balanced-lethal vector-host with regulatable asdA and/or murA plasmid vector genes and chromosomal ΔasdA and regulatable murA genes to confer biological containment, wherein the bacterium is able to synthesize components of the peptidoglycan cell wall layer under permissive conditions and unable to do so under non-permissive in vivo conditions.

2. The bacterium of claim 1, wherein the bacterium elicits an immune response against a fish pathogen other than Edwardsiella piscicida in a host.

3. The bacterium of claim 2, wherein the fish pathogen is a bacterial, viral, fungal or parasitic pathogen of fish.

4. The bacterium of claim 1, wherein the bacterium is able to synthesize components of the peptidoglycan cell wall layer under permissive conditions and unable to do so under non-permissive in vivo conditions.

5. The bacterium of claim 1, wherein the bacterium is capable of the regulated expression of at least one heterologous nucleic acid encoding an antigen, wherein the bacterium comprises at least one chromosomally integrated nucleic acid sequence encoding a repressor.

6. The bacterium of claim 3, wherein the protective antigens are encoded by genetic sequences from the parasite Ichthyophthirius multifiliis that have been codon modified for optimal synthesis of protein antigens with amino acid sequences of the protein antigens synthesized by Ichthyophthirius multifiliis.

7. The bacterium of claim 2, wherein the protective antigen comprise Ichthyophthirius multifiliis immobilization antigen precursor (IAG48), Ichthyophthirius multifiliis immobilization antigen isoform (IAG52A or IAG52B), or a combination thereof.

8. The bacterium of claim 1, wherein the bacterium further comprises
at least one chromosomally integrated nucleic acid sequence encoding a repressor operably linked to a regulatable promoter, and
a vector comprising at least one nucleic acid sequence encoding a protective antigen operably linked to a promoter regulated by the repressor, such that the expression of the nucleic acid sequence encoding the antigen is repressed during in vitro growth of the bacterium, but the bacterium is capable of high-level expression in vivo.

9. The recombinant bacterium of claim 1, wherein the bacterium further comprises at least one mutation selected from the group consisting of: ΔasdA, Δfur, Δpmi, Δcrp, ΔznuA, ΔgalE, ΔwaaL, ΔP$_{rfaH}$::TT araC P$_{araBAD}$ rfaH, ΔP$_{crp}$::TT araC P$_{araBAD}$ crp, ΔphoP, ΔP$_{rfaD}$::TT araC P$_{araBAD}$ rfaD, and ΔP$_{lacI}$::TT araC P$_{araBAD}$ lacI.

10. The bacterium of claim 1, wherein the bacterium is a non-auxotroph.

11. A method of eliciting an immune response in a fish, the method comprising administering a bacterium of claim 1 to the fish.

12. The method of claim 11, wherein the immune response is a protective immune response.

13. The method of claim 11, wherein the method further comprises delivering a bolus of antigen to the fish, wherein delivering a bolus of antigen comprises lysing the Edwardsiella bacterium after bacterial delivery to the fish.

14. The method of claim 11, wherein administering is one or more of administering by bath immersion, oral administration, or intracoelomic administration.

15. The method of claim 11, wherein the fish is a teleost fish.

16. The method of claim 11, wherein the fish is a farmed teleost fish.

17. A genetically modified Edwardsiella piscicida bacterium displaying a regulated delayed manifestation of attenuation in vivo, able to synthesize and deliver protective antigens encoded by genes from heterologous pathogens and capable of infecting fresh water and marine fish to deliver such synthesized protective antigens,
wherein the bacterium comprises a chromosomally integrated regulatable promoter operably linked to a nucleic acid sequence encoding an attenuation protein such that transcription of the nucleic acid sequence encoding the attenuation protein occurs in a permissive environment, but ceases in a non-permissive in vivo environment, and
wherein one of the regulated genes required for virulence leads to the eventual death by lysis of the genetically modified bacterium in a non-permissive in vivo environment.

18. A genetically modified Edwardsiella piscicida bacterium displaying a balanced-lethal vector-host phenotype wherein the bacterium possesses one or more chromosomal mutations that would preclude synthesis of essential unique constituents of the peptidoglycan layer of the bacterial cell wall under non-permissive in vivo conditions and a plasmid vector that possesses regulatable genes to complement the chromosomal mutations but cease to do so under non-permissive in vivo conditions leading to death by lysis.

19. The bacterium of claim 17, wherein the protective antigens are encoded by genetic sequences from the parasite Ichthyophthirius multifillis.

20. The bacterium of claim 1, wherein the bacterium comprises a chromosomally integrated regulatable promoter operably linked to a nucleic acid sequence encoding an attenuation protein such that transcription of the nucleic acid sequence encoding the attenuation protein occurs in a permissive environment, but ceases in a non-permissive in vivo environment.

21. The bacterium of claim 1, wherein the protective antigens are encoded by genetic sequences from the parasite Ichthyophthirius multifiliis.

22. A genetically modified antibiotic-sensitive recombinant derivative of the piscine-restricted gram-negative Edwardsiella piscicida bacterium capable of invasion into or infecting marine and fresh-water fish species that displays (i) a regulated delayed manifestation of attenuation in vivo wherein the bacterium comprises a chromosomally integrated regulatable promoter operably linked to a nucleic acid sequence encoding an attenuation protein such that transcription of the nucleic acid sequence encoding the attenuation protein occurs in a permissive environment, but ceases in a non-permissive in vivo environment, (ii) a regulated delayed expression in vivo of at least one heterologous codon-optimized nucleic acid sequence encoding an antigen wherein the bacterium comprises at least one chromosomally integrated nucleic acid sequence encoding a repressor operably linked to a regulatable promoter, and an extra-chromosomal plasmid vector comprising at least one nucleic acid sequence encoding a protective antigen operably linked to a promoter regulated by the repressor, such that the expression of the nucleic acid sequence encoding the antigen is repressed during in vitro growth of the bacterium, but the bacterium is capable of high level expression in vivo, and (iii) a regulated delayed lysis in vivo phenotype that constitutes a balanced-lethal vector-host to confer biological containment wherein the bacterium is able to synthesize components of the peptidoglycan cell wall layer under permissive conditions and unable to do so under non-permissive in vivo conditions.

23. The recombinant bacterium of claim 1, wherein the repressor is LacI and the bacterium further comprises a $P_{lacI}$::TT araC $P_{araBAD}$ lacI or ΔrelA::TT araC $P_{araBAD}$ lacI deletion-insertion mutation.

* * * * *

SEQUENCE LISTING

```
<160> NUMBER OF SEQ ID NOS: 16

<210> SEQ ID NO 1
<211> LENGTH: 1329
<212> TYPE: DNA
<213> ORGANISM: Ichthyophthirius multifiliis
<220> FEATURE:
<221> NAME/KEY: misc_feature
<222> LOCATION: (1)..(1329)
<223> OTHER INFORMATION: IchIAG48 (GenBank: AF140273.1)

<400> SEQUENCE: 1
atgaaatata atattttatt aatttttaatt atttctttat ttattaatga attaagagct      60
gttccatgtc ctgatggtac ttagactcaa gctggattga ctgatgtagg tgctgctgat     120
cttggtactt gtgttaattg cagacctaat ttttactata atggtggtgc tgcttaagga     180
gaagctaatg gtaattaacc tttcgcagca aataatgctg ctagaggtat atgtgtacca     240
tgccaaataa acagagtagg ctctgttacc aatgcaggtg acttagctac tttagccaca     300
taatgcagta cttaatgtcc tactggcact gcacttgatg atggagtgac agatgttttt     360
gatagatcag ccgcataatg tgttaaatgc aaacctaact tttactataa tggtggttct     420
ccttaaggtg aagctcctgg cgtttaagtt tttgctgctg gtgctgccgc tgcaggtgtt     480
gctgccgtta ctagttaatg tgtaccttgc caactaaaca aaaacgattc tcctgccact     540
gcaggtgcct aagctaattt agccacataa tgtagcaatt aatgtcctac tggcactgta     600
cttgatgatg gagtgacact tgtttttaat acatcagcca cattatgtgt taaatgcaga     660
cctaactttt actataatgg tggttctcct taaggtgaag ctcctggcgt ttaagttttt     720
gctgctggtg ctgccgctgc aggtgttgct gccgttacta gttaatgtgt accttgccaa     780
ataaacaaaa acgattctcc tgccactgca ggtgcctaag ctaatttagc cacataatgc     840
agtacttaat gtccaactgg cactgcaatt caagacggag tgacacttgt ttttagtaat     900
```

```
tcatccacat aatgttctta atgcattgct aattactttt ttaatggtaa tttcgaagca      960
ggtaaaagtt aatgtttaaa gtgtccagta agtaaaacta ctccagcaca tgctccaggt     1020
aatactgcta cttaagccac ataatgtttg accacatgtc ctgctggtac agtacttgat     1080
gatggaacat caactaattt tgtagcttcc gcaactgaat gtactaaatg ttctgctggc     1140
ttttttgcat caaaacaac tggttttaca gcaggtactg atacatgtac tgaatgtact      1200
aaaaaattaa cttctggtgc cacagctaaa gtatatgctg aagctactca aaaagtataa     1260
tgcgcctcca ctactttcgc taaatttta tcgatttcct tattatttat ttctttctat      1320
ttattgtga                                                             1329
```

<210> SEQ ID NO 2
<211> LENGTH: 442
<212> TYPE: PRT
<213> ORGANISM: Ichthyophthirius multifiliis
<220> FEATURE:
<221> NAME/KEY: MISC_FEATURE
<222> LOCATION: (1)..(442)
<223> OTHER INFORMATION: Ich IAG48 (GenBank: AF140273.1) protein
      sequence

<400> SEQUENCE: 2

```
Met Lys Tyr Asn Ile Leu Leu Ile Leu Ile Ile Ser Leu Phe Ile Asn
1               5                   10                  15

Glu Leu Arg Ala Val Pro Cys Pro Asp Gly Thr Gln Thr Gln Ala Gly
            20                  25                  30

Leu Thr Asp Val Gly Ala Ala Asp Leu Gly Thr Cys Val Asn Cys Arg
        35                  40                  45

Pro Asn Phe Tyr Tyr Asn Gly Gly Ala Ala Gln Gly Glu Ala Asn Gly
    50                  55                  60

Asn Gln Pro Phe Ala Ala Asn Asn Ala Ala Arg Gly Ile Cys Val Pro
65                  70                  75                  80

Cys Gln Ile Asn Arg Val Gly Ser Val Thr Asn Ala Gly Asp Leu Ala
                85                  90                  95

Thr Leu Ala Thr Gln Cys Ser Thr Gln Cys Pro Thr Gly Thr Ala Leu
            100                 105                 110

Asp Asp Gly Val Thr Asp Val Phe Asp Arg Ser Ala Ala Gln Cys Val
        115                 120                 125

Lys Cys Lys Pro Asn Phe Tyr Tyr Asn Gly Gly Ser Pro Gln Gly Glu
    130                 135                 140

Ala Pro Gly Val Gln Val Phe Ala Ala Gly Ala Ala Ala Gly Val
145                 150                 155                 160

Ala Ala Val Thr Ser Gln Cys Val Pro Cys Gln Leu Asn Lys Asn Asp
                165                 170                 175

Ser Pro Ala Thr Ala Gly Ala Gln Ala Asn Leu Ala Thr Gln Cys Ser
            180                 185                 190

Asn Gln Cys Pro Thr Gly Thr Val Leu Asp Asp Gly Val Thr Leu Val
        195                 200                 205

Phe Asn Thr Ser Ala Thr Leu Cys Val Lys Cys Arg Pro Asn Phe Tyr
    210                 215                 220

Tyr Asn Gly Gly Ser Pro Gln Gly Glu Ala Pro Gly Val Gln Val Phe
225                 230                 235                 240

Ala Ala Gly Ala Ala Ala Gly Val Ala Ala Val Thr Ser Gln Cys
                245                 250                 255

Val Pro Cys Gln Ile Asn Lys Asn Asp Ser Pro Ala Thr Ala Gly Ala
            260                 265                 270
```

Gln Ala Asn Leu Ala Thr Gln Cys Ser Thr Gln Cys Pro Thr Gly Thr
         275                 280                 285

Ala Ile Gln Asp Gly Val Thr Leu Val Phe Ser Asn Ser Ser Thr Gln
290                 295                 300

Cys Ser Gln Cys Ile Ala Asn Tyr Phe Phe Asn Gly Asn Phe Glu Ala
305                 310                 315                 320

Gly Lys Ser Gln Cys Leu Lys Cys Pro Val Ser Lys Thr Thr Pro Ala
                325                 330                 335

His Ala Pro Gly Asn Thr Ala Thr Gln Ala Thr Gln Cys Leu Thr Thr
            340                 345                 350

Cys Pro Ala Gly Thr Val Leu Asp Asp Gly Thr Ser Thr Asn Phe Val
        355                 360                 365

Ala Ser Ala Thr Glu Cys Thr Lys Cys Ser Ala Gly Phe Phe Ala Ser
370                 375                 380

Lys Thr Thr Gly Phe Thr Ala Gly Thr Asp Thr Cys Thr Glu Cys Thr
385                 390                 395                 400

Lys Lys Leu Thr Ser Gly Ala Thr Ala Lys Val Tyr Ala Glu Ala Thr
                405                 410                 415

Gln Lys Val Gln Cys Ala Ser Thr Thr Phe Ala Lys Phe Leu Ser Ile
            420                 425                 430

Ser Leu Leu Phe Ile Ser Phe Tyr Leu Leu
        435                 440

<210> SEQ ID NO 3
<211> LENGTH: 1329
<212> TYPE: DNA
<213> ORGANISM: Artificial Sequence
<220> FEATURE:
<223> OTHER INFORMATION: Ich IAG48 (TAA and TAG codons changed to CAG (* to Q))

<400> SEQUENCE: 3

```
atgaaatata atattttatt aattttaatt atttctttat ttattaatga attaagagct      60
gttccatgtc ctgatggtac tcagactcaa gctggattga ctgatgtagg tgctgctgat     120
cttggtactt gtgttaattg cagacctaat ttttactata tggtggtgc tgctcaggga     180
gaagctaatg gtaatcagcc tttcgcagca ataatgctg ctagaggtat atgtgtacca     240
tgccaaataa acagagtagg ctctgttacc aatgcaggtg acttagctac tttagccaca     300
cagtgcagta ctcagtgtcc tactggcact gcacttgatg atggagtgac agatgttttt     360
gatagatcag ccgcacagtg tgttaaatgc aaacctaact tttactataa tggtggttct     420
cctcagggtg aagctcctgg cgttcaggtt tttgctgctg gtgctgccgc tgcaggtgtt     480
gctgccgtta ctagtcagtg tgtaccttgc aactaaaca aaaacgattc tcctgccact     540
gcaggtgccc aggctaattt agccacacag tgtagcaatc agtgtcctac tggcactgta     600
cttgatgatg gagtgacact tgtttttaat acatcagcca cattatgtgt taaatgcaga     660
cctaactttt actataatgg tggttctcct cagggtgaag ctcctggcgt tcaggttttt     720
gctgctggtg ctgccgctgc aggtgttgct gccgttacta gtcagtgtgt accttgccaa     780
ataaacaaaa acgattctcc tgccactgca ggtgcccagg ctaatttagc cacacagtgc     840
agtactcagt gtccaactgg cactgcaatt caagacggag tgacacttgt ttttagtaat     900
tcatccacac agtgttctca gtgcattgct aattactttt ttaatggtaa tttcgaagca     960
ggtaaaagtc agtgtttaaa gtgtccagta agtaaaacta ctccagcaca tgctccaggt    1020
```

```
aatactgcta ctcaggccac acagtgtttg accacatgtc ctgctggtac agtacttgat    1080
gatggaacat caactaattt tgtagcttcc gcaactgaat gtactaaatg ttctgctggc    1140
ttttttgcat caaaaacaac tggttttaca gcaggtactg atacatgtac tgaatgtact    1200
aaaaaattaa cttctggtgc cacagctaaa gtatatgctg aagctactca aaaagtacag    1260
tgcgcctcca ctactttcgc taaattttta tcgatttcct tattatttat ttctttctat    1320
ttattgtga                                                            1329
```

<210> SEQ ID NO 4
<211> LENGTH: 442
<212> TYPE: PRT
<213> ORGANISM: Artificial Sequence
<220> FEATURE:
<223> OTHER INFORMATION: Ich IAG48 (TAA and TAG codons changed to CAG (*
      to Q)) PRT

<400> SEQUENCE: 4

```
Met Lys Tyr Asn Ile Leu Leu Ile Leu Ile Ile Ser Leu Phe Ile Asn
1               5                   10                  15

Glu Leu Arg Ala Val Pro Cys Pro Asp Gly Thr Gln Thr Gln Ala Gly
            20                  25                  30

Leu Thr Asp Val Gly Ala Ala Asp Leu Gly Thr Cys Val Asn Cys Arg
        35                  40                  45

Pro Asn Phe Tyr Tyr Asn Gly Gly Ala Gln Gly Glu Ala Asn Gly
    50                  55                  60

Asn Gln Pro Phe Ala Ala Asn Asn Ala Ala Arg Gly Ile Cys Val Pro
65                  70                  75                  80

Cys Gln Ile Asn Arg Val Gly Ser Val Thr Asn Ala Gly Asp Leu Ala
                85                  90                  95

Thr Leu Ala Thr Gln Cys Ser Thr Gln Cys Pro Thr Gly Thr Ala Leu
            100                 105                 110

Asp Asp Gly Val Thr Asp Val Phe Asp Arg Ser Ala Ala Gln Cys Val
        115                 120                 125

Lys Cys Lys Pro Asn Phe Tyr Tyr Asn Gly Gly Ser Pro Gln Gly Glu
    130                 135                 140

Ala Pro Gly Val Gln Val Phe Ala Ala Gly Ala Ala Ala Gly Val
145                 150                 155                 160

Ala Ala Val Thr Ser Gln Cys Val Pro Cys Gln Leu Asn Lys Asn Asp
                165                 170                 175

Ser Pro Ala Thr Ala Gly Ala Gln Ala Asn Leu Ala Thr Gln Cys Ser
            180                 185                 190

Asn Gln Cys Pro Thr Gly Thr Val Leu Asp Asp Gly Val Thr Leu Val
        195                 200                 205

Phe Asn Thr Ser Ala Thr Leu Cys Val Lys Cys Arg Pro Asn Phe Tyr
    210                 215                 220

Tyr Asn Gly Gly Ser Pro Gln Gly Glu Ala Pro Gly Val Gln Val Phe
225                 230                 235                 240

Ala Ala Gly Ala Ala Ala Gly Val Ala Ala Val Thr Ser Gln Cys
                245                 250                 255

Val Pro Cys Gln Ile Asn Lys Asn Asp Ser Pro Ala Thr Ala Gly Ala
            260                 265                 270

Gln Ala Asn Leu Ala Thr Gln Cys Ser Thr Gln Cys Pro Thr Gly Thr
        275                 280                 285

Ala Ile Gln Asp Gly Val Thr Leu Val Phe Ser Asn Ser Ser Thr Gln
    290                 295                 300
```

```
Cys Ser Gln Cys Ile Ala Asn Tyr Phe Phe Asn Gly Asn Phe Glu Ala
305                 310                 315                 320

Gly Lys Ser Gln Cys Leu Lys Cys Pro Val Ser Lys Thr Thr Pro Ala
            325                 330                 335

His Ala Pro Gly Asn Thr Ala Thr Gln Ala Thr Gln Cys Leu Thr Thr
        340                 345                 350

Cys Pro Ala Gly Thr Val Leu Asp Asp Gly Thr Ser Thr Asn Phe Val
    355                 360                 365

Ala Ser Ala Thr Glu Cys Thr Lys Cys Ser Ala Gly Phe Phe Ala Ser
370                 375                 380

Lys Thr Thr Gly Phe Thr Ala Gly Thr Asp Thr Cys Thr Glu Cys Thr
385                 390                 395                 400

Lys Lys Leu Thr Ser Gly Ala Thr Ala Lys Val Tyr Ala Glu Ala Thr
                405                 410                 415

Gln Lys Val Gln Cys Ala Ser Thr Thr Phe Ala Lys Phe Leu Ser Ile
            420                 425                 430

Ser Leu Leu Phe Ile Ser Phe Tyr Leu Leu
        435                 440

<210> SEQ ID NO 5
<211> LENGTH: 1329
<212> TYPE: DNA
<213> ORGANISM: Artificial Sequence
<220> FEATURE:
<223> OTHER INFORMATION: Ich IAG48 Codon Optimized

<400> SEQUENCE: 5
atgaagtaca acatactgtt aatacttatc atttcgcttt tcataaatga gcttagagca      60
gtgccctgcc ccgatggaac acaaacacag gccggattga cagacgttgg ggcagccgat     120
ctggggactt gtgtcaactg tcggccgaat ttttattata cggaggcgc agcgcagggt      180 gaggcgaacg gcaatcagcc ctttgcggcg aacaatgcag cgagaggcat ctgtgttcct     240
tgtcaaatca accgtgtagg cagcgtaaca aacgccgggg atcttgccac cctggccaca     300
cagtgtagca cacaatgccc tacggggacc gcattggatg atggggttac cgacgttttt     360
gatagatctg cagctcagtg cgtaaagtgt aaaccgaact tctattataa cggtggttct     420
ccacagggcg aggcccccgg ggtacaagtg tttgcggctg gtgcagccgc tgctggagtc     480
gccgccgtaa catcccaatg tgtgccctgc caactgaaca agaacgacag tcctgctacg     540
gccggagccc aggcaaacct ggctacgcaa tgttccaatc aatgccctac tgggaccgtg     600
ttggacgatg gggtaacatt ggttttcaat acgtcagcaa ctctgtgcgt taaatgtcgt     660
cccaatttct actataacgg aggtagccct cagggagaag ccccgggggt ccaggtcttc     720
gctgcaggtg ccgcagctgc gggggtggcc gcagttacat cgcaatgcgt accgtgccag     780
atcaacaaaa atgatagccc ggcgacagca gggctcaag cgaatcttgc aacccaatgc     840
tctactcaat gcccgaccgg tacagctatc caagacggag tgaccctggt tttttctaat     900
tcctcgacac agtgttcaca gtgcatcgct aattactttt ttaacgggaa ttttgaggca     960
gggaagtcgc aatgttttaaa atgtcctgtg agtaaaacga ctcccgcaca tgcccctggg    1020
aacacagcta cgcaggcaac ccaatgcctg acgacgtgtc cggcaggtac cgtcctggac    1080
gatgggactt ctacaaattt tgtagcctcc gcgactgaat gtacaaagtg cagcgcgggt    1140 ttttttcgcta gcaaaacgac ggggttcacg gcaggaacag atacttgcac ggaatgtacg    1200
aaaaaattaa cgagtggcgc gacggcgaag gtttacgcag aggcgactca gaaagtacaa    1260
```

```
tgtgcatcta caacattcgc aaagttcctt tccatctcct tgctgtttat ttcgttctac    1320
ctgctgtga                                                             1329
```

<210> SEQ ID NO 6
<211> LENGTH: 418
<212> TYPE: PRT
<213> ORGANISM: Artificial Sequence
<220> FEATURE:
<223> OTHER INFORMATION: Ich IAG48 Codon Optimized PRT

<400> SEQUENCE: 6

```
Met Lys Tyr Asn Ile Leu Leu Ile Leu Ile Ile Ser Leu Phe Ile Asn
1               5                   10                  15

Glu Leu Arg Ala Val Pro Cys Pro Asp Gly Thr Thr Gln Ala Gly Leu
            20                  25                  30

Thr Asp Val Gly Ala Ala Asp Leu Gly Thr Cys Val Asn Cys Arg Pro
        35                  40                  45

Asn Phe Tyr Tyr Asn Gly Gly Ala Ala Gly Glu Ala Asn Gly Asn Pro
    50                  55                  60

Phe Ala Ala Asn Asn Ala Ala Arg Gly Ile Cys Val Pro Cys Gln Ile
65                  70                  75                  80

Asn Arg Val Gly Ser Val Thr Asn Ala Gly Asp Leu Ala Thr Leu Ala
                85                  90                  95

Thr Cys Ser Thr Cys Pro Thr Gly Thr Ala Leu Asp Asp Gly Val Thr
            100                 105                 110

Asp Val Phe Asp Arg Ser Ala Ala Cys Val Lys Cys Lys Pro Asn Phe
        115                 120                 125

Tyr Tyr Asn Gly Gly Ser Pro Gly Glu Ala Pro Gly Val Val Phe Ala
    130                 135                 140

Ala Gly Ala Ala Ala Gly Val Ala Val Thr Ser Cys Val Pro
145                 150                 155                 160

Cys Gln Leu Asn Lys Asn Asp Ser Pro Ala Thr Ala Gly Ala Ala Asn
                165                 170                 175

Leu Ala Thr Cys Ser Asn Cys Pro Thr Gly Thr Val Leu Asp Asp Gly
            180                 185                 190

Val Thr Leu Val Phe Asn Thr Ser Ala Thr Leu Cys Val Lys Cys Arg
        195                 200                 205

Pro Asn Phe Tyr Tyr Asn Gly Gly Ser Pro Gly Glu Ala Pro Gly Val
    210                 215                 220

Val Phe Ala Ala Gly Ala Ala Ala Gly Val Ala Val Thr Ser
225                 230                 235                 240

Cys Val Pro Cys Gln Ile Asn Lys Asn Asp Ser Pro Ala Thr Ala Gly
                245                 250                 255

Ala Ala Asn Leu Ala Thr Cys Ser Thr Cys Pro Thr Gly Thr Ala Ile
            260                 265                 270

Gln Asp Gly Val Thr Leu Val Phe Ser Asn Ser Thr Cys Ser Cys
        275                 280                 285

Ile Ala Asn Tyr Phe Phe Asn Gly Asn Phe Glu Ala Gly Lys Ser Cys
    290                 295                 300

Leu Lys Cys Pro Val Ser Lys Thr Thr Pro Ala His Ala Pro Gly Asn
305                 310                 315                 320

Thr Ala Thr Ala Thr Cys Leu Thr Thr Cys Pro Ala Gly Thr Val Leu
                325                 330                 335

Asp Asp Gly Thr Ser Thr Asn Phe Val Ala Ser Ala Thr Glu Cys Thr
```

```
                340             345             350
Lys Cys Ser Ala Gly Phe Phe Ala Ser Lys Thr Thr Gly Phe Thr Ala
            355                 360                 365

Gly Thr Asp Thr Cys Thr Glu Cys Thr Lys Lys Leu Thr Ser Gly Ala
        370                 375                 380

Thr Ala Lys Val Tyr Ala Glu Ala Thr Gln Lys Val Cys Ala Ser Thr
385                 390                 395                 400

Thr Phe Ala Lys Phe Leu Ser Ile Ser Leu Leu Phe Ile Ser Phe Tyr
            405                 410                 415

Leu Leu

<210> SEQ ID NO 7
<211> LENGTH: 1407
<212> TYPE: DNA
<213> ORGANISM: Ichthyophthirius multifiliis
<220> FEATURE:
<221> NAME/KEY: misc_feature
<222> LOCATION: (1)..(1407)
<223> OTHER INFORMATION: IAG52A (GenBank: AF324424.1)

<400> SEQUENCE: 7
atgaaaaata atattttagt aatattgatt atttcattat ttatcaatta aattaaatct      60
gctaattgtc ctgttggaac tgaaactaac acagccggat aagttgatga tctaggaact     120
cctgcaaatt gtgttaattg ttagaaaaac ttttattata ataatgctgc tgctttcgtt     180
cctggtgcta gtacgtgtac accttgtcca taaaaaaaag atgctggtgc ttaaccaaat     240
ccacctgcta ctgctaattt agtcacataa tgtaacgtta aatgccctgc tggtaccgca     300
attgcaggtg gagcaacaga ttatgcagca ataatcacag aatgtgttaa ttgtagaatt     360 aattttttata tgaaaatgc tccaaatttt aatgcaggtg ctagtacatg cacagcttgt     420
ccggtaaaca gagttggtgg tgcattgact gctggtaatg ccgctaccat agtcgcataa     480
tgtaacgtcg catgtcctac tggtactgca cttgatgatg gagtaactac tgattatgtt     540
agatcattca cagaatgtgt taaatgtaga cttaactttt actataatgg taataatggt     600
aatactcctt tcaatccagg taaaagttaa tgcacacctt gtccggcaat taaacctgct     660
aatgttgctt aagctacttt aggtaatgat gctacaataa ccgcataatg taacgttgca     720
tgccctgatg gtactataag tgctgctgga gtaaataatt gggtagcaca aaacactgaa     780
tgtactaatt gtgctcctaa cttttacaat aataatgctc ctaatttcaa tccaggtaat     840
agtacatgcc taccttgccc agcaaataaa gattatggtg ctgaagccac tgcaggtggt     900
gccgctactt tagccaaata atgtaatatt gcatgccctg atggtactgc aattgctagt     960
ggagcaacta attatgtaat attataaaca gaatgtctaa attgtgctgc taactttttat    1020 tttgatggta ataatttcta ggcaggaagt agtagatgca aagcatgtcc agcaaataaa    1080
gtttaaggcg ctagcaaac tgcaggtggt actgctactt taattgcata atgtgccctt    1140
gaatgccctg ctggtactgt actcaccgat ggaacaacat ctactataa ataagcagca    1200 tctgaatgtg ttaaatgtgc tgccaactt tatactacaa ataaactga ttgggtagca    1260 ggtattgata catgtactag ttgtaataaa aaattaactt ctggcgctga agctaattta    1320
cctgaatctg ctaaaaaaaa tatataatgt gatttcgcta atttttatc aatttcctta    1380 ttattgattt cttattattt attatga                                        1407

<210> SEQ ID NO 8
<211> LENGTH: 468
```

<212> TYPE: PRT
<213> ORGANISM: Ichthyophthirius multifiliis
<220> FEATURE:
<221> NAME/KEY: MISC_FEATURE
<222> LOCATION: (1)..(468)
<223> OTHER INFORMATION: IAG52A (GenBank: AF324424.1) protein

<400> SEQUENCE: 8

```
Met Lys Asn Asn Ile Leu Val Ile Leu Ile Ile Ser Leu Phe Ile Asn
1               5                   10                  15

Gln Ile Lys Ser Ala Asn Cys Pro Val Gly Thr Glu Thr Asn Thr Ala
            20                  25                  30

Gly Gln Val Asp Asp Leu Gly Thr Pro Ala Asn Cys Val Asn Cys Gln
        35                  40                  45

Lys Asn Phe Tyr Tyr Asn Asn Ala Ala Ala Phe Val Pro Gly Ala Ser
    50                  55                  60

Thr Cys Thr Pro Cys Pro Gln Lys Lys Asp Ala Gly Ala Gln Pro Asn
65                  70                  75                  80

Pro Pro Ala Thr Ala Asn Leu Val Thr Gln Cys Asn Val Lys Cys Pro
                85                  90                  95

Ala Gly Thr Ala Ile Ala Gly Gly Ala Thr Asp Tyr Ala Ala Ile Ile
            100                 105                 110

Thr Glu Cys Val Asn Cys Arg Ile Asn Phe Tyr Asn Glu Asn Ala Pro
        115                 120                 125

Asn Phe Asn Ala Gly Ala Ser Thr Cys Thr Ala Cys Pro Val Asn Arg
    130                 135                 140

Val Gly Gly Ala Leu Thr Ala Gly Asn Ala Ala Thr Ile Val Ala Gln
145                 150                 155                 160

Cys Asn Val Ala Cys Pro Thr Gly Thr Ala Leu Asp Asp Gly Val Thr
                165                 170                 175

Thr Asp Tyr Val Arg Ser Phe Thr Glu Cys Val Lys Cys Arg Leu Asn
            180                 185                 190

Phe Tyr Tyr Asn Gly Asn Asn Gly Asn Thr Pro Phe Asn Pro Gly Lys
        195                 200                 205

Ser Gln Cys Thr Pro Cys Pro Ala Ile Lys Pro Ala Asn Val Ala Gln
    210                 215                 220

Ala Thr Leu Gly Asn Asp Ala Thr Ile Thr Ala Gln Cys Asn Val Ala
225                 230                 235                 240

Cys Pro Asp Gly Thr Ile Ser Ala Ala Gly Val Asn Asn Trp Val Ala
                245                 250                 255

Gln Asn Thr Glu Cys Thr Asn Cys Ala Pro Asn Phe Tyr Asn Asn Asn
            260                 265                 270

Ala Pro Asn Phe Asn Pro Gly Asn Ser Thr Cys Leu Pro Cys Pro Ala
        275                 280                 285

Asn Lys Asp Tyr Gly Ala Glu Ala Thr Ala Gly Gly Ala Ala Thr Leu
    290                 295                 300

Ala Lys Gln Cys Asn Ile Ala Cys Pro Asp Gly Thr Ala Ile Ala Ser
305                 310                 315                 320

Gly Ala Thr Asn Tyr Val Ile Leu Gln Thr Glu Cys Leu Asn Cys Ala
                325                 330                 335

Ala Asn Phe Tyr Phe Asp Gly Asn Asn Phe Gln Ala Gly Ser Ser Arg
            340                 345                 350

Cys Lys Ala Cys Pro Ala Asn Lys Val Gln Gly Ala Val Ala Thr Ala
        355                 360                 365

Gly Gly Thr Ala Thr Leu Ile Ala Gln Cys Ala Leu Glu Cys Pro Ala
```

```
                    370             375             380
Gly Thr Val Leu Thr Asp Gly Thr Thr Ser Thr Tyr Lys Gln Ala Ala
385                 390                 395                 400

Ser Glu Cys Val Lys Cys Ala Ala Asn Phe Tyr Thr Thr Lys Gln Thr
                405                 410                 415

Asp Trp Val Ala Gly Ile Asp Thr Cys Thr Ser Cys Asn Lys Lys Leu
                420                 425                 430

Thr Ser Gly Ala Glu Ala Asn Leu Pro Glu Ser Ala Lys Lys Asn Ile
            435                 440                 445

Gln Cys Asp Phe Ala Asn Phe Leu Ser Ile Ser Leu Leu Leu Ile Ser
    450                 455                 460

Tyr Tyr Leu Leu
465

<210> SEQ ID NO 9
<211> LENGTH: 1407
<212> TYPE: DNA
<213> ORGANISM: Artificial Sequence
<220> FEATURE:
<223> OTHER INFORMATION: Ich IAG52A (TAA and TAG codons changed to CAG
      (* to Q))

<400> SEQUENCE: 9
atgaaaaata atattttagt aatattgatt atttcattat ttatcaatca gattaaatct      60
gctaattgtc ctgttggaac tgaaactaac acagccggac aggttgatga tctaggaact     120
cctgcaaatt gtgttaattg tcagaaaaac ttttattata ataatgctgc tgctttcgtt     180
cctggtgcta gtacgtgtac accttgtcca cagaaaaaag atgctggtgc tcagccaaat     240
ccacctgcta ctgctaattt agtcacacag tgtaacgtta atgccctgc tggtaccgca      300 attgcaggtg gagcaacaga ttatgcagca ataatcacag aatgtgttaa ttgtagaatt     360 aattttttata tgaaaatgc tccaaatttt aatgcaggtg ctagtacatg cacagcttgt     420
ccggtaaaca gagttggtgg tgcattgact gctggtaatg ccgctaccat agtcgcacag     480
tgtaacgtcg catgtcctac tggtactgca cttgatgatg agtaactac tgattatgtt      540 agatcattca cagaatgtgt taaatgtaga cttaactttt actataatgg taataatggt     600
aatactcctt tcaatccagg taaaagtcag tgcacacctt gtccggcaat taaacctgct     660
aatgttgctc aggctacttt aggtaatgat gctacaataa ccgcacagtg taacgttgca     720
tgccctgatg gtactataag tgctgctgga gtaaataatt gggtagcaca aaacactgaa     780
tgtactaatt gtgctcctaa cttttacaat aataatgctc ctaatttcaa tccaggtaat     840
agtacatgcc taccttgccc agcaaataaa gattatggtg ctgaagccac tgcaggtggt     900
gccgctactt tagccaaaca gtgtaatatt gcatgccctg atggtactgc aattgctagt     960
ggagcaacta attatgtaat attcagaca gaatgtctaa attgtgctgc taactttttat    1020 tttgatggta ataattttcca ggcaggaagt agtagatgca agcatgtcc agcaaataaa    1080 gttcagggcg ctgtagcaac tgcaggtggt actgctactt taattgcaca gtgtgccctt    1140
gaatgccctg ctggtactgt actcaccgat ggaacaacat ctacttataa acaggcagca    1200
tctgaatgtg ttaaatgtgc tgccaacttt tatactacaa aacagactga ttgggtagca    1260
ggtattgata catgtactag ttgtaataaa aaattaactt ctggcgctga agctaattta    1320
cctgaatctg ctaaaaaaaa tatacagtgt gatttcgcta attttttatc aatttcctta    1380
ttattgattt cttattattt attatga                                        1407
```

<210> SEQ ID NO 10
<211> LENGTH: 468
<212> TYPE: PRT
<213> ORGANISM: Artificial Sequence
<220> FEATURE:
<223> OTHER INFORMATION: Ich IAG52A (TAA and TAG codons changed to CAG
      (* to Q)) PRT

<400> SEQUENCE: 10

Met Lys Asn Asn Ile Leu Val Ile Leu Ile Ile Ser Leu Phe Ile Asn
1               5                   10                  15

Gln Ile Lys Ser Ala Asn Cys Pro Val Gly Thr Glu Thr Asn Thr Ala
            20                  25                  30

Gly Gln Val Asp Asp Leu Gly Thr Pro Ala Asn Cys Val Asn Cys Gln
        35                  40                  45

Lys Asn Phe Tyr Tyr Asn Ala Ala Ala Phe Val Pro Gly Ala Ser
    50                  55                  60

Thr Cys Thr Pro Cys Pro Gln Lys Lys Asp Ala Gly Ala Gln Pro Asn
65                  70                  75                  80

Pro Pro Ala Thr Ala Asn Leu Val Thr Gln Cys Asn Val Lys Cys Pro
                85                  90                  95

Ala Gly Thr Ala Ile Ala Gly Gly Ala Thr Asp Tyr Ala Ala Ile Ile
            100                 105                 110

Thr Glu Cys Val Asn Cys Arg Ile Asn Phe Tyr Asn Glu Asn Ala Pro
        115                 120                 125

Asn Phe Asn Ala Gly Ala Ser Thr Cys Thr Ala Cys Pro Val Asn Arg
    130                 135                 140

Val Gly Gly Ala Leu Thr Ala Gly Asn Ala Ala Thr Ile Val Ala Gln
145                 150                 155                 160

Cys Asn Val Ala Cys Pro Thr Gly Thr Ala Leu Asp Asp Gly Val Thr
                165                 170                 175

Thr Asp Tyr Val Arg Ser Phe Thr Glu Cys Val Lys Cys Arg Leu Asn
            180                 185                 190

Phe Tyr Tyr Asn Gly Asn Asn Gly Asn Thr Pro Phe Asn Pro Gly Lys
        195                 200                 205

Ser Gln Cys Thr Pro Cys Pro Ala Ile Lys Pro Ala Asn Val Ala Gln
    210                 215                 220

Ala Thr Leu Gly Asn Asp Ala Thr Ile Thr Ala Gln Cys Asn Val Ala
225                 230                 235                 240

Cys Pro Asp Gly Thr Ile Ser Ala Ala Gly Val Asn Asn Trp Val Ala
                245                 250                 255

Gln Asn Thr Glu Cys Thr Asn Cys Ala Pro Asn Phe Tyr Asn Asn Asn
            260                 265                 270

Ala Pro Asn Phe Asn Pro Gly Asn Ser Thr Cys Leu Pro Cys Pro Ala
        275                 280                 285

Asn Lys Asp Tyr Gly Ala Glu Ala Thr Ala Gly Gly Ala Ala Thr Leu
    290                 295                 300

Ala Lys Gln Cys Asn Ile Ala Cys Pro Asp Gly Thr Ala Ile Ala Ser
305                 310                 315                 320

Gly Ala Thr Asn Tyr Val Ile Leu Gln Thr Glu Cys Leu Asn Cys Ala
                325                 330                 335

Ala Asn Phe Tyr Phe Asp Gly Asn Asn Phe Gln Ala Gly Ser Ser Arg
            340                 345                 350

Cys Lys Ala Cys Pro Ala Asn Lys Val Gln Gly Ala Val Ala Thr Ala
        355                 360                 365

| Gly | Gly | Thr | Ala | Thr | Leu | Ile | Ala | Gln | Cys | Ala | Leu | Glu | Cys | Pro | Ala |
|---|---|---|---|---|---|---|---|---|---|---|---|---|---|---|---|
| | 370 | | | | 375 | | | | 380 | | | | | | |

Gly Thr Val Leu Thr Asp Gly Thr Thr Ser Thr Tyr Lys Gln Ala Ala
385                     390                     395                     400

Ser Glu Cys Val Lys Cys Ala Ala Asn Phe Tyr Thr Thr Lys Gln Thr
                405                     410                     415

Asp Trp Val Ala Gly Ile Asp Thr Cys Thr Ser Cys Asn Lys Lys Leu
            420                     425                     430

Thr Ser Gly Ala Glu Ala Asn Leu Pro Glu Ser Ala Lys Lys Asn Ile
        435                     440                     445

Gln Cys Asp Phe Ala Asn Phe Leu Ser Ile Ser Leu Leu Leu Ile Ser
    450                     455                     460

Tyr Tyr Leu Leu
465

<210> SEQ ID NO 11
<211> LENGTH: 1407
<212> TYPE: DNA
<213> ORGANISM: Artificial Sequence
<220> FEATURE:
<223> OTHER INFORMATION: Ich IAG52A (Codon Optimized Sequence)

<400> SEQUENCE: 11

```
atgaagaaca acatattagt catcctgata atctcgttat tcattaatca gatcaaaagt      60
gcgaattgtc agttggaac ggagacgaac acagccgggc aggtggatga tttaggcacg     120
cccgcaaatt gtgtaaactg ccaaaagaat ttctactata caacgcggc agcattcgtt     180
ccagggcgt caacttgtac gccttgtccc caaaagaagg atgctggcgc tcagcccaat     240
ccaccccgcca cggcaaattt ggtaacccaa tgtaatgtaa atgtcccgc cgggacagcg     300
atagcgggag gagcaaccga ctacgcagcc atcataacag aatgcgtcaa ctgccgcatt     360
aatttctata tgagaacgc gcccaatttc aatgcagggg ccagtacctg tactgcttgc     420
ccagtaaacc gggtgggcgg ggcgcttacg gcagggaacg ccgccacgat tgtggcacag     480
tgtaacgtag catgtccaac gggtactgcc cttgatgacg cgtgacaac cgactatgtg     540
agatcgttta ccgagtgtgt gaaatgcaga ttgaacttct actacaacgg gaacaatgga     600
aatacgccgt taatccggg taaaagccaa tgcactcctt gccctgccat aaagccagcc     660
aatgtggcac aagcgactct tggtaacgac gccacaatca cagctcagtg caatgtagcg     720
tgccccgatg gtaccatctc agctgcaggt gttaataatt gggtggcaca aaacactgag     780
tgcaccaact gtgcgccgaa cttctacaat aacaacgctc cgaattttaa tccgggaaat     840
tctacgtgcc ttccatgtcc tgctaacaag gattatggcg ccgaggctac agctggcggg     900
gccgcgacgt tggccaaaca atgcaatatt gcatgccccg atggcacggc aatagctagt     960
ggggcaacga attatgtgat tttacagaca gagtgtctta actgcgcggc taattttta   1020
ttcgatggca caacttcca ggctggtagc tcgcgctgta aggcatgtcc agctaacaag    1080
gttcagggg cagttgcaac cgcaggagga accgctactc ttattgccca atgtgcctta    1140
gaatgtcctg ctggcacagt attgactgat gggacgacat caacctataa gcaggcggcg    1200
agtgaatgtg tgaaatgtgc tgcgaacttc tacactacaa acaaactga ctgggtcgcg    1260
ggtattgaca cctgcacctc atgtaataag aagttaactt ccggggctga agctaactta    1320
ccagaatcgg ctaagaaaaa tattcaatgc gacttcgcta acttcttaag tataagtctg    1380
cttttgattt cttattatct gctttga                                       1407
```

<210> SEQ ID NO 12
<211> LENGTH: 450
<212> TYPE: PRT
<213> ORGANISM: Artificial Sequence
<220> FEATURE:
<223> OTHER INFORMATION: Ich IAG52A (Codon Optimized Sequence) PRT

<400> SEQUENCE: 12

```
Met Lys Asn Asn Ile Leu Val Ile Leu Ile Ser Leu Phe Ile Asn
1               5                   10                  15

Ile Lys Ser Ala Asn Cys Pro Val Gly Thr Glu Thr Asn Thr Ala Gly
            20                  25                  30

Val Asp Asp Leu Gly Thr Pro Ala Asn Cys Val Asn Cys Lys Asn Phe
                35                  40                  45

Tyr Tyr Asn Asn Ala Ala Ala Phe Val Pro Gly Ala Ser Thr Cys Thr
    50                  55                  60

Pro Cys Pro Lys Lys Asp Ala Gly Ala Pro Asn Pro Pro Ala Thr Ala
65                  70                  75                  80

Asn Leu Val Thr Cys Asn Val Lys Cys Pro Ala Gly Thr Ala Ile Ala
                85                  90                  95

Gly Gly Ala Thr Asp Tyr Ala Ala Ile Ile Thr Glu Cys Val Asn Cys
                100                 105                 110

Arg Ile Asn Phe Tyr Asn Glu Asn Ala Pro Asn Phe Asn Ala Gly Ala
            115                 120                 125

Ser Thr Cys Thr Ala Cys Pro Val Asn Arg Val Gly Gly Ala Leu Thr
    130                 135                 140

Ala Gly Asn Ala Ala Thr Ile Val Ala Cys Asn Val Ala Cys Pro Thr
145                 150                 155                 160

Gly Thr Ala Leu Asp Asp Gly Val Thr Thr Asp Tyr Val Arg Ser Phe
                165                 170                 175

Thr Glu Cys Val Lys Cys Arg Leu Asn Phe Tyr Tyr Asn Gly Asn Asn
                180                 185                 190

Gly Asn Thr Pro Phe Asn Pro Gly Lys Ser Cys Thr Pro Cys Pro Ala
            195                 200                 205

Ile Lys Pro Ala Asn Val Ala Ala Thr Leu Gly Asn Asp Ala Thr Ile
    210                 215                 220

Thr Ala Cys Asn Val Ala Cys Pro Asp Gly Thr Ile Ser Ala Ala Gly
225                 230                 235                 240

Val Asn Asn Trp Val Ala Gln Asn Thr Glu Cys Thr Asn Cys Ala Pro
                245                 250                 255

Asn Phe Tyr Asn Asn Ala Pro Asn Phe Asn Pro Gly Asn Ser Thr
            260                 265                 270

Cys Leu Pro Cys Pro Ala Asn Lys Asp Tyr Gly Ala Glu Ala Thr Ala
    275                 280                 285

Gly Gly Ala Ala Thr Leu Ala Lys Cys Asn Ile Ala Cys Pro Asp Gly
290                 295                 300

Thr Ala Ile Ala Ser Gly Ala Thr Asn Tyr Val Ile Leu Thr Glu Cys
305                 310                 315                 320

Leu Asn Cys Ala Ala Asn Phe Tyr Phe Asp Gly Asn Asn Phe Ala Gly
                325                 330                 335

Ser Ser Arg Cys Lys Ala Cys Pro Ala Asn Lys Val Gly Ala Val Ala
            340                 345                 350

Thr Ala Gly Gly Thr Ala Thr Leu Ile Ala Cys Ala Leu Glu Cys Pro
                355                 360                 365
```

Ala Gly Thr Val Leu Thr Asp Gly Thr Thr Ser Thr Tyr Lys Ala Ala
    370             375                 380

Ser Glu Cys Val Lys Cys Ala Ala Asn Phe Tyr Thr Thr Lys Thr Asp
385                 390                 395                 400

Trp Val Ala Gly Ile Asp Thr Cys Thr Ser Cys Asn Lys Lys Leu Thr
            405                 410                 415

Ser Gly Ala Glu Ala Asn Leu Pro Glu Ser Ala Lys Lys Asn Ile Cys
        420                 425                 430

Asp Phe Ala Asn Phe Leu Ser Ile Ser Leu Leu Ile Ser Tyr Tyr
        435                 440                 445

Leu Leu
    450

<210> SEQ ID NO 13
<211> LENGTH: 1266
<212> TYPE: DNA
<213> ORGANISM: Ichthyophthirius multifiliis
<220> FEATURE:
<221> NAME/KEY: misc_feature
<222> LOCATION: (1)..(1266)
<223> OTHER INFORMATION: IAG52B

<400> SEQUENCE: 13
atggtgaatt gcccgaatgg cgccgccatc gccaatggcc agagcgatac cggcgccgcc      60
gatatcaata cctgcaccca ttgccagaaa cattttattt taatggcgg caatccggcc     120
ggccaggccc cgggcgccgt gcagtttaat ccgggcgtga ccagtgcat cgcctgccag     180
gtgcataaag ccgatagcca gcatcgccag ggcggcgatg ccaatctggc cgcccagtgc     240
agcaatctgt gccggccgg caccgccgtg gaggatggca gcccgacctt acccagagc      300
ctgacccagt gcgtgaattg caaaccgaat tttattttta atggcggcaa tccgaccggc     360
caggccccgg cgccggcca gtttgatccg acccagctga tcgccaatcc ggatctggcc     420
aataatccgg aggtgccgaa tgtgagcagc ccgaatggcc agtgcgtggc ctgccaggtg     480
aataaaagcg atagccagct cgcccgggc gcccaggcca atctggccac ccagtgcaat     540
aatgagtgcc cgaccggcac cgccatccag gatggcgcca tctttatcta tacccagagc     600
atcagccagt gcacctttg caaagtggat tttattttta atggcggcaa tccgagcgcc     660
cagaatccgg gcaatggcca gtttacccg ggccagctga tcgccaatcc ggatgccgcc     720
accgccgccc agatcccgat ggtgccgggc ccgaatagca aatgcgtggc ctgcgagagc     780
aaaaaaacca atagccagag ccgcagcggc ctggaggcca tctggccgc ccagtgcggc     840
accgagtgcc cggccggcac cctggtgacc gatggcgtga ccccgaccta ccgtgagc       900
ctgagccagt gcgtgaattg caaagccggc tttatcaga atagcaattt tgaggccggc     960
aaaagccagt gcaataaatg cgccgtgagc aaaaccggca gcgccagcgt gccgggcaat    1020
agcgccacca gcgccaccca gtgccagaat gattgcccgg ccggcaccgt ggtggatgat    1080
ggcagcacca ttttgtggc cctggccagc gagtgcacca atgccaggc caattttat      1140
gccagcaaaa ccagcggctt tgccgccggc accgatacct gcaccgagtg cagcaaaaaa    1200
ctgaccagcg gcgccaccgc caaagtgtat gccgaggcca cccagaaagc ccagtgcgcc    1260
agctga                                                             1266

<210> SEQ ID NO 14
<211> LENGTH: 422
<212> TYPE: PRT

<213> ORGANISM: Ichthyophthirius multifiliis
<220> FEATURE:
<221> NAME/KEY: MISC_FEATURE
<222> LOCATION: (1)..(422)
<223> OTHER INFORMATION: IAG52B

<400> SEQUENCE: 14

```
Met Val Asn Cys Pro Asn Gly Ala Ala Ile Ala Asn Gly Gln Ser Asp
1               5                   10                  15

Thr Gly Ala Ala Asp Ile Asn Thr Cys Thr His Cys Gln Lys His Phe
            20                  25                  30

Tyr Phe Asn Gly Gly Asn Pro Ala Gly Gln Ala Pro Gly Ala Val Gln
        35                  40                  45

Phe Asn Pro Gly Val Ser Gln Cys Ile Ala Cys Gln Val His Lys Ala
    50                  55                  60

Asp Ser Gln His Arg Gln Gly Gly Asp Ala Asn Leu Ala Ala Gln Cys
65                  70                  75                  80

Ser Asn Leu Cys Pro Ala Gly Thr Ala Val Glu Asp Gly Ser Pro Thr
                85                  90                  95

Phe Thr Gln Ser Leu Thr Gln Cys Val Asn Cys Lys Pro Asn Phe Tyr
            100                 105                 110

Phe Asn Gly Gly Asn Pro Thr Gly Gln Ala Pro Gly Ala Gly Gln Phe
        115                 120                 125

Asp Pro Thr Gln Leu Ile Ala Asn Pro Asp Leu Ala Asn Asn Pro Glu
    130                 135                 140

Val Pro Asn Val Ser Ser Pro Asn Gly Gln Cys Val Ala Cys Gln Val
145                 150                 155                 160

Asn Lys Ser Asp Ser Gln Leu Arg Pro Gly Ala Gln Ala Asn Leu Ala
                165                 170                 175

Thr Gln Cys Asn Asn Glu Cys Pro Thr Gly Thr Ala Ile Gln Asp Gly
            180                 185                 190

Ala Ile Phe Ile Tyr Thr Gln Ser Ile Ser Gln Cys Thr Phe Cys Lys
        195                 200                 205

Val Asp Phe Tyr Phe Asn Gly Gly Asn Pro Ser Ala Gln Asn Pro Gly
    210                 215                 220

Asn Gly Gln Phe Thr Pro Gly Gln Leu Ile Ala Asn Pro Asp Ala Ala
225                 230                 235                 240

Thr Ala Ala Gln Ile Pro Met Val Pro Gly Pro Asn Ser Lys Cys Val
                245                 250                 255

Ala Cys Glu Ser Lys Lys Thr Asn Ser Gln Ser Arg Ser Gly Leu Glu
            260                 265                 270

Ala Asn Leu Ala Ala Gln Cys Gly Thr Glu Cys Pro Ala Gly Thr Leu
        275                 280                 285

Val Thr Asp Gly Val Thr Pro Thr Tyr Thr Val Ser Leu Ser Gln Cys
    290                 295                 300

Val Asn Cys Lys Ala Gly Phe Tyr Gln Asn Ser Asn Phe Glu Ala Gly
305                 310                 315                 320

Lys Ser Gln Cys Asn Lys Cys Ala Val Ser Lys Thr Gly Ser Ala Ser
                325                 330                 335

Val Pro Gly Asn Ser Ala Thr Ser Ala Thr Gln Cys Gln Asn Asp Cys
            340                 345                 350

Pro Ala Gly Thr Val Val Asp Asp Gly Thr Ser Thr Asn Phe Val Ala
        355                 360                 365

Leu Ala Ser Glu Cys Thr Lys Cys Gln Ala Asn Phe Tyr Ala Ser Lys
    370                 375                 380
```

Thr Ser Gly Phe Ala Ala Gly Thr Asp Thr Cys Thr Glu Cys Ser Lys
385                 390                 395                 400

Lys Leu Thr Ser Gly Ala Thr Ala Lys Val Tyr Ala Glu Ala Thr Gln
            405                 410                 415

Lys Ala Gln Cys Ala Ser
            420

<210> SEQ ID NO 15
<211> LENGTH: 1263
<212> TYPE: DNA
<213> ORGANISM: Artificial Sequence
<220> FEATURE:
<223> OTHER INFORMATION: Ich IAG52B (Codon Optimized)

<400> SEQUENCE: 15
gttaattgtc ctaatggtgc tgcaattgcg aatggataat ctgatacagg agctgcagat      60
ataaatactt gtactcattg ctaaaaacac ttttacttta atggtggtaa tcctgcaggt     120
caggctcctg gtgctgtaca attcaatcca ggtgttagtc agtgcatagc ttgccaagta     180
cacaaagccg attctcaaca cagataaggt ggtgatgcta atttagccgc ataatgtagc     240
aacttatgtc ctgctggcac tgcagttgaa gatggatcac ctacttttac ttaatccctc     300
acataatgtg ttaattgtaa acctaacttt tactttaatg gtggtaatcc tacaggtcag     360
gctcctggtc tggataatt cgatccaact taattgattg caaatcctga tcttgctaat      420
aatcctgaag ttcctaatgt ttctagccct aatggttaat gcgtagcttg ctaagtaaac     480
aagtctgatt ctcaattaag accaggtgct taggctaatt tagccacata atgtaacaat     540
gaatgtccta ctggcactgc tattcaagac ggagcaatat ttatttatac ttaatcaatc     600
tcataatgta cttttgtaa agttgacttt tactttaatg gtggcaatcc ttcagctcag      660
aatcctggta atggataatt cactccaggt taattgattg caaatcctga tgctgctact     720
gctgcttaaa ttcctatggt tcctggcccc aatagtaaat gcgtagcttg cgaatcaaaa     780
aagaccaatt cttaatccag atcaggtctt gaggctaatt tagccgcata atgtggcact     840
gaatgtcctg ctggcactct tgttacagac ggagtaacac ctacttatac tgtatcactc     900
tcataatgtg ttaattgtaa agctggcttt tactaaaata gtaatttcga agcaggtaaa     960
agttaatgca ataagtgtgc agtaagtaaa actggttcag catctgttcc aggtaatagt    1020
gctacttcag ccacataatg ttaaaacgat tgccctgctg gtacagtggt tgatgatggt    1080
acatcaacta attttgtagc tttagcaagt gaatgtacta atgttaggc taactttttat    1140 gcatcaaaaa catctggttt tgcagcaggt actgatacat gtactgaatg ttctaaaaaa    1200
ttaacttctg gtgctacagc taaagtatat gctgaagcta cttaaaaagc ataatgcgcc    1260
agt                                                                  1263

<210> SEQ ID NO 16
<211> LENGTH: 394
<212> TYPE: PRT
<213> ORGANISM: Artificial Sequence
<220> FEATURE:
<223> OTHER INFORMATION: Ich IAG52B (Codon Optimized)

<400> SEQUENCE: 16

Val Asn Cys Pro Asn Gly Ala Ala Ile Ala Asn Gly Ser Asp Thr Gly
1               5                   10                  15

Ala Ala Asp Ile Asn Thr Cys Thr His Cys Lys His Phe Tyr Phe Asn
            20                  25                  30

-continued

```
Gly Gly Asn Pro Ala Gly Gln Ala Pro Gly Ala Val Gln Phe Asn Pro
        35                  40                  45
Gly Val Ser Gln Cys Ile Ala Cys Gln Val His Lys Ala Asp Ser Gln
 50                  55                  60
His Arg Gly Gly Asp Ala Asn Leu Ala Ala Cys Ser Asn Leu Cys Pro
 65              70                  75                  80
Ala Gly Thr Ala Val Glu Asp Gly Ser Pro Thr Phe Thr Ser Leu Thr
                 85                  90                  95
Cys Val Asn Cys Lys Pro Asn Phe Tyr Phe Asn Gly Gly Asn Pro Thr
                100                 105                 110
Gly Gln Ala Pro Gly Ala Gly Phe Asp Pro Thr Leu Ile Ala Asn Pro
            115                 120                 125
Asp Leu Ala Asn Asn Pro Glu Val Pro Asn Val Ser Ser Pro Asn Gly
130                 135                 140
Cys Val Ala Cys Val Asn Lys Ser Asp Ser Gln Leu Arg Pro Gly Ala
145                 150                 155                 160
Ala Asn Leu Ala Thr Cys Asn Asn Glu Cys Pro Thr Gly Thr Ala Ile
                165                 170                 175
Gln Asp Gly Ala Ile Phe Ile Tyr Thr Ser Ile Ser Cys Thr Phe Cys
            180                 185                 190
Lys Val Asp Phe Tyr Phe Asn Gly Gly Asn Pro Ser Ala Gln Asn Pro
        195                 200                 205
Gly Asn Gly Phe Thr Pro Gly Leu Ile Ala Asn Pro Asp Ala Ala Thr
    210                 215                 220
Ala Ala Ile Pro Met Val Pro Gly Pro Asn Ser Lys Cys Val Ala Cys
225                 230                 235                 240
Glu Ser Lys Lys Thr Asn Ser Ser Arg Ser Gly Leu Glu Ala Asn Leu
                245                 250                 255
Ala Ala Cys Gly Thr Glu Cys Pro Ala Gly Thr Leu Val Thr Asp Gly
            260                 265                 270
Val Thr Pro Thr Tyr Thr Val Ser Leu Ser Cys Val Asn Cys Lys Ala
        275                 280                 285
Gly Phe Tyr Asn Ser Asn Phe Glu Ala Gly Lys Ser Cys Asn Lys Cys
    290                 295                 300
Ala Val Ser Lys Thr Gly Ser Ala Ser Val Pro Gly Asn Ser Ala Thr
305                 310                 315                 320
Ser Ala Thr Cys Asn Asp Cys Pro Ala Gly Thr Val Val Asp Asp Gly
                325                 330                 335
Thr Ser Thr Asn Phe Val Ala Leu Ala Ser Glu Cys Thr Lys Cys Ala
            340                 345                 350
Asn Phe Tyr Ala Ser Lys Thr Ser Gly Phe Ala Ala Gly Thr Asp Thr
        355                 360                 365
Cys Thr Glu Cys Ser Lys Lys Leu Thr Ser Gly Ala Thr Ala Lys Val
    370                 375                 380
Tyr Ala Glu Ala Thr Lys Ala Cys Ala Ser
385                 390
```